United States Patent [19]

Holmes et al.

[11] Patent Number: 5,328,809

[45] Date of Patent: Jul. 12, 1994

[54] PATTERNING OF SEMICONDUCTIVE POLYMERS

[75] Inventors: Andrew Holmes; Donal D. Bradley; Richard H. Friend; Arno Kraft; Paul Burn; Adam Brown, all of Cambridge, United Kingdom

[73] Assignee: Cambridge Display Technology Limited, Cambridge, United Kingdom

[21] Appl. No.: 748,795

[22] Filed: Aug. 22, 1991

[30] Foreign Application Priority Data

Aug. 24, 1990 [GB] United Kingdom ............... 9018698

[51] Int. Cl.⁵ ..................... B05D 1/32; G03C 5/00
[52] U.S. Cl. ..................... 430/321; 430/313; 430/330; 427/272; 427/392.2; 427/384
[58] Field of Search ............ 430/330, 325, 323, 321, 430/318, 313, 322; 427/270, 271, 272, 273, 372.2, 384; 252/500

[56] References Cited

U.S. PATENT DOCUMENTS

| | | | |
|---|---|---|---|
| 3,002,848 | 10/1961 | Clark | 427/270 |
| 3,521,321 | 11/1971 | Williams et al. | |
| 4,454,307 | 6/1984 | Cheshire | 525/379 |
| 4,772,421 | 9/1988 | Ikenaga et al. | 524/80 |
| 4,816,383 | 3/1989 | Taguchi et al. | 430/322 |
| 4,868,284 | 9/1989 | Murase et al. | |
| 4,900,782 | 2/1990 | Han et al. | |
| 4,950,950 | 8/1990 | Perry et al. | |
| 5,053,166 | 10/1991 | Murase | 252/500 |
| 5,064,572 | 11/1991 | Ohnishi et al. | 252/500 |
| 5,068,060 | 11/1991 | Jen et al. | 252/500 |
| 5,200,112 | 4/1993 | Angelopoulos et al. | 427/384 |
| 5,202,061 | 4/1993 | Angelopoulos et al. | 252/500 |

FOREIGN PATENT DOCUMENTS

| | | |
|---|---|---|
| 0182548A3 | 5/1986 | European Pat. Off. |
| 0373582A1 | 6/1990 | European Pat. Off. |
| 0388768A2 | 9/1990 | European Pat. Off. |
| 3704411A1 | 8/1987 | Fed. Rep. of Germany |
| WO88/00954 | 2/1988 | PCT Int'l Appl. |

OTHER PUBLICATIONS

Electric Phenomena, vol. 111, 1989, pp. 812–813.
Polymer Communications, vol. 28 Sep. 1987.
Journal of Molecular Electronics, vol. 4, No. 1, Jan.–Mar. 1988, pp. 37–46.
Chemistry Letters, No. 7, 1988, pp. 1201–1204.
Polymer, 1989, vol. 30, Jun. 1989 (Conf. Issue), pp. 1041–1047.
Makromol. Chem., vol. 190, 1987, pp. 389–397.
Polymer Bulletin, Spring 1989, No. 4, pp. 409–412.
Polymer, 1990, vol. 31, Jun. 1990, pp. 1137–1141.
Ballard et al., "Synthesis of Polyphenylene From a cis-Dihydrocathechol, a Biologically Produced Monomer", Macromolecules, 21:924–304 (1988).
Conticello et al., "Ring-Opening Metathesis Polymerization of Substituted Bicyclo[2.2.2]octadienes: A New Precursor Route to Poly(1,4-phenylenevinylene)," J. Am. Chem. Soc., 114:9708–9710 (1992).

(List continued on next page.)

Primary Examiner—Charles L. Bowers, Jr.
Assistant Examiner—M. Angebranndt
Attorney, Agent, or Firm—Merchant & Gould

[57] ABSTRACT

A method is provided for forming in a semiconductive conjugated polymer at least first and second regions having different optical properties. The method comprises: forming a layer of a precursor polymer and permitting the first region to come into contact with a reactant, such as an acid, and heat while permitting the second region to come into contact with a lower concentration of the reactant. The reactant affects the conversion conditions of the precursor polymer in such a way as to control the optical properties of at least the first region so that the optical properties of the first region are different from those of the second region.

The precursor polymer may comprise a poly(arylene-1,2-ethanediyl) polymer, at least some of the ethane groups of which include a modifier group whose susceptibility to elimination is increased in the presence of the reactant.

25 Claims, 56 Drawing Sheets

OTHER PUBLICATIONS

Grem et al., "Realization of a Blue-Light-Emitting Device Using Poly(p-phenylene)", *Adv. Mater.*, 4:36–37 (1992).

Hsieh, "Synthesis of Poly(Phenylene Acetylene) from Poly(Phenylene Vinylene)", *Polym. Prepr.*, 32:631 (1991).

Ni et al., "Conductivity, Optical Absorption, Photoluminescence, and X-Band Optically Detected Magnetic Resonance of Novel Poly(2,5-dibutoxyparaphenyleneacetylene) (PDBOPA)", *Syn. Metals*, 49-50:447–452 (1992).

Swanson et al., "Photoluminescence, Electroluminescence, and Optically Detected Magnetic Resonance Study of 2,5-dialkoxy Derivatives of Poly(p-phenylene-acetylene) (PPA) and PPA-Based Light-Emitting Diodes", ICSM, Gottenburg Aug. 1992, *Synth. Met., in press* (1993).

Yoshino et al., "Optical Recording Utilizing Conducting Polymers, Poly(p-phenylene vinylene) and Its Derivatives", *Japan J. App. Physics*, 29:1514–1516 (1990).

FIG. 2a
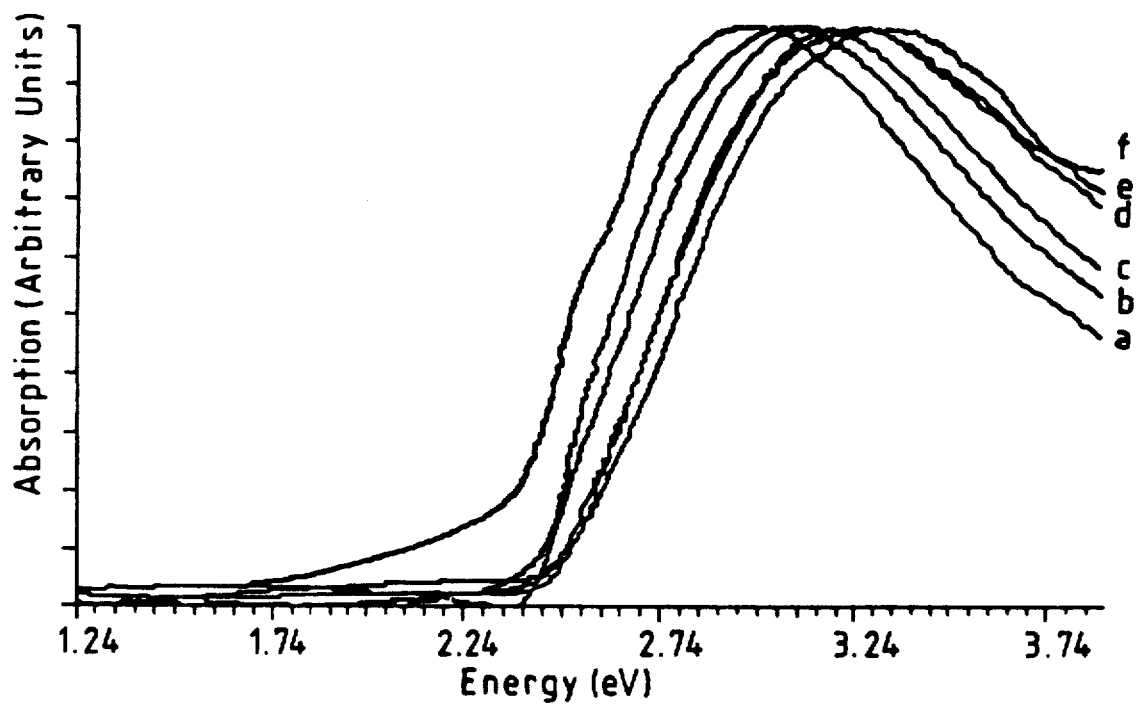
FIG. 2b  PMPV absorption spectrum
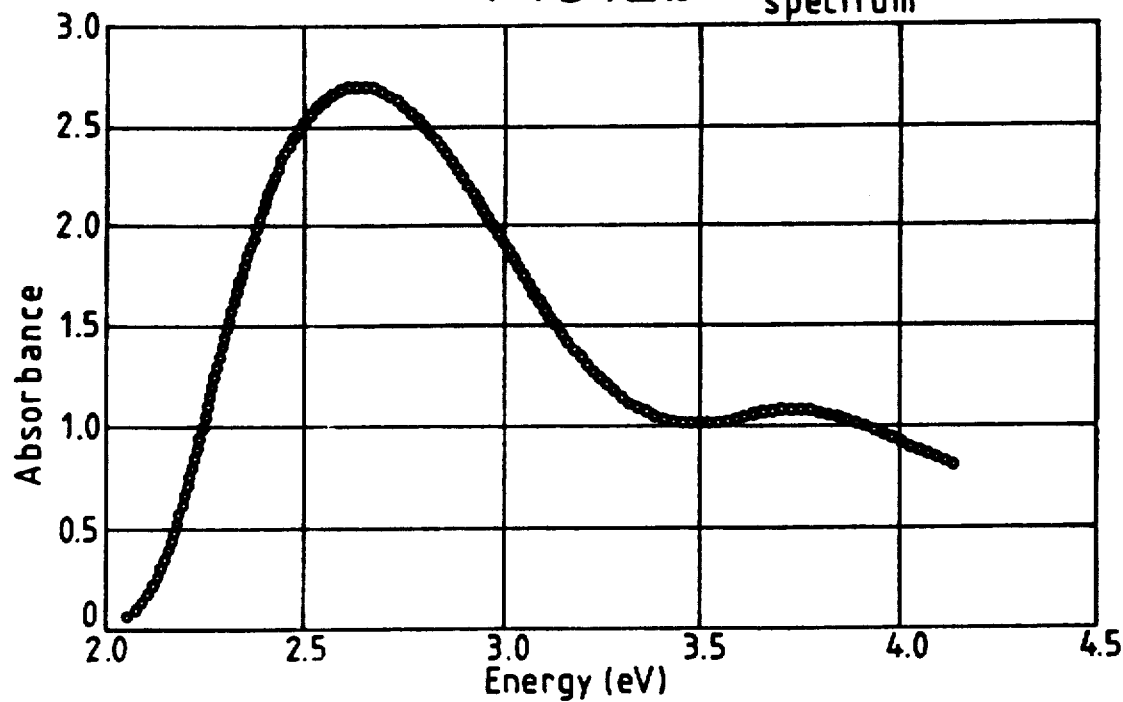

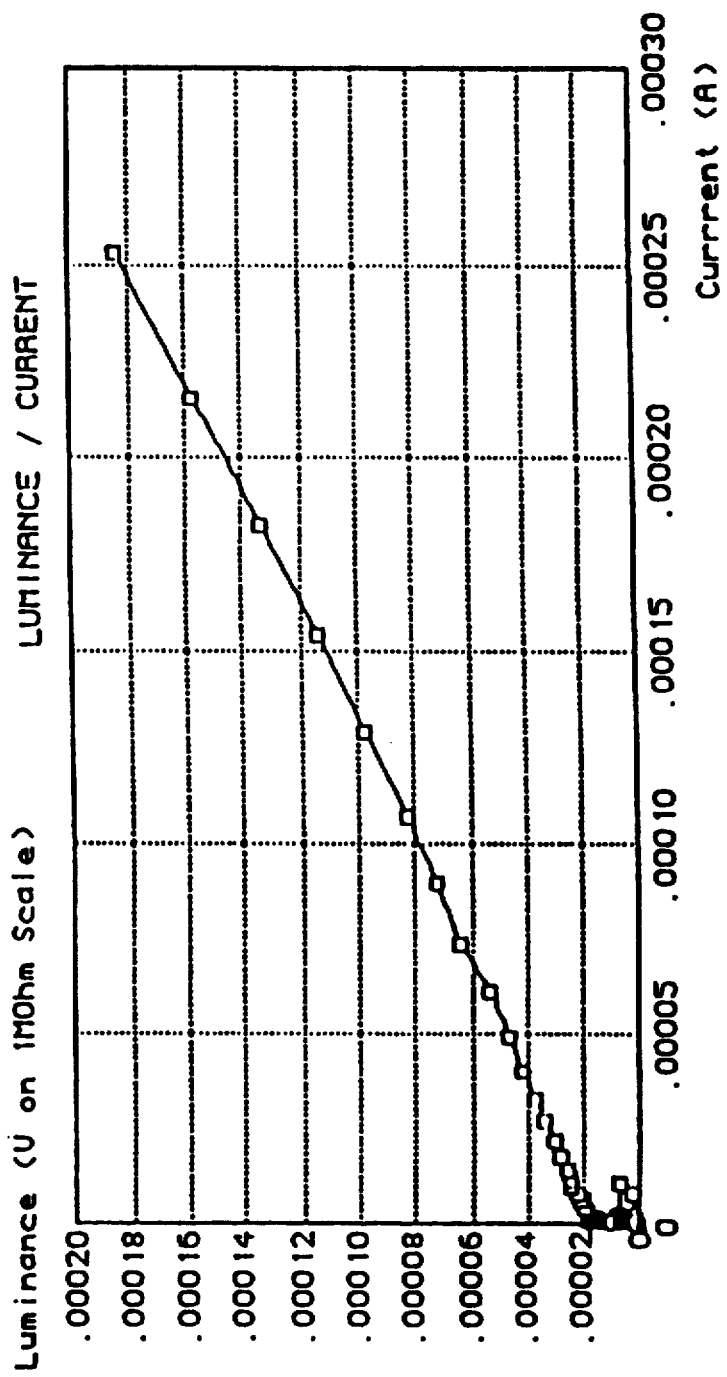

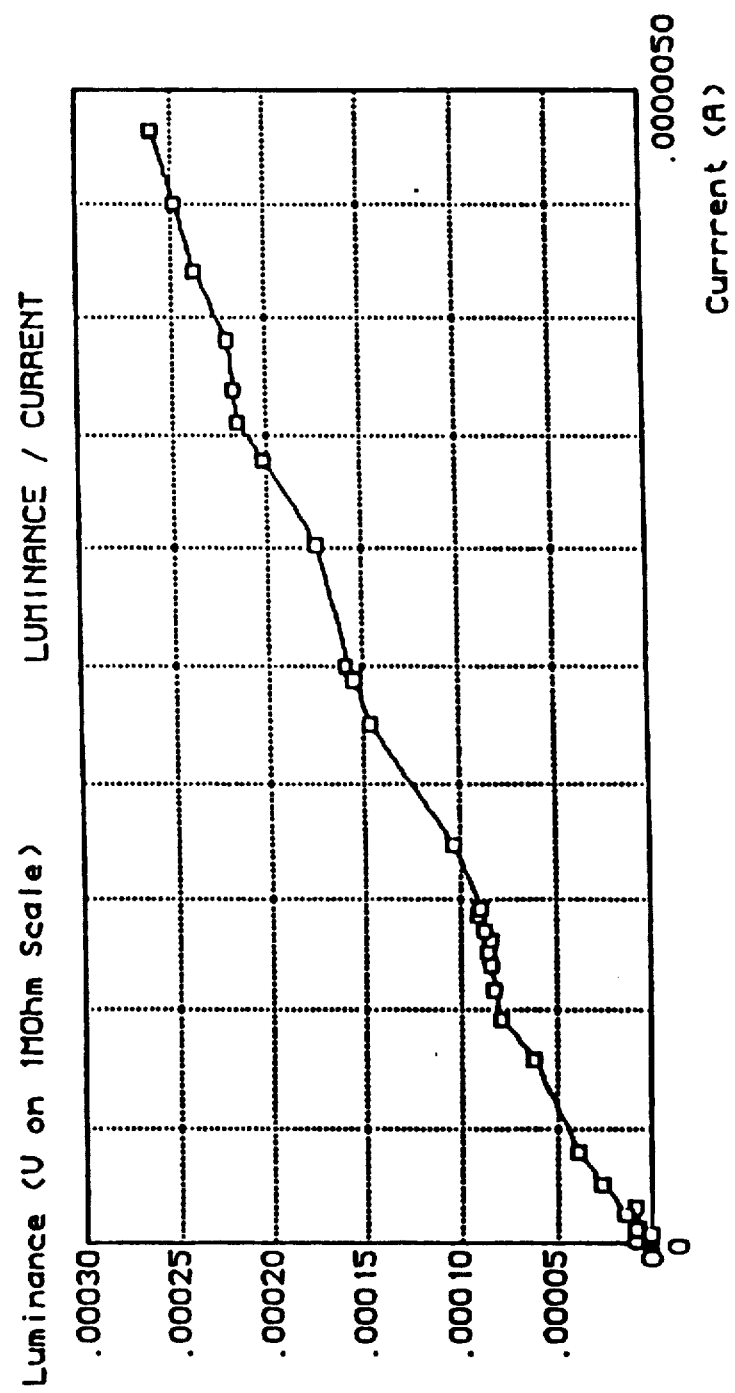

Electroluminescent Quantum Yield of the Random Copolymers of PPV and Dimethoxy PPV Electroluminescent Quantum Yield of the Random Copolymers of PPV and PTV Electroluminescent Quantum Yield of the Random Copolymers of PPV and Dimethyl PPV

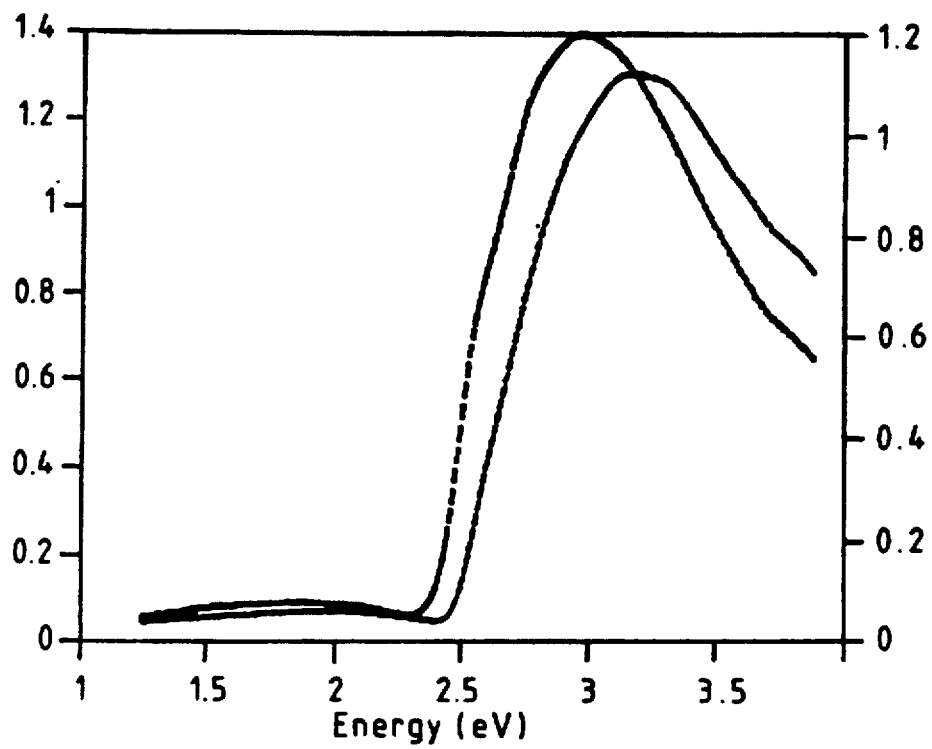
FIG. 16 PLB 03-12 Absorption Spectra
□ Capped   ◇ Uncapped
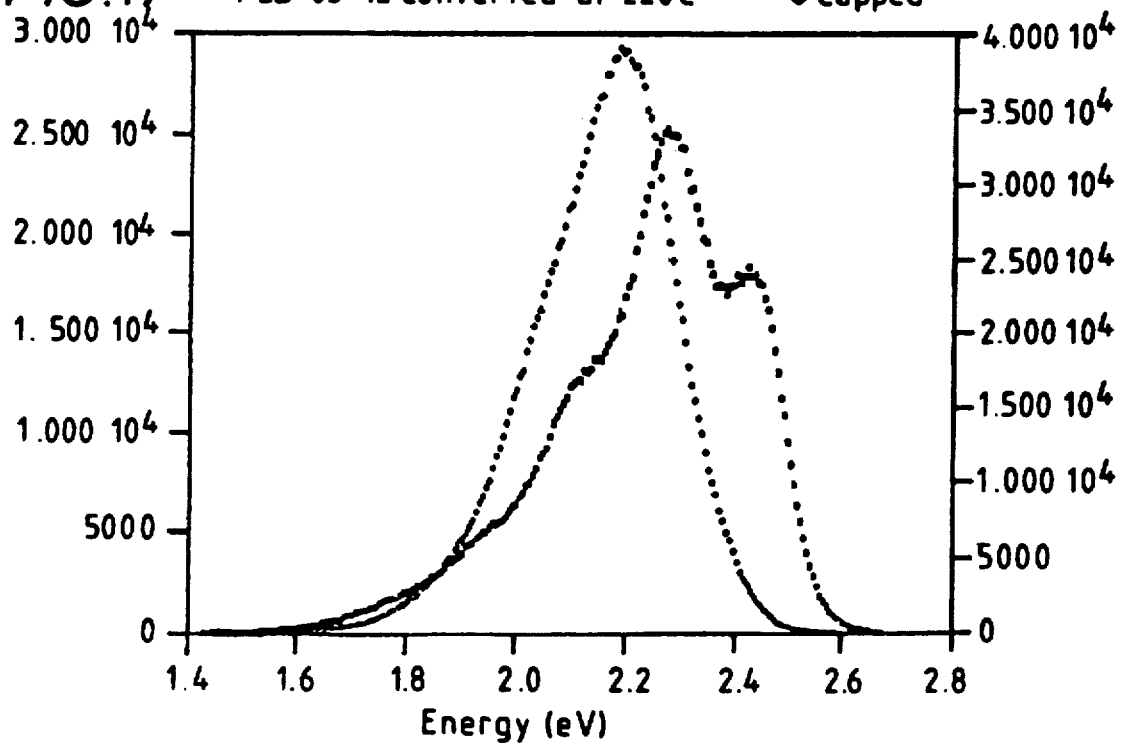
FIG. 17 PLB 03-12 Converted at 220C
□ Uncapped   ◇ Capped

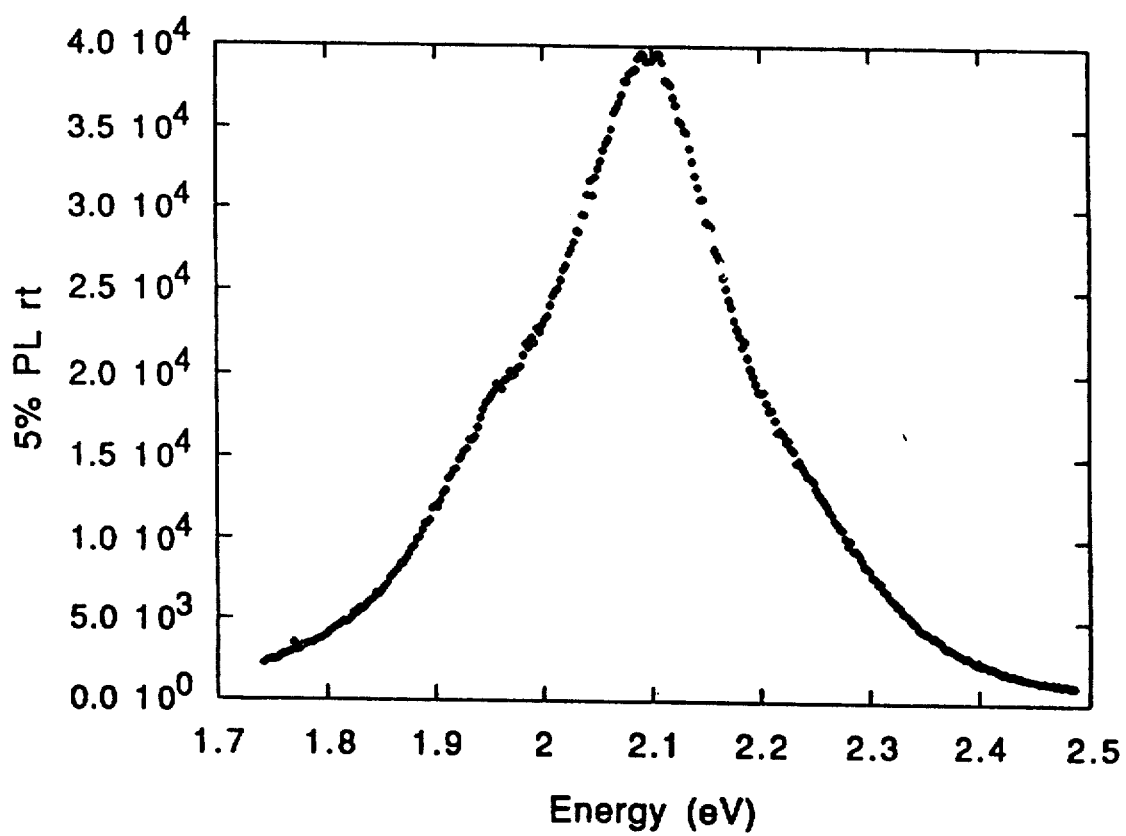

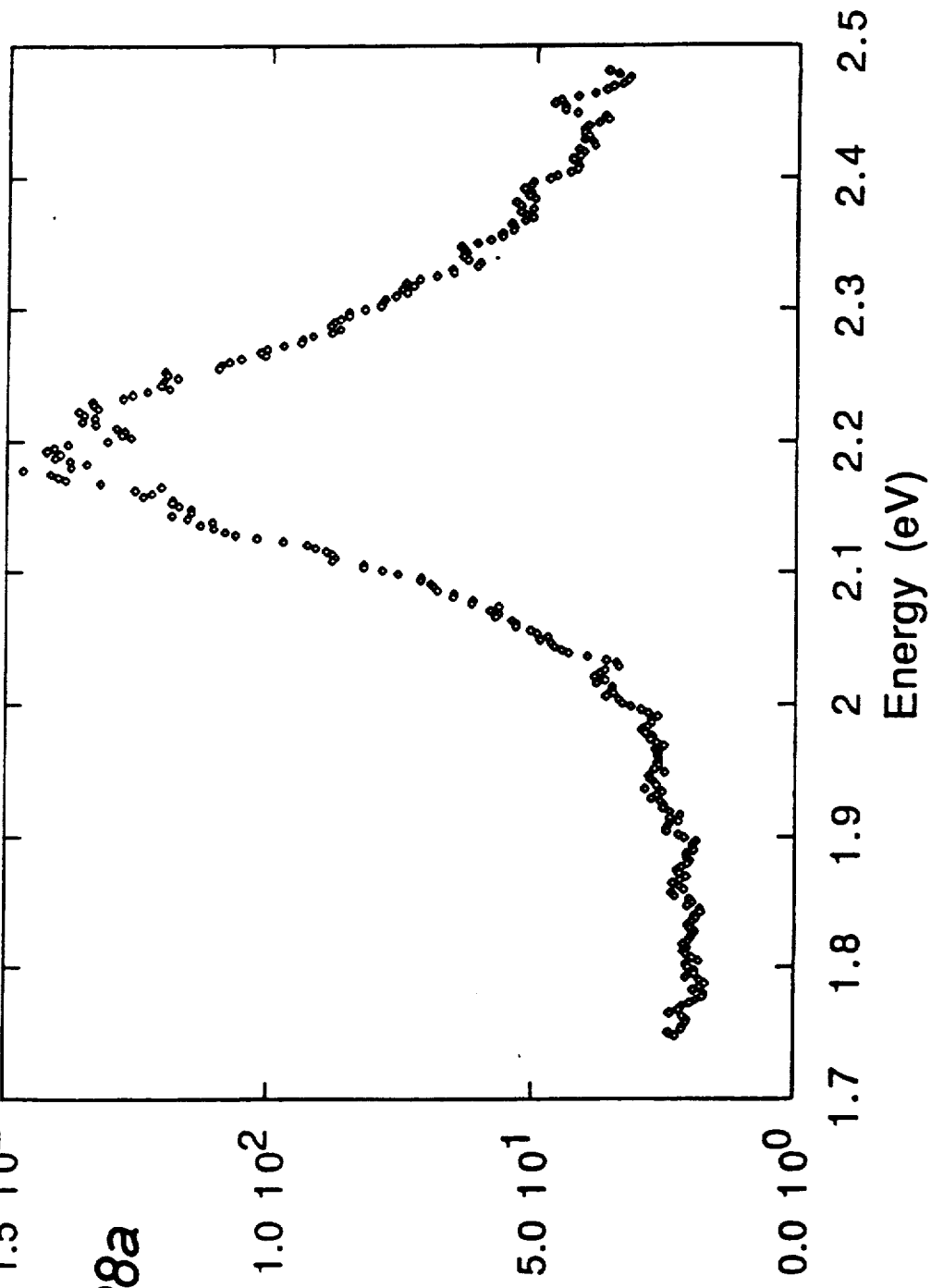

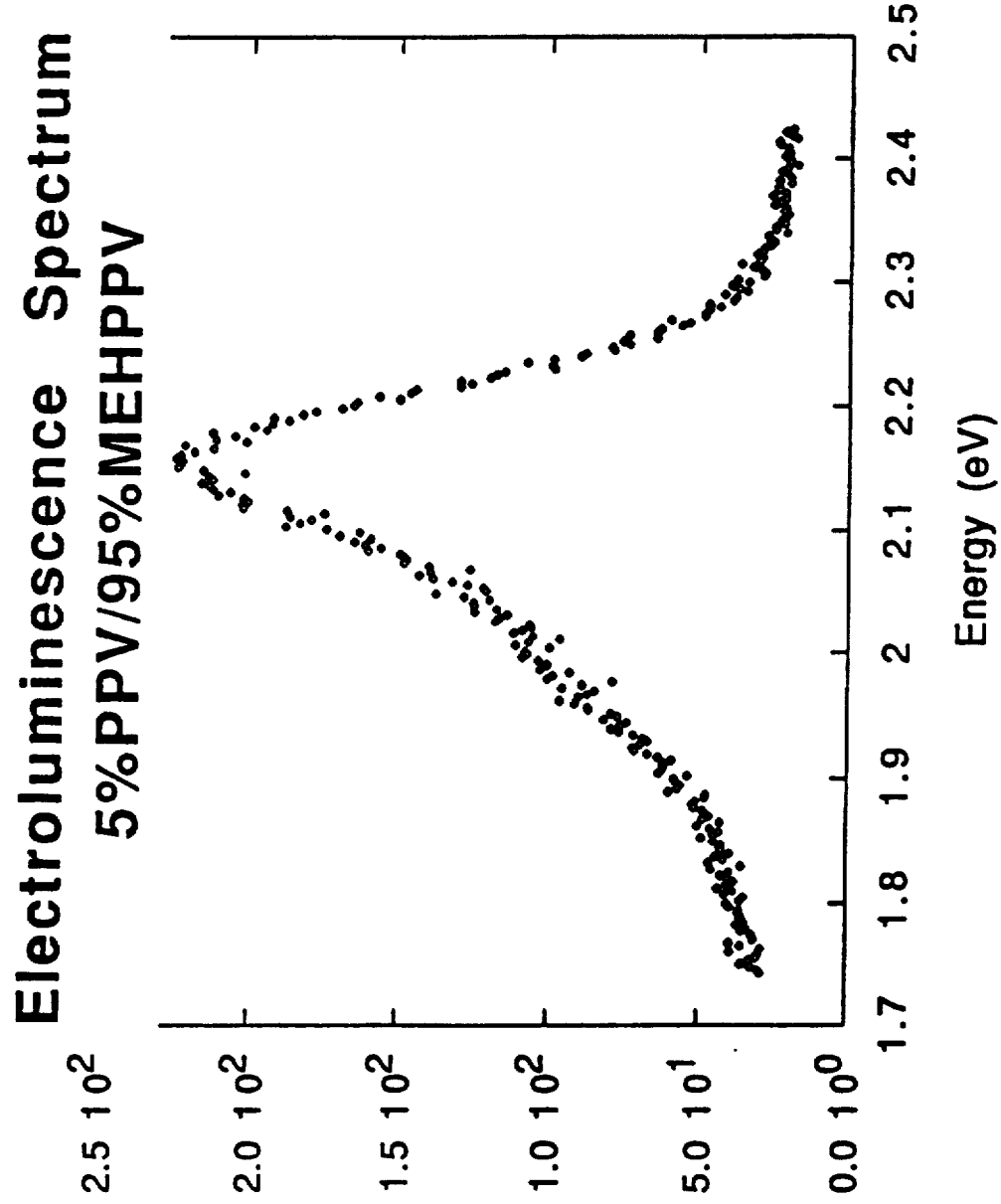
FIG. 28b Electroluminescence Spectrum 5%PPV/95%MEHPPV

DATA PRESENTATION Panel

Sample    20%
Run       b
Date      25-7-91

Bottom Contact                          ITO
Top Contact                             Al
Bottom Contact Thickness
Top Contact Thickness                   1000 Å

Electroluminescent Layer                20%ppv/80%mehppv
Electroluminescent Layer Thickness      800 Å

FIG. 32
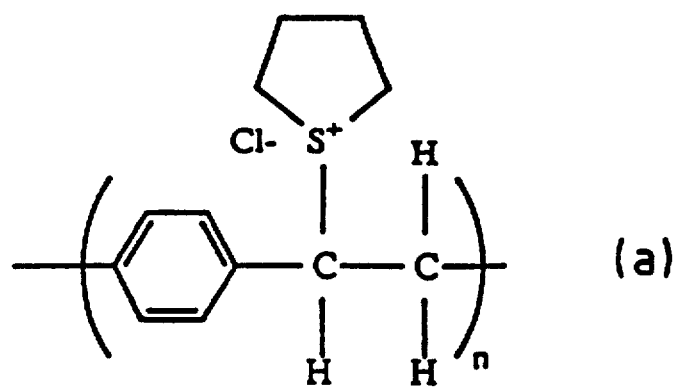
THT-leaving PPV Precursor
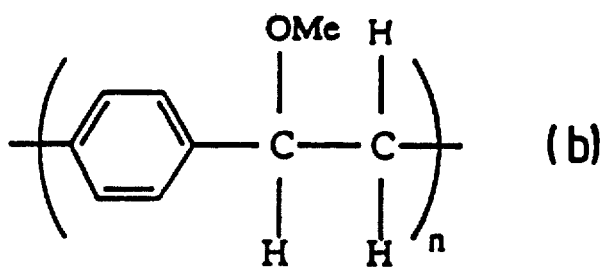
MeO-leaving PPV Precursor
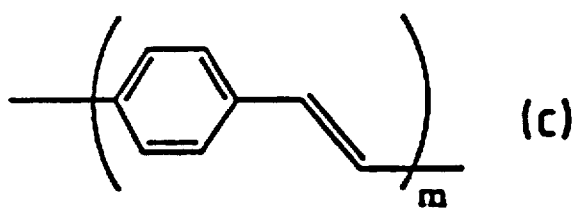
PPV
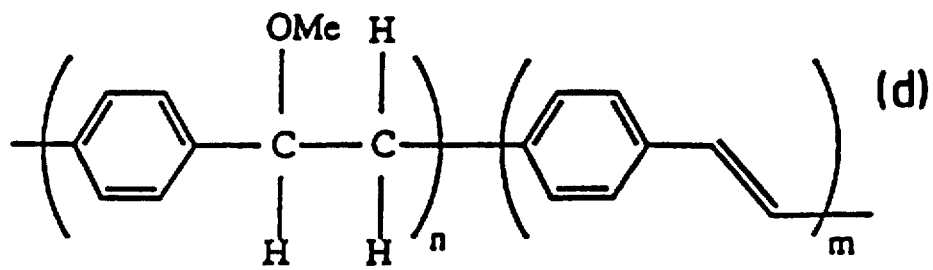
Partially converted MeO-leaving PPV RJ01-30 and RJ01-22 converted 300C in vacuo for 12h

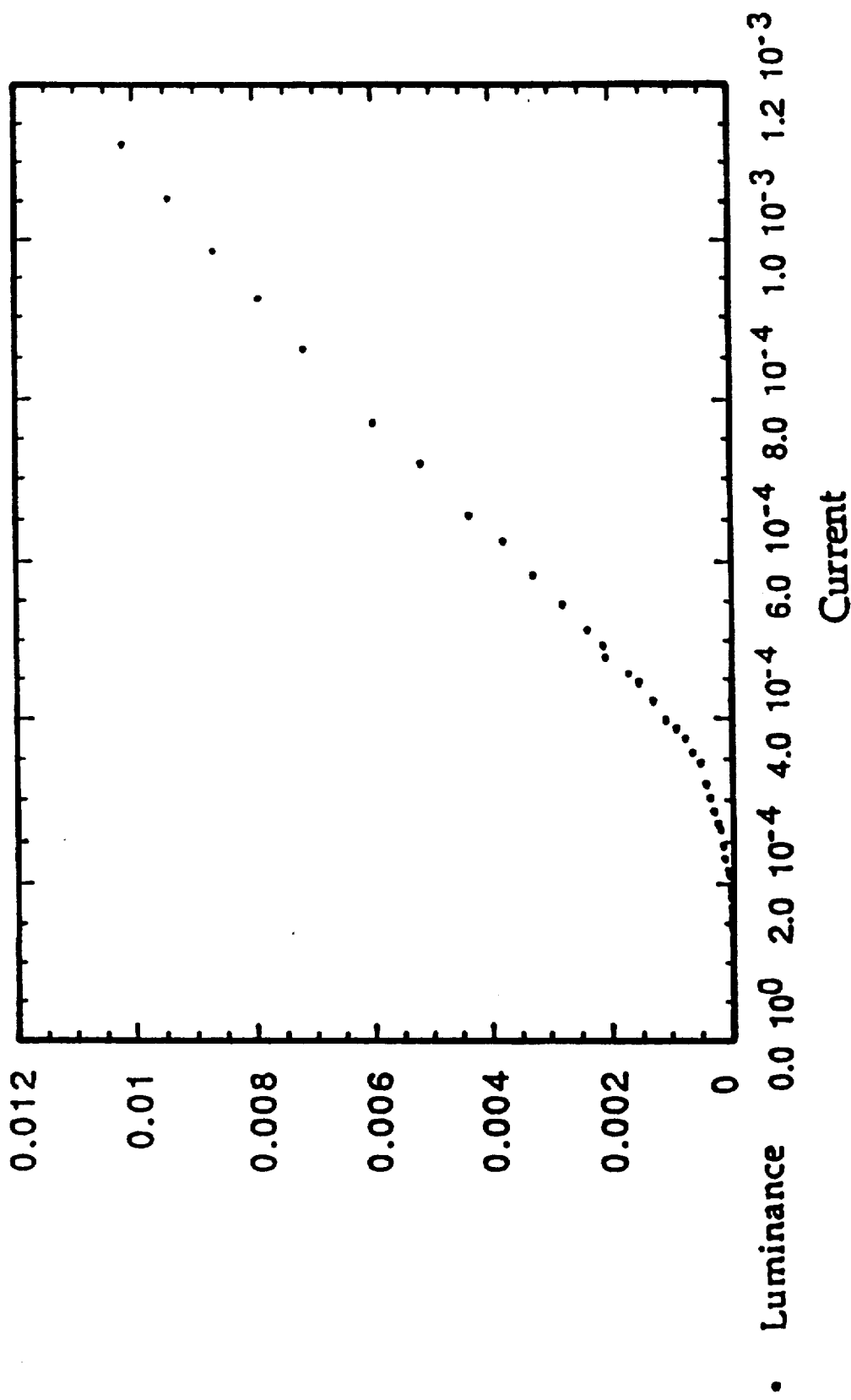
FIG. 37B  RJ01-30 Luminance/Current Characteristic

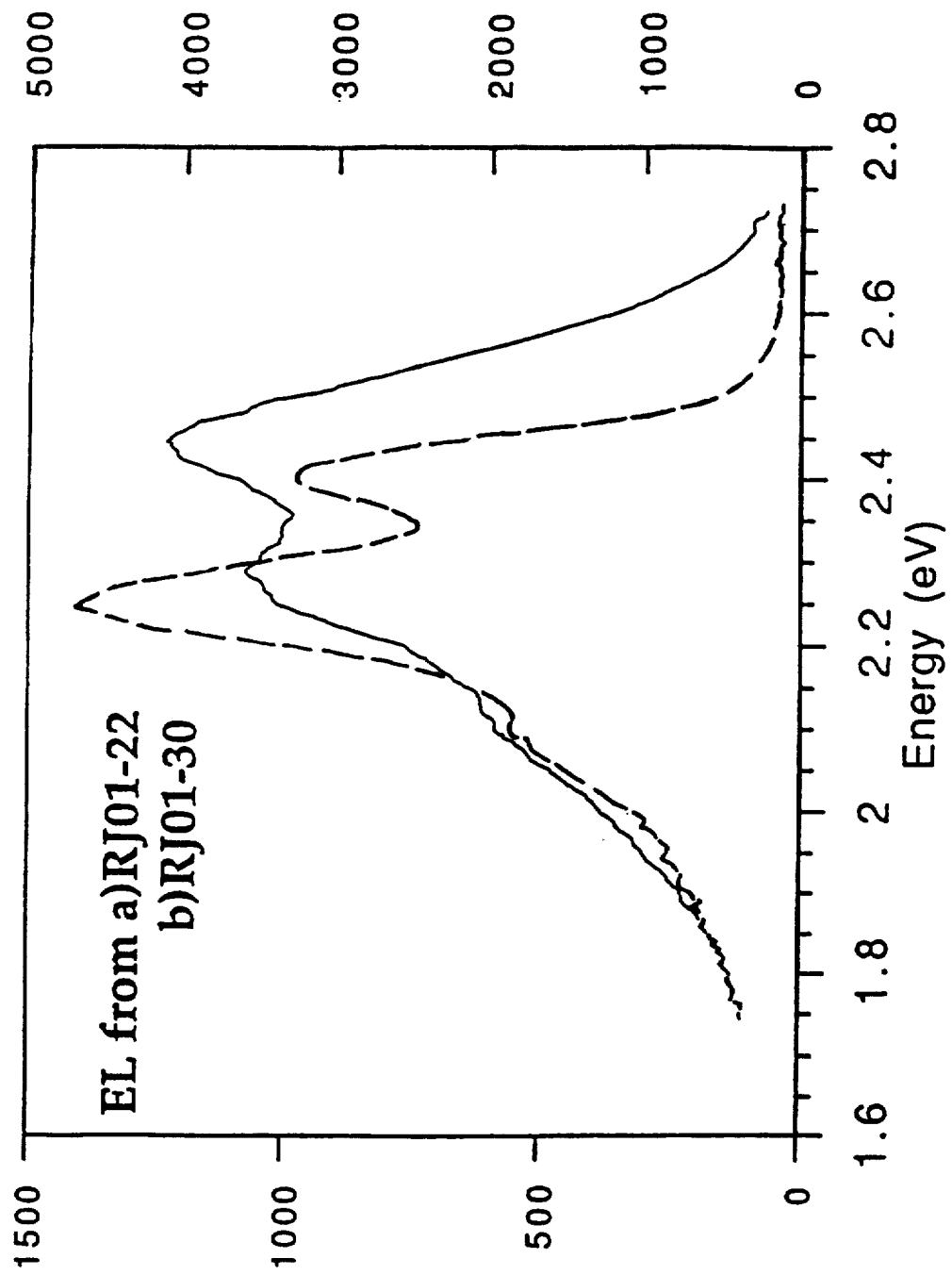

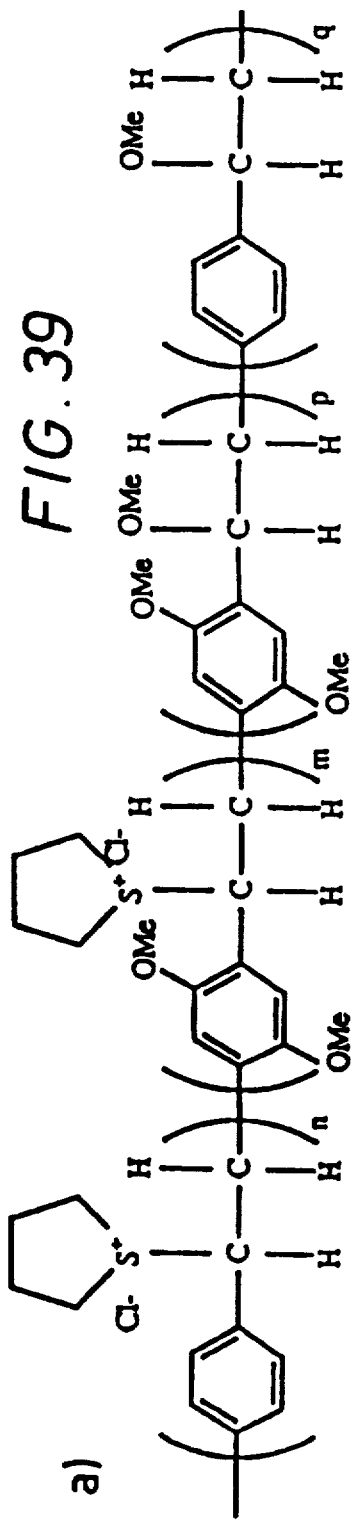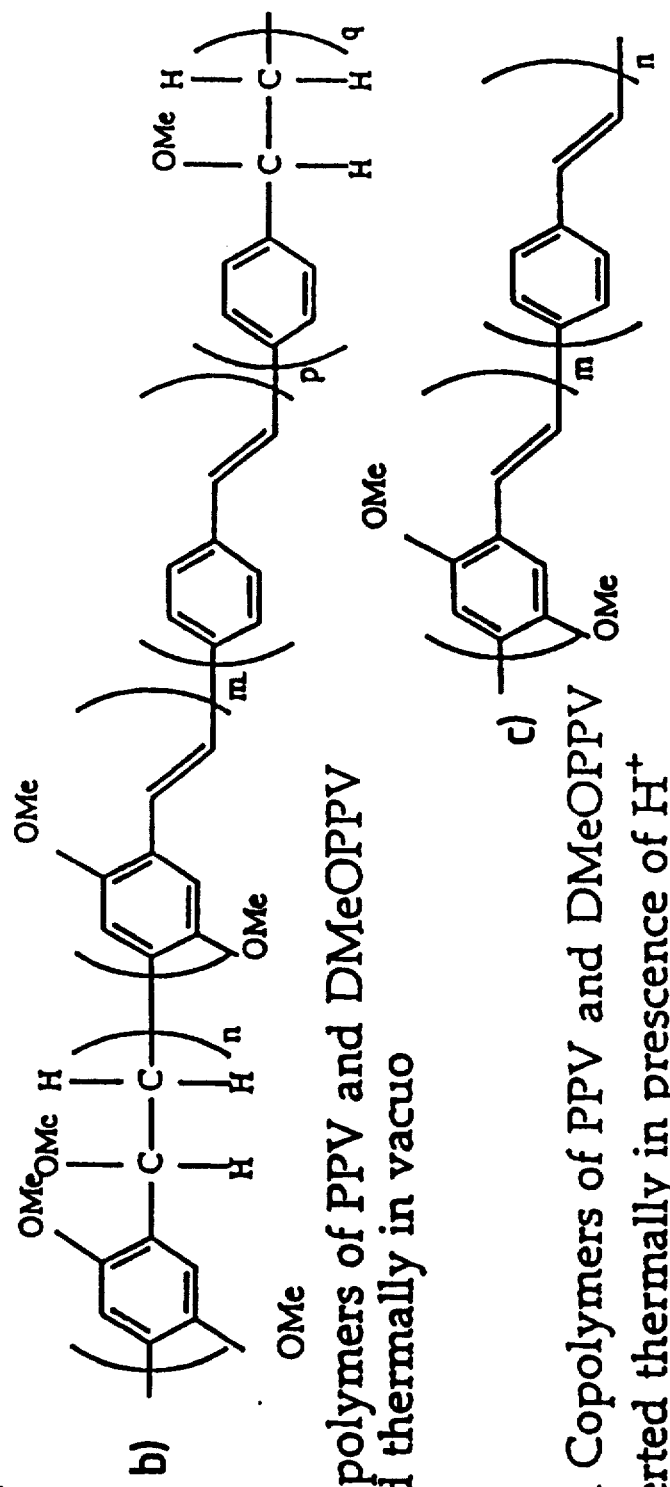
FIG. 39
a) Random Copolymers of PPV and DMeOPPV Precursor
b) Random Copolymers of PPV and DMeOPPV as converted thermally in vacuo
c) Random Copolymers of PPV and DMeOPPV as converted thermally in prescence of $H^+$ I.R. Absorption Spectra of the 20% Random Co-polymer of DMeOPPV and PPV
a) precursor (free-cast film)   b) spin-coated film on KBr disc converted at 220°C
   in vacuo for 2hrs   c) same sample further converted for 2hrs in Ar/HCl at 220°C

PATTERNING OF SEMICONDUCTIVE POLYMERS

FIELD OF THE INVENTION

This invention relates to patterning of semiconductive polymers to provide continuous polymer films having different regions of different characteristics.

BACKGROUND TO THE INVENTION

It has been shown that certain conjugated polymers show a relatively high quantum efficiency for the radiative decay of singlet excitons. Of these, poly-p-phenylene vinylene (PPV) can be prepared via a solution-processible precursor polymer, and although itself intractable and not easily processed, can be prepared in the form of thin films of high quality by thermal conversion of the as-prepared films of the precursor polymer. Details of this general synthesis method are given in "Precursor route poly(p-phenylene vinylene): polymer characterisation and control of electronic properties" D. D. C. Bradley, J. Phys. D: Applied Phys. 20, 1389 (1987), and "Spectroscopic and cyclic voltammetric studies of poly(p-phenylene vinylene) prepared from two different sulphonium salt precursor polymers" J. D. Stenger-Smith, R. W. Lenz and G. Wegner, Polymer 30, 1048 (1989). Measurements of photoluminescence, PL, have been reported by for example "Optical Investigations of Conjugated Polymers" R. H. Friend, J. Molecular Electronics, 4, 37 (1988), and "Photoexcitation in Conjugated Polymers" R. H. Friend, D. D. C. Bradley and P. D. Townsend, J. Phys. D 20, 1367 (1987). In our earlier International Patent Application No. PCT/GB90/00584 films of PPV are disclosed as being useful as the emissive layer in a structure exhibiting electroluminescence (EL). This structure requires injection of electrons and holes from either side of the active (i.e. emissive) region of the film, and various metallic contact layers can be used. In sandwich-like structures, and for emission from the plane of the device, one of these should be semi-transparent.

The advantages of using polymers of this type as the emissive layer in EL structures include:

(a) ease of fabrication of large area structures. Various methods are available for solution-processing of the precursor polymer, including spin-coating from solution which is the preferred method, and dip-coating;

(b) intractability of the polymer film, giving desirable strength, resistance to degradation from heat and exposure to oxygen, resistance to structural changes such as recrystallisation and shrinkage, and resistance to ion migration;

(c) intrinsically good properties for luminescence, including low densities of charges and/or spin-carrying defects.

However, a severe restriction has been placed on the use of such polymers by virtue of the fact that each continuous polymer film has the same characteristics throughout. That is, the quantum efficiency, wavelength of radiation and refractive index are the same over the whole surface of the film.

It is an object of the invention to provide a method of forming a polymer layer having different regions of different characteristics.

SUMMARY OF THE INVENTION

The present invention provides of forming in a semiconductive conjugated polymer at least first and second regions having different optical properties, the method comprising: forming a layer of a precursor polymer and permitting the first region to come into contact with a reactant and heat while permitting the second region to come into contact with a lower concentration of the reactant, the reactant affecting the conversion conditions of the precursor polymer in such a way as to control the optical properties of at least the first region so that the optical properties of the first region are different from those of the second region. The first and second regions are typically adjacent one another.

Advantageously, the precursor polymer comprises a poly(arylene-1,2-ethanediyl) polymer, at least some of the ethane groups of which include a modifier group whose susceptibility to elimination is increased in the presence of the reactant. Preferably, the reactant is an acid. The acid may be used which assists elimination of the modifier group. The acid may be added to the precursor polymer or may be endogenous to the precursor polymer, for example the acid evolved during formation of the precursor polymer. All that is required is that the first region comes into contact with the acid whereas the second region does not.

The modifier group should be stable at ambient temperatures and should preferably be stable to heat in the absence of the reactant. Typical modifier groups are discussed in more detail below.

Preferably the heating is carried out in the temperature range 100° to 300° C. The heating is preferably carried out for 1 to 24 hrs.

Preferably, the conjugated polymer is a copolymer comprising at least two different monomer units which in their individual homopolymer forms have different bandgaps. The proportion of monomer units in the copolymer may be selected to control the optical properties of the copolymer. By controlling the optical properties of the copolymer, the wavelength of radiation emitted during luminescence can be selected. The quantum efficiency of the copolymer may also be enhanced by controlling the optical properties. The refractive index of the copolymer may also be selected by controlling the optical properties thereof. Our copending application No. 07/748,777 describes and claims methods of modulating the semiconductor bandgap so as to control the optical properties of the copolymer.

A semiconductor is a material that is able to accommodate charged excitations which are able to move through this material in response to an applied electrical field. Charge excitations are stored in the semiconductor in states which are (or are derived from) conduction band states (in the language of quantum chemisty, lowest unoccupied molecular orbitals, LUMOs) if negatively charged, or valence band states (highest occupied molecular orbitals, HOMOs) if positively charged. The semiconductor band gap is the energy difference between valence and conduction bands (or from HOMO to LUMO).

The present application is primarily concerned with copolymers in which the material is made up of chemically distinct regions of polymer chain. A convenient description of the electronic states (molecular orbitals) is one in which the wavefunctions are substantially localised on a region of change of one chemical type. It is useful to define the semiconductor bandgap locally, i.e. as the energy gap between HOMO. and LUMO on a particular sequence of polymer chain to which the HOMO and LUMO wavefunctions are substantially confined. One can expect to find a variation of gap from HOMO to LUMO between regions of one chemical type and those of another. This may be described as a spatial modulation of the bandgap.

The conjugated polymers used here are all examples of semiconductors, and there is some control of bandgap through adjustment of the repeat units of the chain. However, it is also found that it is useful to incorporate some units of non-conjugated polymers to form some of the copolymers. In this case, the non-conjugated section of the chain would function as a very large gap semiconductor, so that under the conditions of operation found here it would behave as an insulator, i.e. there would be little or no charge storage on or movement through such a region of the chain. In this case, the material as a whole will still function as a semiconductor so long as there is a path through the bulk of the sample that passes entirely through the semiconducting regions of the chain (those that are conjugated). The threshold for the existence of such a path is termed the percolation threshold, and is usually found to be in the region of 20% volume fraction of non-insulating material. In the present specification, all such co-polymers are well above this percolation threshold and can be termed as semiconductors.

Quantum efficiency for luminescence may be defined as photons per electronic excited state. For photoluminescence this is identified as photons out per photon absorbed. For electroluminescence this is defined as photons out per electron injected into the structure.

A number of methods are available for causing the first region of the polymer to come into contact with the reactant and heat while premitting the second region to come into contact with a lower concentration of the reactant. In one embodiment, the step of permitting the first region to come into contact with the reactant comprises applying a coating in a desired pattern to the surface of the layer of the precursor polymer so as to leave unprotected portions of the surface. A reactant is applied to those unprotected portions. Alternatively, the reactant may be endogenous acid present in the layer of the precursor polymer. In this embodiment, the step of permitting the first region to come into contact with the reactant comprises trapping the acid during heating by a coating applied in a desired pattern to the surface of the layer of the precursor polymer. In either embodiment, the coating may be applied in the desired pattern by coating the surface of the layer of the precursor polymer with a layer of the coating. A layer of photoresist is applied to the layer of the coating and the layer of photoresist is activated so as to render the coating in the desired pattern protected by the photoresist. Any suitable photoresist may be used, such as one with optical or electron-beam sensitivity. The unprotected coating is removed, for example by etching and the remaining photoresist is also removed so as to leave the coating. In this way, the coating may be patterned with high resolution.

The particular material used to form the coating is not critical provided that it can be patterned on top of the layer of the precursor polymer without damaging the polymer underneath. The coating must be able to withstand the temperatures used in the heating and must also be subsequently removable without damaging the converted polymer. The preferred coating is aluminium although other metals may be usable as may some silicone-containing organic resists. An effective procedure is to apply a film of aluminium through a shadow mask so as to define a pattern. The aluminium is removable with dilute alkali such as sodium hydroxide. A polyimide coating may also be used.

The resolution achievable is set by the extent of acid diffusion from under the trapping layer. This will be close to the thickness of the layer of polymer. Typical resolutions are around 100 nm.

In a further aspect, the present invention provides a waveguide structure comprising at least first and second regions formed in a semiconductive polymer so as to have different optical properties from one another, the optical properties having been selected to control the refractive index of each region. The present invention also provides an electroluminescent device including a layer of polymer comprising at least first and second regions formed in a semiconductive polymer so as to have different optical properties bandgaps from one another, the optical properties having been selected to control the wavelength of radiation emitted by each region.

The position of the bandgap in the polymer materials described controls the refractive index below the bandgap. To simplest order, the refractive index is inversely proportional to the bandgap. Thus, patterning of the bandgap in the polymer layer permits the definition of structures in which there is a patterning of refractive index. By patterning the refractive index, fabrication of a wide range of guided-wave structures is enabled. In such structures, a waveguide is formed, for example, by a slab of high refractive index material surrounded by regions of low refractive index material. Such waveguides may be used in a passive role, to route optical signal around a circuit, or in an active role in devices in which the electro-optical or optical properties of the polymer are exploited. An example of such a device would be a laser diode with charge injection to form excited states in the region of the waveguide.

A large-area bit-mapped display is one type of electroluminescent device which may be fabricated from the polymers of the present invention. In such displays the control of colour permitted by controlling the optical properties of the polymers allows fabrication of multicolour displays. In such an application, a resolution of some 10 microns or so is likely to be adequate and this is well within the capability of the present invention.

Control of the optical properties of the copolymer may be achieved by varying the conversion conditions so that the conjugated copolymer retains some of the modifier groups so as to leave saturated a proportion of the vinylic groups of the copolymer. This has the effect of controlling the extent of conjugation of the copolymer so as to modulate the bandgap. In this embodiment, the heating conditions are controlled so as to control the extent of elimination of the modifier group. Advantageously, the precursor polymer comprises a homopolymer, preferably a poly(para-phenylene-1,2-ethanediyl) polymer, a poly(2,5 dimethoxy para-phenylene-1,2-ethanediyl) polymer, or a poly(thienylene-1,2-ethanediyl) polymer. Partial conversion of the precursor homopolymer yields a partially conjugated copolymer.

In a preferred embodiment, the semiconductive polymer comprises a conjugated poly(arylene vinylene) copolymer, wherein a proportion of the vinylic groups of the copolymer are saturated by inclusion of a modifier group substantially stable to elimination during formation of the film, whereby the proportion of saturated vinylic groups controls the extent of conjugation, thereby modulating the semiconductor ($\pi-\pi^*$) bandgap of the copolymer.

In this aspect of the invention, the precursor polymer is formed whereby substantially all the leaving groups are replaced by the modifier groups. A suitable method for forming the pre-cursor polymer is to be found in Tokito et al Polymer (1990), vol. 31, P.1137. By replacing the leaving group with a modifier group which is substantially stable at ambient temperatures, a relatively robust precursor polymer is formed. Examples of typical modifier groups are set out in the following discussion. Advantageously the modifier group is an alkoxy group, preferably a methoxy group.

By controlling the extent of conversion to the copolymer, the extent of conjugation in the copolymer is controlled. Where the heating of the precursor polymer is carried out in the presence of acid this tends to result in conversion to the fully conjugated polymer. By controlling the temperature of heating and the time of heating it is possible to control the degree of conversion into the copolymer, thereby modulating the semiconductor bandgap of the copolymer. Thus, the wavelengths of radiation emitted during luminescence of the material may be selected by controlling the heating conditions. The more conversion to the conjugated copolymer, the more red-shifted the wavelength becomes. The colour of the emissions from blue to red can be controlled in this way. Preferably, the temperature of heating is in the range 200°–300° C. and preferably the heating time is up to 12 hours.

In a further embodiment, the precursor polymer comprises a poly(arylene-1,2-ethanediyl) precursor copolymer wherein a proportion of the ethane groups include the modifier group substituent and at least some of the remaining ethane groups include a leaving group substituent, whereby elimination of the leaving group substituents occurs upon heating substantially without elimination of the modifier group substituents so as to form the conjugated poly(arylene vinylene) copolymer.

The present invention utilizes the feature that the extent of conjugation of conjugated poly(arylene vinylene) copolymers can be tailored by appropriate selection of the arylene constituents of the copolymer and of the modifier group. For example, phenylene moieties incorporating electron-donating substituent groups or arylene moieties with oxidation potentials lower in energy than that of phenylene are found to incorporate the modifier group preferentially as compared with the corresponding unsubstituted arylene moiety. Thus, the proportion of vinylic groups saturated by incorporation of the modifier group can be controlled by selection of the arylene moieties substituents and the extent of conjugation of the copolymer may be concomitantly modulated. The extent of conjugation of the copolymer affects the $\pi-\pi^*$ bandgap of the copolymer. Therefore, selection of appropriate reaction components may be used to modulate the bandgap in different regions of the polymer layer.

Thus, the invention contemplates a method of conversion of the precursor into its copolymer in which the extent of elimination of the leaving group constituents is controlled in different regions to control the colours of luminescence of the resulting copolymer film.

In a further aspect, there is provided a method of forming a poly(arylene-1,2-ethanediyl) precursor copolymer as defined above, which method comprises reacting a first monomer component with a second monomer component, in the presence of base and a solvent comprising a modifier group, wherein the first monomer component comprises a first arylene moiety substituted with —$CH_2L^1$ and —$CH_2L^2$ and the second monomer component comprises a second arylene moiety substituted with —$CH_2L^3$ and —$CH_2L^4$, in which $L^1$, $L^2$, $L^3$ and $L^4$ each represents a leaving group substituent which may be the same or different from one another. This method may constitute a first step in the formation of a partially conjugated poly(arylene vinylene) copolymer.

A function of the modifier group is to interrupt the conjugation of the poly(arylene vinylene) copolymer by saturation of the vinylic groups of the copolymer chain. Thus, for the modifier group to be successful in this function it must be relatively stable to elimination during formation of the poly(arylene vinylene) copolymer. Typical modifier groups include:

RO—,
RS—,
ArO—,
ArS—,
NC—,

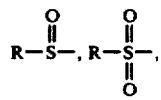

RSe—,
HO—.

A preferred modifier group is a $C_1$ to $C_6$ alkoxy group, more preferably a methoxy group.

The poly(arylene-1,2-ethanediyl) precursor copolymer may be formed in a first step by reacting a first monomer component with a second monomer component, in the presence of base and a solvent comprising the modifier group, wherein the first monomer component comprises a first arylene moiety substituted with —$CH_2L^1$ and —$CH_2L^2$ and the second monomer component comprises a second arylene moiety substituted with —$CH_2L^3$ and —$CH_2L^4$ in which $L^1$, $L^2$, $L^3$ and $L^4$ each represents a leaving group substituent which may be the same or different from one another.

In the step of forming the poly(arylene-1,2-ethanediyl) precursor copolymer the solvent preferably also includes water. Thus, for aqueous solvents, the modifier group must be present as a water miscible polar solvent/reagent. Where the modifier group is alkoxy, the corresponding solvent or solvent component would therefore be an alcohol. Preferably the solvent comprises at least 30% modifier group by weight. More preferably the solvent is water: methanol at a ratio of 1:1. Modifier groups may be introduced selectively either during formation of the precursor copolymer or by displacement reactions on the precursor copolymer.

The identity of the leaving groups is not particularly critical provided that the first and second monomer components may react together in the presence of base and provided that the leaving group substituents on the poly(arylene-1,2-ethanediyl) precursor copolymer may eliminate upon heating. Typical leaving groups include 'onium salts in general, bearing a non-basic counter anion. Sulphonium salts, halides, sulphonates, phosphates or esters are suitable. Preferably a sulphonium salt such as a tetrahydrothiophenium salt is used.

Throughout this specification the term arylene is intended to include in its scope all types of arylenes including heteroarylenes as well as arylenes incorporating more than one ring structure, including fused ring structures.

At least two arylene moieties are present in the copolymer chain and these may be substituted or unsubstituted arylene or heteroarylene moieties. Suitable substituents include alkyl, O-alkyl, S-alkyl, O-aryl, S-aryl, halogen, alkyl sulphonyl and aryl sulphonyl. Preferred substituents include methyl, methoxy, methyl sulphonyl and bromo, and the arylenes should preferably be substituted symmetrically. In a more preferred embodiment of the invention, one of the arylene moieties of the copolymer is unsubstituted and comprises para-phenylene. Preferably, the second component is selected from the group comprising 2,5-dimethoxy-para-phenylene, 2,5-thienylene and 2,5-dimethyl-para-phenylene. More preferably the para-phenylene moiety is present in the copolymer chain in an amount resulting from conversion of a precursor copolymer formed by reaction of at least 70 mole % of the PPV precursor monomer unit.

Referring in particular to the method of forming the conjugated polyarylene vinylene copolymer, this is effected by heating, preferably in a temperature range of 70°-300° C. The heating is performed substantially in the absence of oxygen, for example under an inert atmosphere such as that of one or more inert gases or under vacuum.

In the step of forming the precursor copolymer, a range of reaction temperatures and reaction times is possible. The reaction temperature is constrained mainly by the temperature range at which the solvent is liquid and typically varies from −30° C. to +70° C. preferably −30° C. to +30° C., more preferably −5° C. to +10° C. The reaction time may typically be between 1 minute and 1 day, depending on the temperature and reaction components, preferably not greater than 4 hours. Once the precursor copolymer is formed this may optionally be purified, for example by precipitation with a salt of a non-nucleophilic counter anion (i.e. anion exchange). Preferably the precursor copolymer is dialysed against an appropriate solvent such as water or a water-alcohol mixture.

Choice of the base used in the reaction is not particularly critical provided that it is soluble in the solvent. Typical bases include hydroxides or alkoxide derivatives of Group I/II metals and may be present at a ratio of 0.7-1.3 mole equivalents of base per mole of monomer. Preferably, hydroxides of lithium, sodium or potassium are used in equimolar proportions with the monomer.

In a further embodiment, at least one of the monomer units of the copolymer comprises an arylene vinylene unit substituted with a solubilizing group in the arylene ring so as to render the copolymer soluble. Any known solubilizing group may be used for this purpose. Where the copolymer is to be soluble in water, a charged solubilizing group is preferred. The solubilizing group typically comprises an alkoxy group of at least 4 carbon atoms. The alkoxy group may be branched or linear and preferably introduces asymmetry into the arylene rings so as to disrupt the packing of the copolymer chains. Preferably the alkoxy group is a 2-methylpentyloxy or a 2-ethylhexyloxy group. A further alkoxy group such as a methoxy group may be substituted para to the solubilizing group.

By making the copolymer soluble, this confers the advantage of allowing the copolymer to be processed in solution.

In the following when reference is made to ratios of PPV, dimethoxy-PPV, PTV and dimethyl-PPV monomer units in both precursor and conjugated copolymer structures the ratios are defined by the amounts of the corresponding monomer units used in the initial polymerisation reaction.

For a better understanding of the present invention and to show how the same may be carried into effect, reference will now be made by way of example to the accompanying drawings.

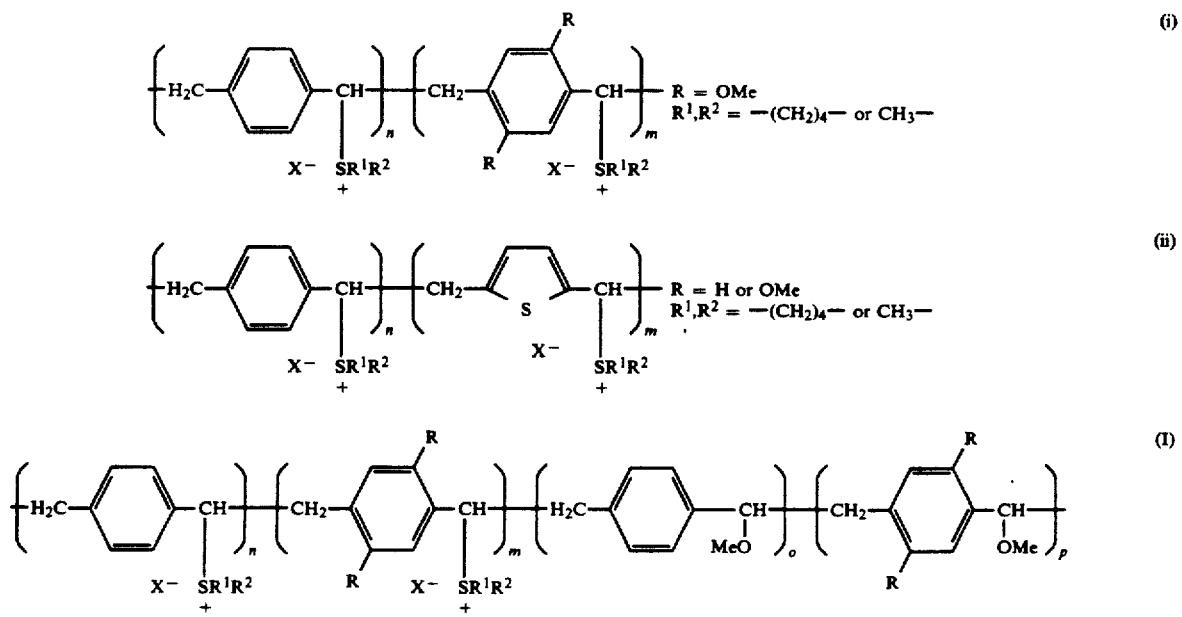

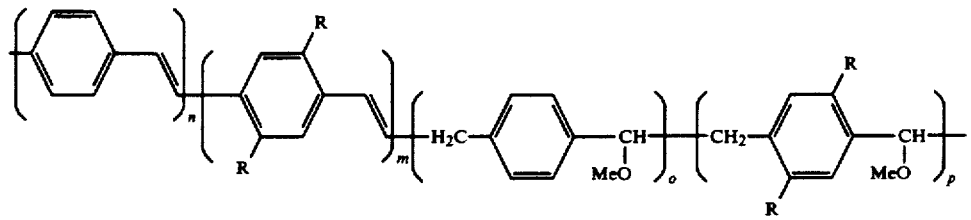

(II)

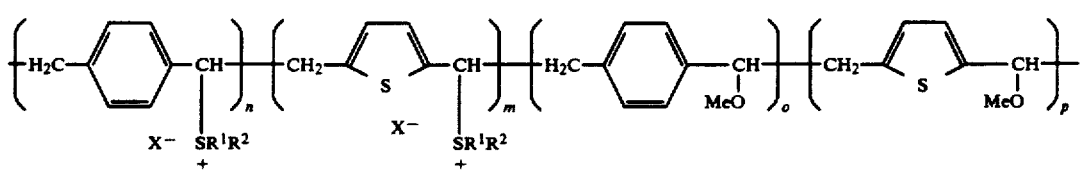

(III)

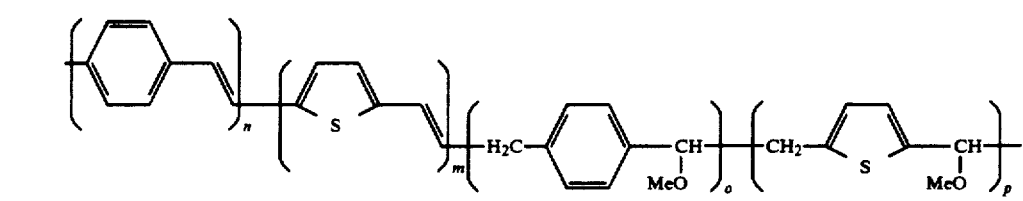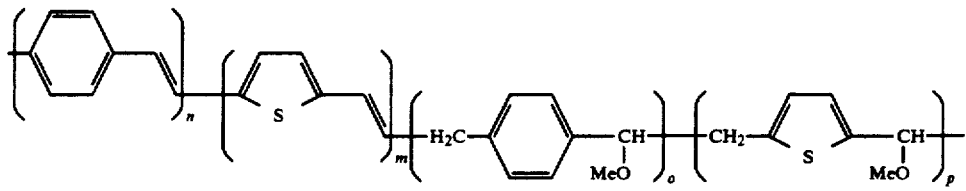

(IV)

BRIEF DESCRIPTION OF THE DRAWINGS

FIG. 2a is a graph showing the absorption spectra of spin-coated thin films of PPV and copolymers of PPV, as the majority constituent, and dimethoxy-PPV (DMeOPPV) as converted at 220° C. in vacuo for 2 hours Curve a is PPV homopolymer
Curve b is 95% PPV to 5% DMeOPPV
Curve c is 90% PPV to 10% DMeOPPV
Curve d is 85% PPV to 15% DMeOPPV
Curve e is 80% PPV to 20% DMeOPPV
Curve f is 70% PPV to 30% DMeOPPV FIG. 2b is a graph showing the absorption spectrum of a spin-coated thin film of dimethoxy-PPV as converted at 220° C. in the present of acid for two hours;

FIGS. 10b, 11b and 12b are graphs showing the luminescence/current relationship for a thin film of respectively PPV; a copolymer produced from a 9:1 molar ratio of PPV and dimethoxy PPV monomer units respectively; and a copolymer produced from a 9:1 molar ratio of PPV and thienylene vinylene monomer units respectively, the polymer films being spin-coated and converted at 220° C. for two hours in vacuo with hole injecting electrodes of oxidised aluminium, and with electron injecting electrodes of aluminium;

A film of copolymer of 10% DMeOPPV: 90% PPV was spin-coated and an area was capped with 500A of evaporated aluminium. The sample was then thermally converted for 12 hours at 220° C. in vacuo. The aluminium capping layer was removed by reacting it in dilute alkali. FIGS. 16 and 17 show the optical absorption spectra and photoluminescent spectra for two areas in a polymer film which have undergone different conversion treatments;

FIGS. 27a and 27b are graphs showing the photoluminescence emission spectra of random copolymers of PPV and MEH-PPV produced from 20:80 and 5:95 w/w ratios of PPV and MEH-PPV monomer units, respectively;

FIGS. 28a and 28b are graphs showing the electroluminescence spectra for random copolymers of PPV and MEH-PPV produced from 20:80 and 5:95 w/w ratios of PPV and MEH-PPV monomer units, respectively;

FIGS. 32 (a to d) show respectively the formal structural formulae of: the THT-leaving PPV precursor; the MeO-leaving PPV precursor; PPV; and partially converted MeO-leaving PPV;

FIG. 38 is a graph showing the electroluminescence emission spectra of THT-leaving PPV (dotted) and MeO-leaving PPV (solid) after thermal conversion;

FIG. 39 show respectively the focal structural formulae of the random copolymers of: PPV and DMeOPPV in precursor form; as converted thermally in vacuo; and as converted thermally in the presence of acid;

FIG. 41 is a graph showing the infra red absorption spectra of a 20% random copolymer of DMeOPPV and PPV in which:

Figure 42:
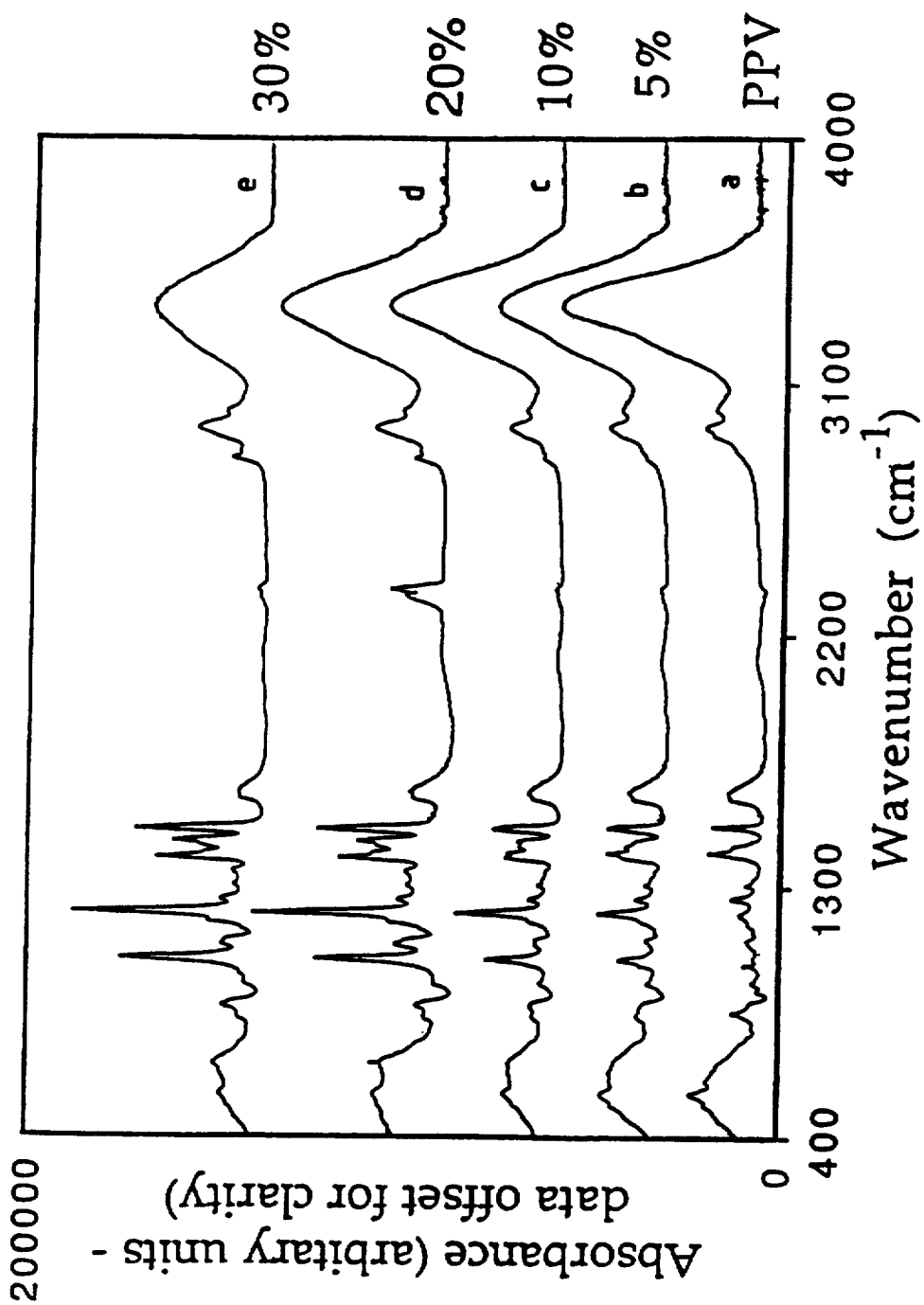
Figure 43:
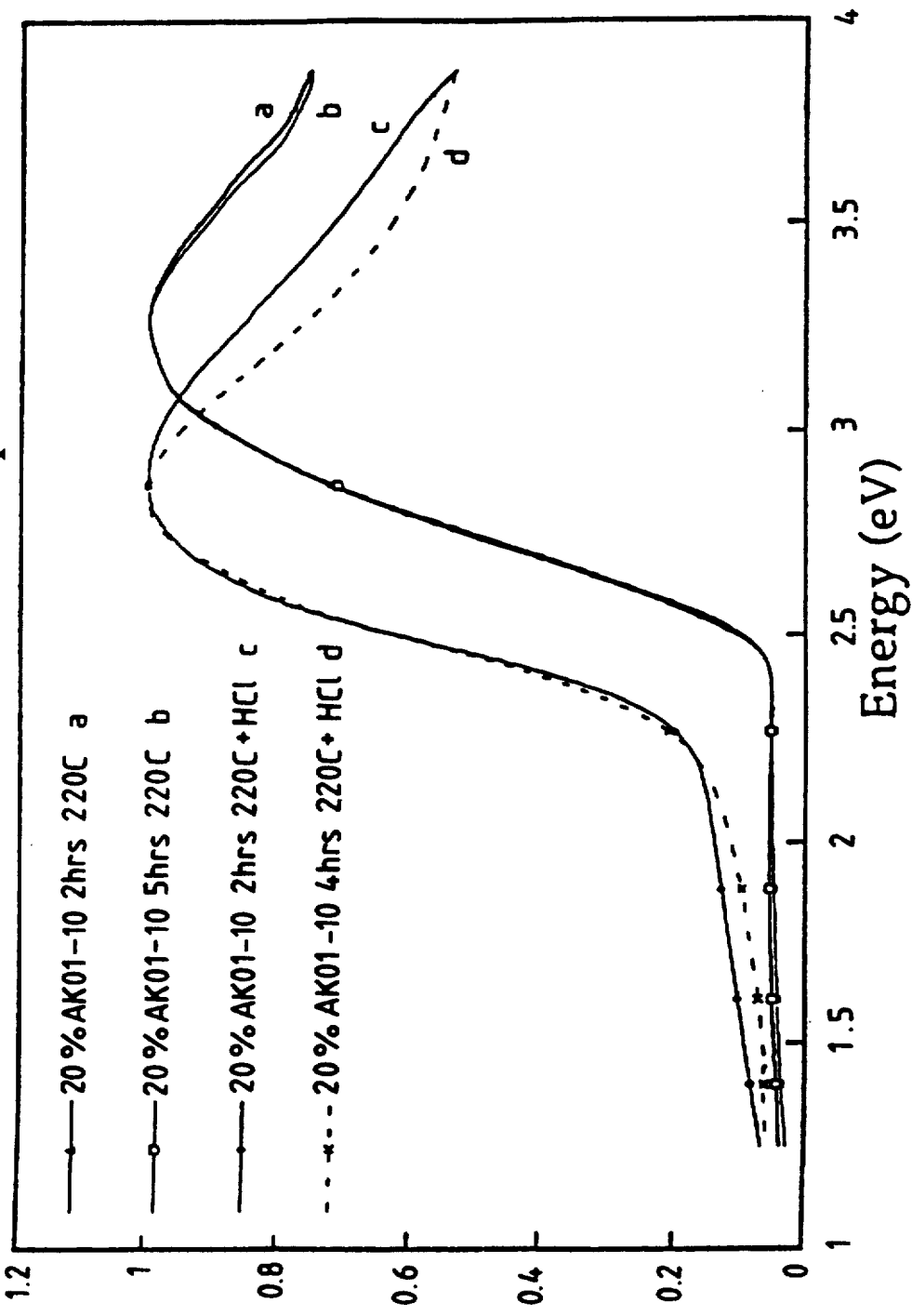
Figure 44:
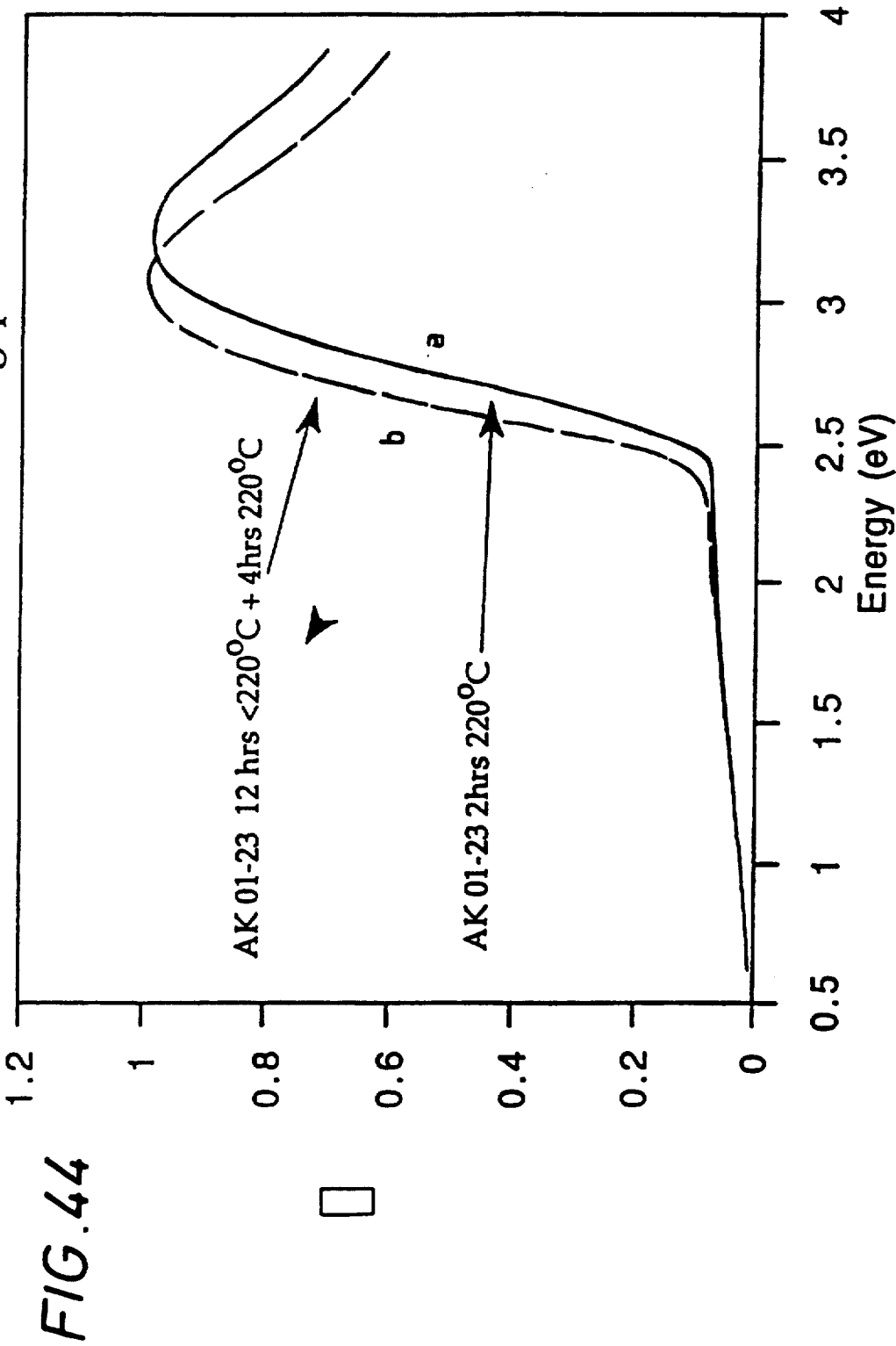
Figure 45:
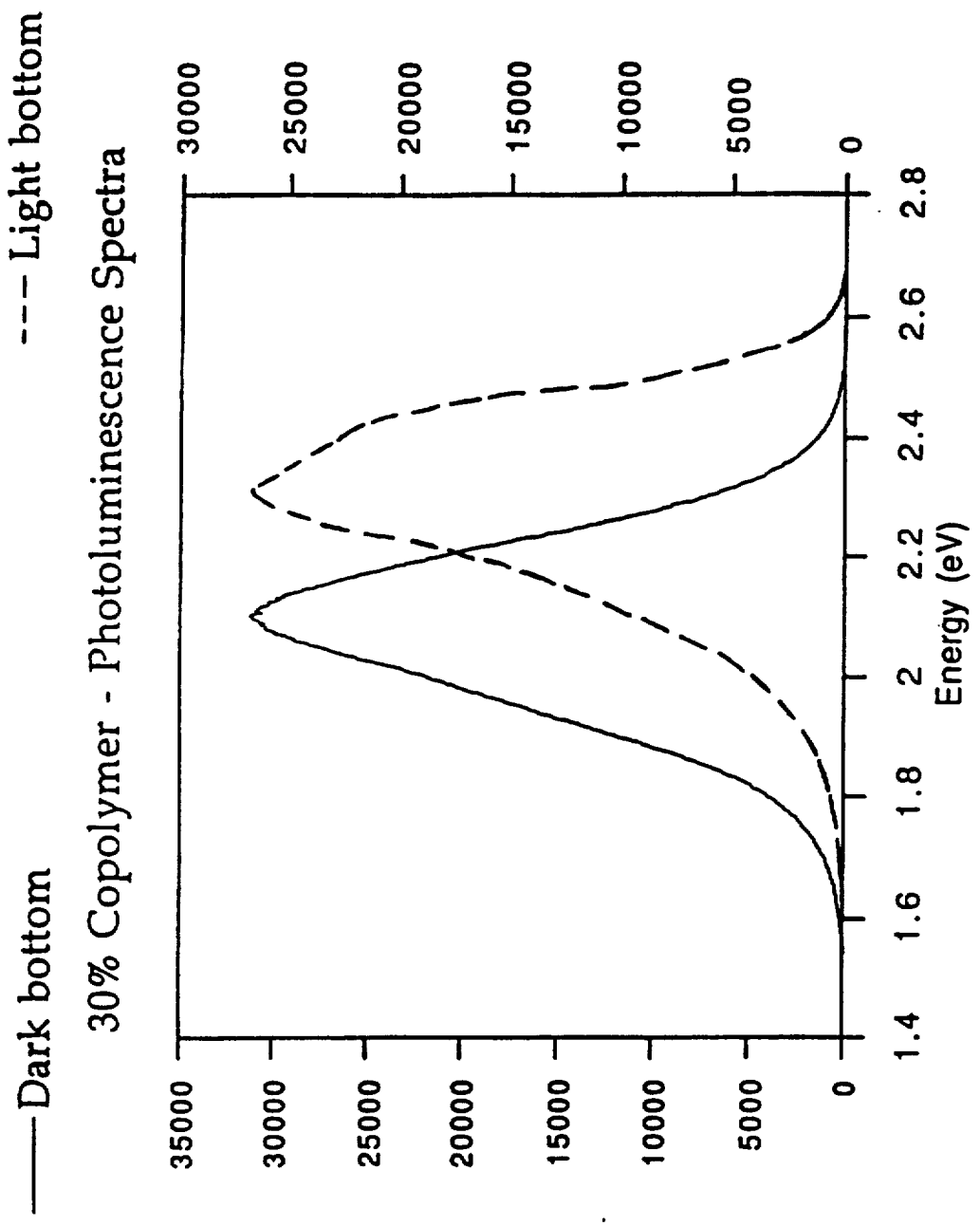
Figure 46:
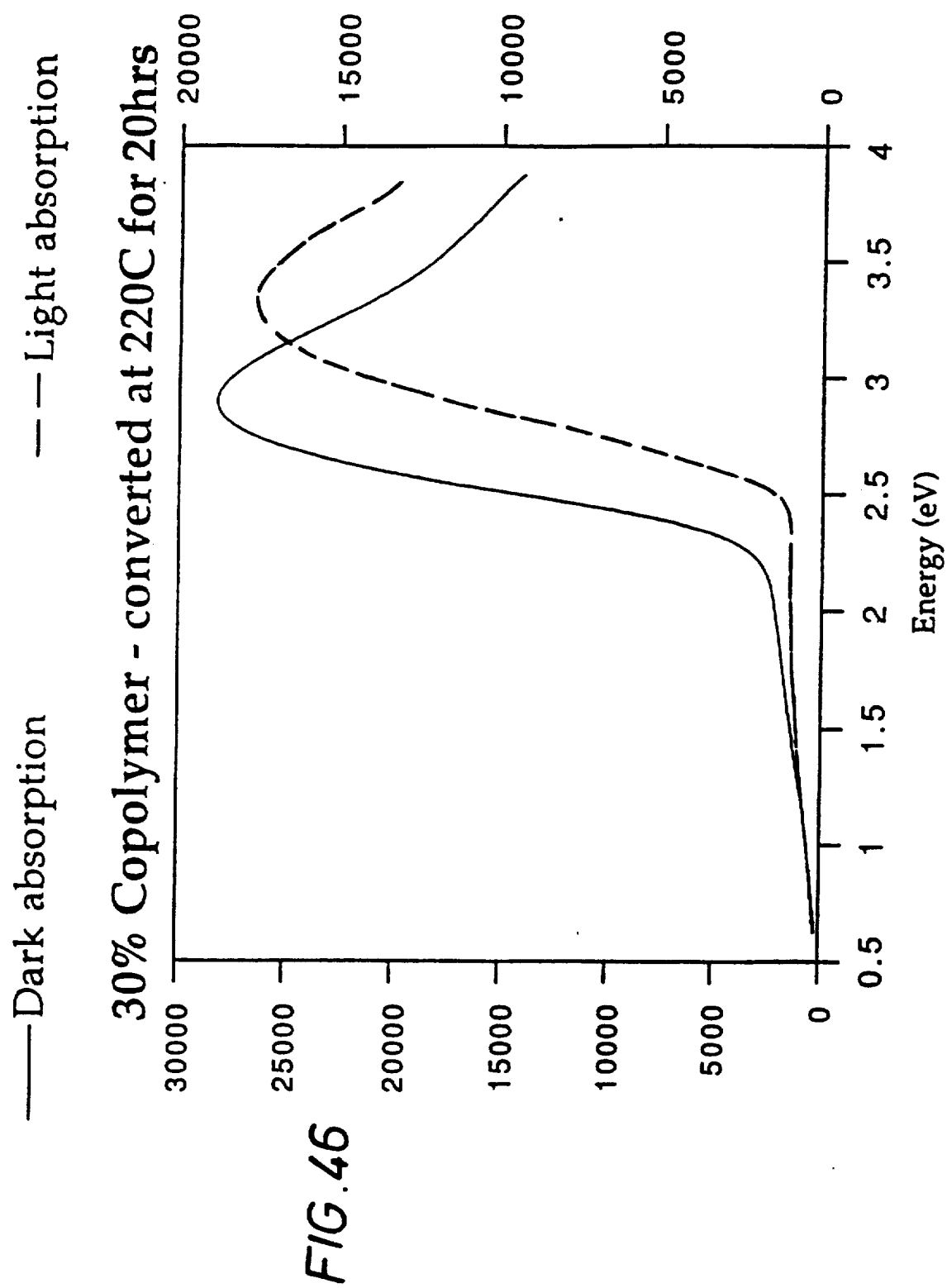
Figure 47:
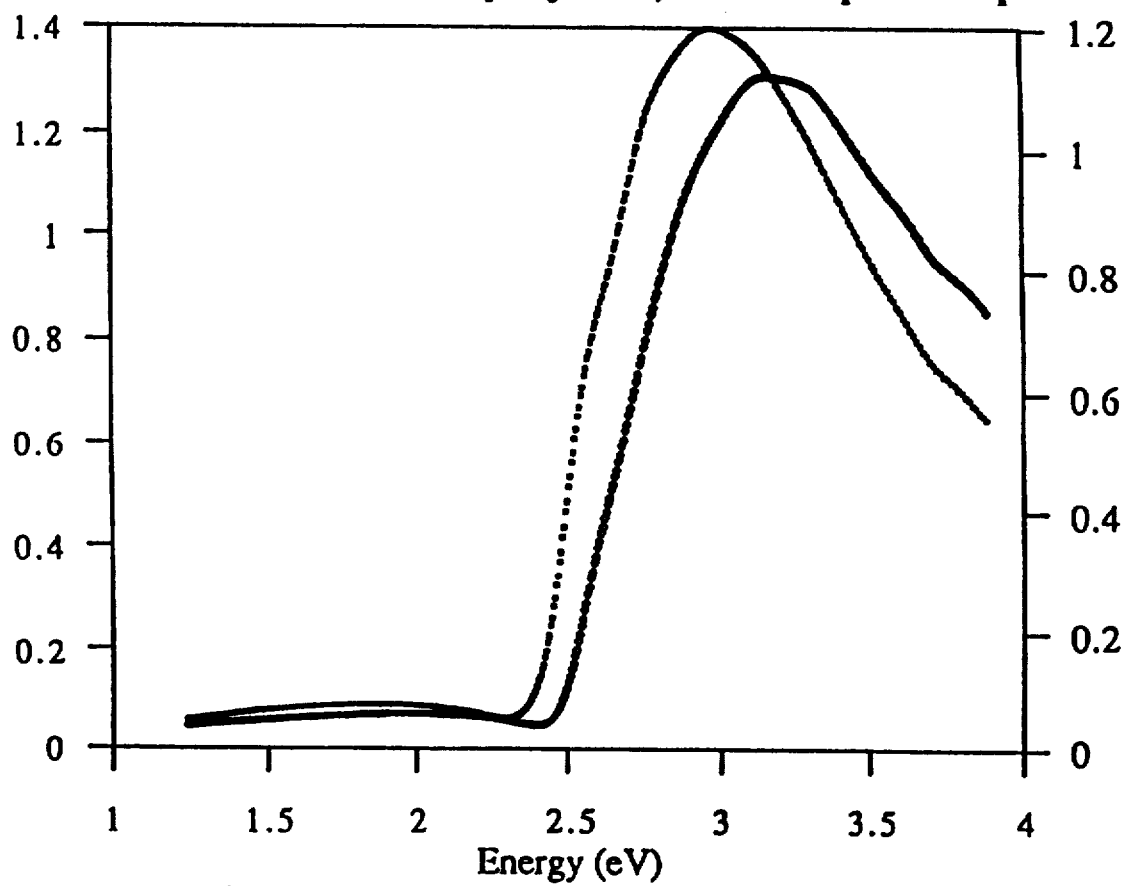
Figure 48:
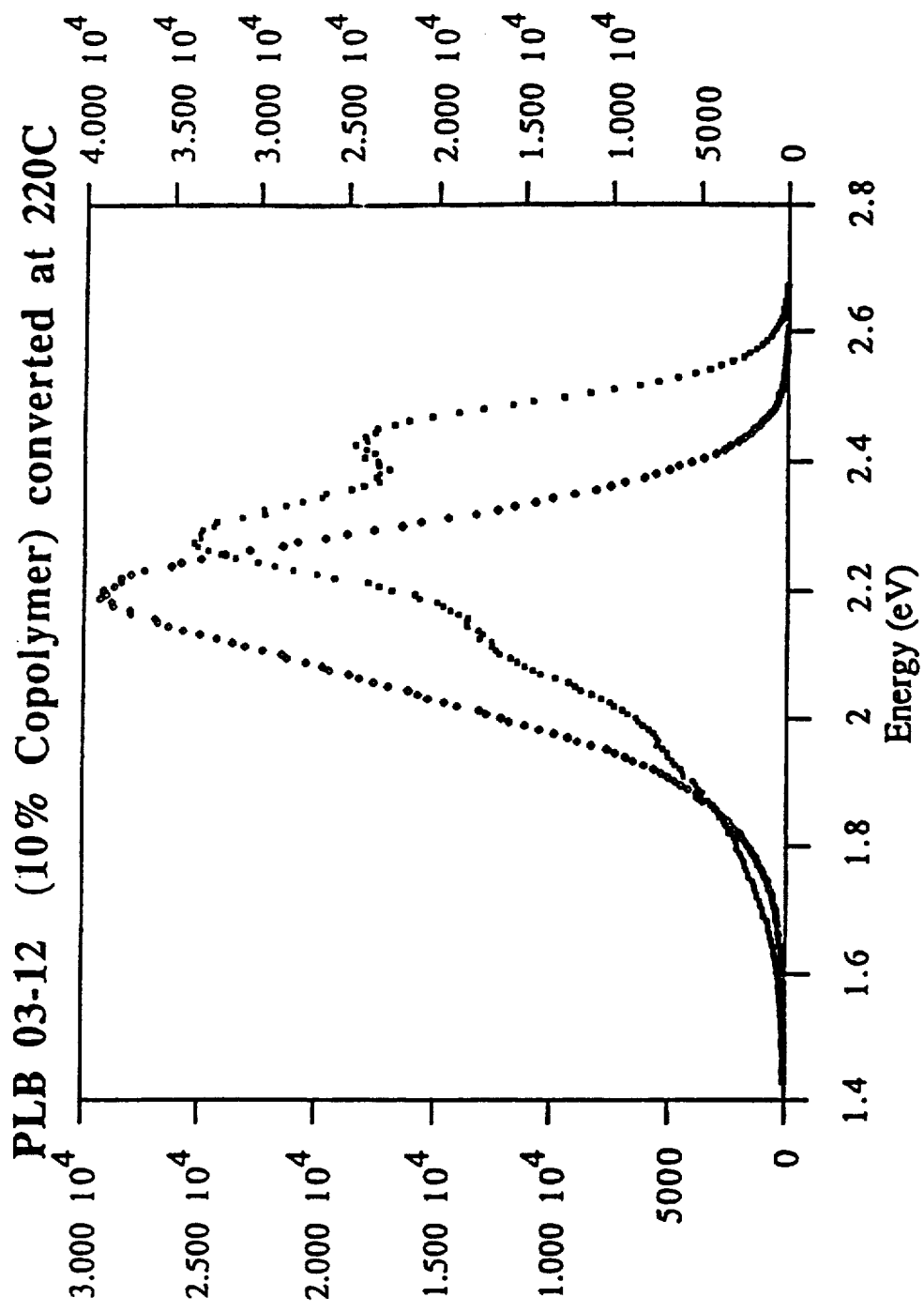

(a) is the precursor (b) is the copolymer spin-coated on KBr and converted at 220° in vacuo for two hours (c) is the same sample further converted for two hours at 220° C. in the presence of acid;

FIG. 42 are graphs showing respectively the infrared absorption spectra of PPV (a) and the random copolymers of PPV, as the major constituent, and DMeOPPV produced from 95:5 (b), 90:10 (c), 80:20 (d) and 70:30 (e) molar ratios of PPV and DMeOPPV monomer units respectively;

FIG. 43 is a graph showing the absorption spectra of spin-coated thin films of a 20% random copolymer of DMeOPPV and PPV converted in vacuo (a,b) and in the presence of HCl (c,d);

FIG. 44 is a graph showing the variation of bandgap with different conversion conditions; the higher bandgap material (a) converted for 2 hours at 220° C. in vacuo, the lower bandgap material (b) converted for 12 hours at 100° C. in vacuo and subsequently four hours at 220° C. in a 15% random copolymer of DMeOPPV and PPV;

FIG. 45 is a graph showing the photoluminescence spectra of a 30% random copolymer of DMeOPPV and PPV;

FIG. 46 is a graph showing the photoluminescence emision spectra of a 30% random copolymer of DMeOPPV and PPV;

FIG. 47 is a graph showing the absorption spectra of capped and uncapped 10% random copolymers of DMeOPPV and PPV; and FIG. 48 is a graph showing the photoluminescence emission spectra of capped and uncapped 10% random copolymers of DMeOPPV and PPV after thermal conversion.

In each of FIGS. 45 to 48, a film of copolymer were spin-coated and an area was capped with 500A of evaporated aluminium. The sample was then thermally converted for 12 hours at 220° C. in vacuo. The aluminium capping layer was removed by dissolving it in dilute alkali. The lower energy absorption and photoluminescence spectra are from the capped regions of polymer.

DESCRIPTION OF THE PREFERRED EMBODIMENTS

Figure 1:
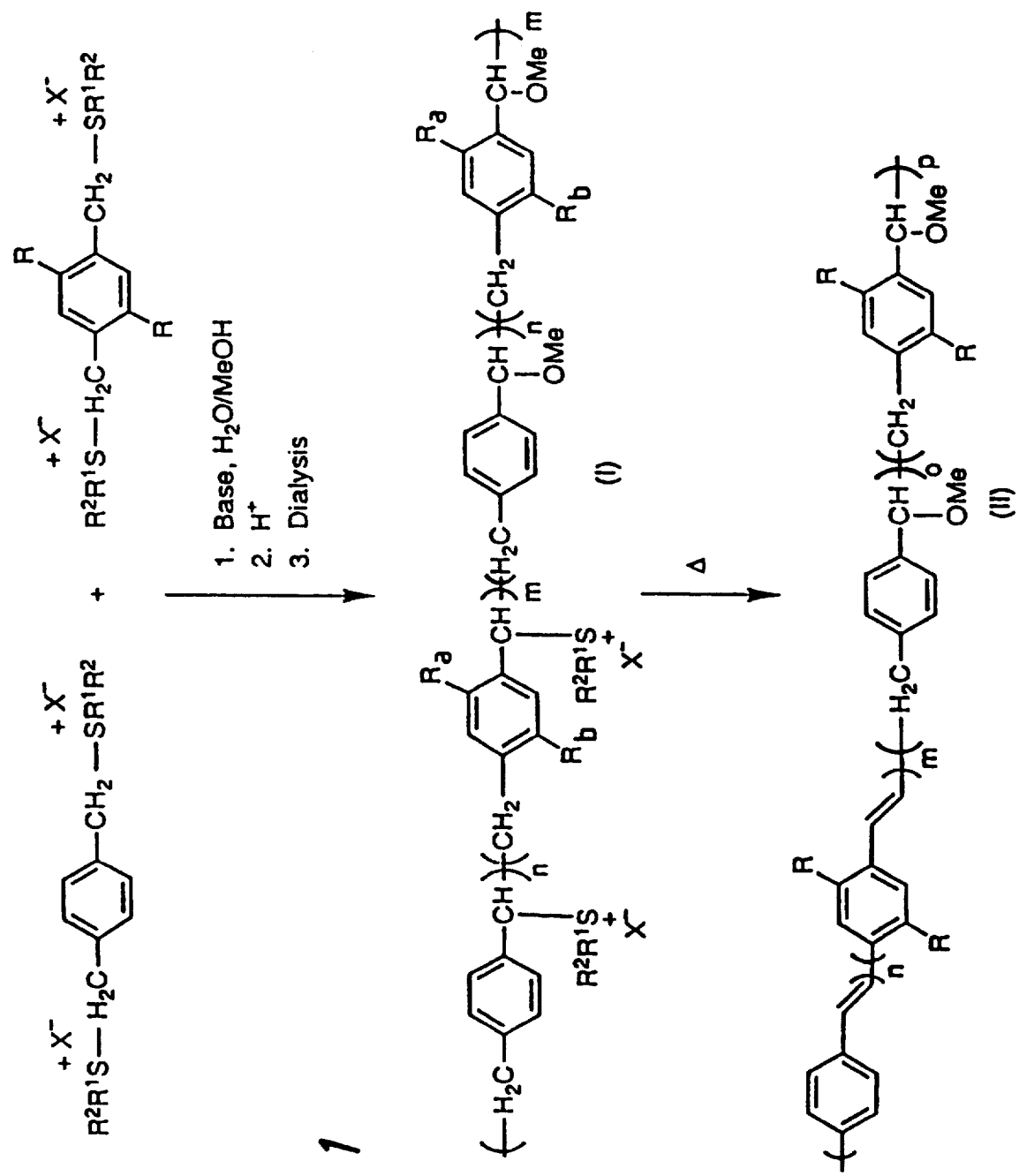
FIG. 1 is a diagram showing an example of the steps of a method for producing the copolymers prepared via a soluble precursor.

FIG. 1 illustrates in general terms a process for producing copolymers according to one embodiment of the invention. A mixture of two monomeric bis-sulphonium salts in a suitable solvent was polymerised by reaction with a base. The resultant soluble precursor copolymer was purified and then converted to a conjugated form by heat treatment.

Examples of both the precursor copolymers and the partially conjugated copolymers are shown in the foregoing formulae drawings. The compound of General Formula I represents a precursor copolymer of the compound of General Formula II, which is a poly(paraphenylene vinylene-co-2,5-disubstituted-para phenylene vinylene) copolymer. Similarly, the compound of General Formula III represents a precursor copolymer of the compound of General Formula IV, which is a poly(2,5-thienylene vinylene-co-disubstituted-para-phenylene vinylene) copolymer.

In these compounds the extent of conjugations will be determined by the values of n,m,o and p. Clearly, for a partially conjugated copolymer (II) or (IV), $o+p \geq 1$, and so at least some of the vinylic groups will be saturated by inclusion of the modifier group represented by —OR'.

The present invention is concerned in one aspect with improving the efficiency of radiative decay of excitons by trapping them on local regions of the polymer chain, which have lower energy gaps and thus are regions of lower potential energy for the excitons, so that the excitons are confined for a long enough period that they will decay radiatively. This has been achieved by the synthesis of a family of copolymers in which the units which make up the polymer chain are selected from two or more chemically different groups, which possess differing bandgaps in their respective homopolymers. Such polymers have been synthesised while still retaining all the desirable processing and materials properties of PPV. In the examples shown in this disclosure, paraphenylene vinylene is used as one of the components (usually the majority component) together with varying compositions of the following other components or their unconverted precursors, as discussed more fully below:

2,5-dimethoxy-para-phenylene vinylene
(PDMOPV)

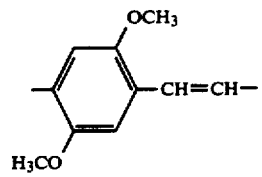

2,5-thienylene vinylene
(PTV)

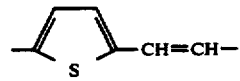

2,5-dimethyl-para-phenylene vinylene
(PDMPV)

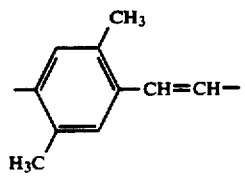

2-methoxy-5-(2'-methylpentyloxy)para-phenylene vinylene
(MMP-PPV)

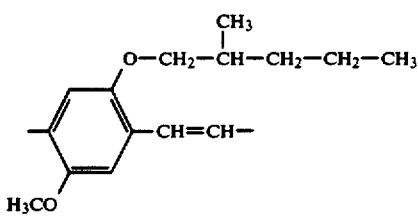

2-methoxy-5-(2'-ethylhexyloxy)para-phenylene vinylene (MEH-PPV)

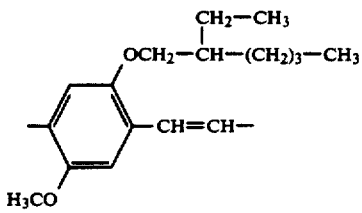

The first three of these components are available in the form of their corresponding homopolymers, and the first two possess an energy gap lower than that of PPV. PPV shows the onset of $\pi$ to $\pi^*$ optical transitions at 2.5 eV; poly(2,5-dimethoxy-para-phenylene vinylene), PDMOPV, at 2.1 eV and poly(2,5-thienylene vinylene), PTV, at 1.8 eV. It is expected, on the basis of the known inductive effects of its substituents, that poly(2,5-dimethyl-para-phenylene vinylene), PDMPV, will have a bandgap a little lower than that of PPV.

Dimethyl PPV (DMPPV) has a higher bandgap in its homopolymer than does PPV. This is contrary to the argument which runs that the methyl substituents have inductive effects and so will lower the bandgap of DMPPV over PPV. The true picture is that due to the steric interaction of the dimethyl groups, the polymer conjugated backbone is distorted decreasing the degree of electron delocalisation along the backbone and thus raising the bandgap with respect to PPV. This is evidenced in electron diffraction studies and quantum chemical calculations.

Thus, the copolymers of PPV and DimethylPPV as prepared via a THT leaving group (FIG. 8) have a controlled shift in bandgap not because the DMPPV units are saturated giving a copolymer of saturated and unsaturated units but because DMPPV and PPV have genuinely different bandgaps and we are forming a copolymer of the two. We evidence that there are no saturated units by an absence of 1094 cm$^{-1}$ stretch in the FTIR spectra of the precursors. Bandgap is still controllable hence by selection of the monomer units ratio.

There follows specific examples of processes in accordance with embodiments of the invention.

EXAMPLE 1

A mixture of α,α-bis(tetrahydrothiophenium chloride)-p-xylene (0.97 g, 2.8 mmol) and α,α-bis(tetrahydrothiophenium chloride)-2,5-dimethoxy-p-xylene (0.12 g, 0.3 mmol) in methanol (7.1 ml) was deoxygenated with nitrogen and cooled with an ice-bath. A nitrogen deoxygenated aqueous sodium hydroxide solution (0.4M, 2.9 mmol, 7.1 ml) was added dropwise and the reaction mixture was left to stir for 1 hour at 0° C. under inert atmosphere. The reaction was terminated by addition of hydrochloric acid (0.4M, 1.0 ml). The viscous solution was then dialyzed against deoxygenated distilled water (3×1000 ml) over 3 days using cellulose membrane dialysis tubing with a molecular weight cut-off of 12,400 (supplied by Sigma Chemical Company Limited, Dorset, U.K.). The solvent was completely removed in vacuo at room temperature from the material remaining in the dialysis tubing. The residue was dissolved in dry methanol (15 ml).

EXAMPLE 2

A mixture of α,α-bis(tetrahydrothiophenium chloride)-p-xylene (0.91 g, 2.6 mmol) and α,α-bis(tetrahydrothiophenium chloride)-2,5-dimethyl-p-xylene (0.10 g, 0.26 mmol) in methanol (9.5 ml) was deoxygenated with nitrogen and cooled with an ice-bath. A nitrogen deoxygenated ice-cold aqueous sodium hydroxide solution (0.4M, 2.9 mmol, 7.1 ml) was added dropwise and the reaction mixture was left to stir for 1 hour at 0° C. under inert atmosphere. The reaction was terminated by addition of hydrochloric acid (0.4M, 0.5 ml). The viscous solution was then dialyzed against deoxygenated distilled water (3×1000 ml) over 4 days using cellulose membrane dialysis tubing with a molecular weight cut-off of 12,400 (supplied by Sigma Chemical Company Limited, Dorset, U.K.). The solvent was completely removed in vacuo at room temperature from the material remaining in the dialysis tubing. The residue was dissolved in dry methanol (10 ml).

EXAMPLE 3

A mixture of α,α-bis(tetrahydrothiophenium chloride)-p-xylene (0.98 g, 2.8 mmol) and α,α-bis(tetrahydrothiophenium chloride)-2-nitro-p-xylene (0.11 g, 0.33 mmol) in methanol (8.0 ml) was deoxygenated with nitrogen and cooled with an ice-bath. A nitrogen deoxygenated ice-cold aqueous sodium hydroxide solution (0.4M, 2.9 mmol, 8.0 ml) was added rapidly and the reaction mixture was left to stir for 3.5 hours at 0° C. under inert atmosphere. The reaction was terminated by addition of hydrochloric acid (0.4M, 1.0 ml). The viscous solution was then dialyzed against deoxygenated distilled water (3×1000 ml) over 4 days using cellulose membrane dialysis tubing with a molecular weight cut-off of 12,400 (supplied by Sigma Chemical Company Limited, Dorset, U.K.). The solvent was completely removed in vacuo at room temperature from the material remaining in the dialysis tubing. The residue was dissolved in dry methanol (4 ml).

EXAMPLE 4

Preparation of 1-methoxy-4-(2''-methylpentyloxy)benzene

Sodium metal (6.99 g, 304 mmol) was dissolved in dry methanol (120 ml) under Ar to give a 2.5M solution of sodium methoxide. A solution of 4-methoxyphenol (31.4 g, 253 mmol) in dry methanol (150 ml) was added and this mixture was heated to reflux for 30 min. After cooling to room temperature, a solution of 1-bromo-2-methylpentane (46.0 g, 279 mmol) in dry methanol (100 ml) was added. The mixture was then heated to reflux for 16 hours. The solvent was removed in vacuo, the residue dissolved in ether (200 ml), washed with dilute aqueous sodium hydroxide (250 ml) and water (500 ml), dried over MgSO$_4$ and concentrated in vacuo again. Distillation at 80° C./0.5 mm Hg afforded 14.0 g (27%) 1-methoxy-4-(2'-methylpentyloxy)benzene, $^1$H NMR (250.1 MHz, CDCl$_3$): δ=0.94(t,3 H), 1.02 (d, 3 H), 1.16–1.56 (m, 4 H), 1.93 (m, 1 H), 3.64–3.82 (m, 2 H), 3.77 (s, 3 H), 6.81–6.89 (m, 4 H), $^{13}$C NMR (100.6 MHz, CDCl$_3$): δ=14.3, 17.0 (both CH$_3$), 20.1, 35.8 (both CH$_2$), 33.0 (CH), 55.7 (OCH$_3$), 73.9 (OCH$_2$), 114.6, 115.4 (arom. CH), 153.5, 153.6 (ipso C). IR(film): 2956(m), 1509(s), 1232(s), 1045(m), 824(m) cm$^{-1}$, MS(EI) :m/z (%)=208 (100), 124 (32), Calcd. for C$_{13}$H$_{20}$O$_2$: C 74.96, H 9.68 found: C 75.03, H 9.70.

EXAMPLE 5

Preparation of 1,4-bis(chloromethyl)-2-methoxy-5-(2'-methylpentyloxy)benzene

A mixture of hydrochloric acid (37%, 59 ml), formaldehyde (39%, 35 ml), 1-methoxy-4-(2'-methylpentyloxy)benzene (14.0 g, 67.4 mmol) and dioxane (100 ml) was saturated with hydrogen chloride for 15 min at 0° C. and stirred for 1.5 hours at room temperature. Another 30 ml of formaldehyde was then added at 0° C. and hydrogen chloride was bubbled through the reaction mixture for 10 min. After stirring for 16.5 hours at room temperature, the mixture was heated to reflux for 4 hours. The solvents were then completely removed to give a colourless solid residue which was dissolved in a minimum amount of hot hexane (50 ml). This solution was poured into ice-cold methanol (300 ml). The precipitate was filtered under suction and dried to afford 15.5 g (75%) of 1,4-bis(chloromethyl)-2-methoxy-5-(2'-methylpentyloxy)benzene, m.p. 78°–80° C. $^1$H NMR (250.1 MHz, CDCl$_3$): δ=0.92( t, 3 H), 1.04 (d, 3 H), 1.22–1.55 (m, 4 H), 1.95–2.05 (m, 1 H), 3.73–3.90 (m, 2 H), 3.85 (s, H). $^{13}$C NMR (100.6 MHz, CDCl$_3$ ): δ=14.3, 17.1 (both CH$_3$), 20.0, 35.7 (both CH$_2$), 33.0 (CH), 41.3, 41.4 (both CH$_2$Cl), 56.3 (OCH$_3$), 73.9 (OCH$_2$) 113.3, 114.1 (arom. CH), 126.8, 127.0, 150.8, 150.9 (ipso C). IR (KBr): 2958 (m), 1517 (s), 1466 (m), 1414 (s), 1263 (s), 1230 (s), 1036 (s), 734 (s), 696 (s) cm$^{-1}$. MS(EI) : m/z (%)=304 (18), 220 (38), 84 (41). Calcd for C$_{15}$H$_{22}$Cl$_2$O$_2$: C 59 02, H 7.26; found: C 58.14, H 6.97.

EXAMPLE 6

Preparation of α,α-bis(tetrahydrothiophenium chloride)-2-methoxy-5-(2 '-methylpentyloxy)-p-xylene Tetrahydrothiophene (20.9 ml, 237 mmol) was added to a suspension of 1,4-bis(chloromethyl)-2-methoxy-5-(2'-methylpentyloxy)benzene(14.5 g, 47.3 mmol) in dry methanol (200 ml). The solid dissolved to form a clear solution within 10 min. This solution was then heated to 50° C. for 17 hours. The solvent was completely removed in vacuo, the residue treated with dry acetone, then filtered under suction and dried to give 12.7 g (56%) of α, α-bis(tetrahydrothiophenium chloride)-2-methoxy-5-(2'-methylpentyloxy)-p-xylene. $^1$H NMR (250.1 MHz, CD$_3$OD):=0.97(t, 3 H), 1.10 (d, 3 H), 1.26–1.61 (m, 4 H) , 2.04 (m, 1 H), 2.23–2.53 (m, 8 H), 3.55 (br. m, 8 H), 3.86–4.05 (m, 2 H), 3.97 (s, 3 H), 4.56 (s, 2 H), 4.57 (s, 2 H), 7.35 (s, 1 H), 7.37 (s, 1 H), $^{13}$C NMR (100.6 MHz, CD$_3$OD): δ=14.7, 17.5 (CH$_3$), 21.1, 29.7, 29.8, 34.3 (CH$_2$), 36.9 (CH), 43.1, 43.2, 44.5, 44.6, 44.8 (CH$_2$), 57.1 (OCH$_3$), 75.8 (OCH$_2$), 116.5, 117.3 (arom. CH), 121.3, 121.6, 153.0, 153.3 (ipso c). IR (KBr): 2953 (s), 1514 (s), 1404 (s), 1230 (s), 1033 (s) cm$^{-1}$.

EXAMPLE 7

Figure 18:
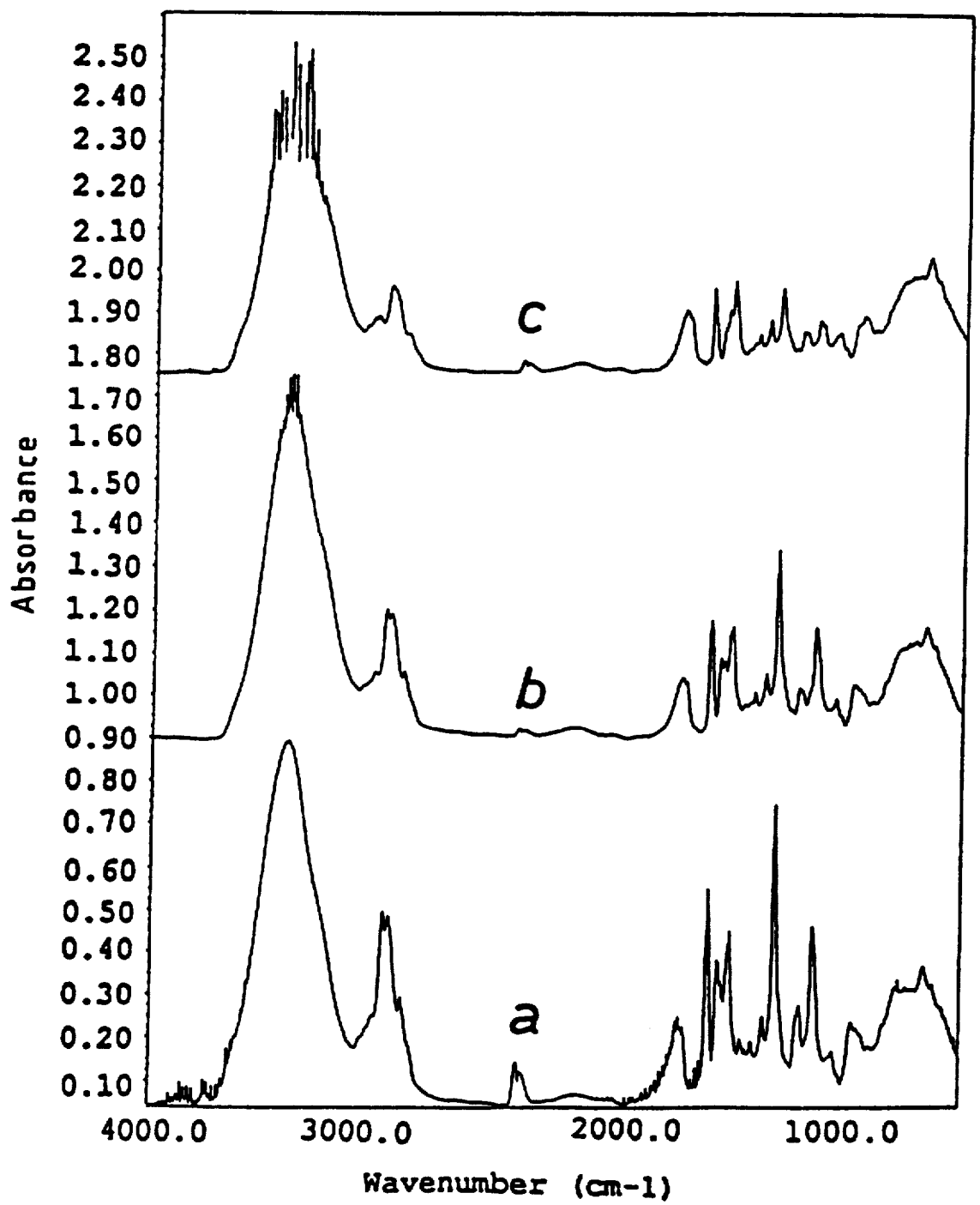
FIG. 18 are graphs showing the infrared spectra of precursor to random copolymers of PPV and MMP-PPV(2-methoxy-5-(2'-methylpentyloxy)-PPV produced from 80:20 (a), 90:10 (b), and 95:5 (c) w/w ratios of PPV and MMP-PPV monomer units, respectively.

A mixture of α,α-bis(tetrahydrothiophenium chloride)-p-xylene (0.90 g, 2.6 mmol) and α,α-bis(tetrahydrothiophenium chloride)-2-methoxy-5-(2'-methylpentyloxy)-p-xylene (0.10 g, 0.21 mmol) in methanol (10 ml) was deoxygenated with argon and cooled with an ice-bath. An argon deoxygenated ice-cold aqueous sodium hydroxide solution (0.4M, 2.6 mmol, 6.9 ml) was added dropwise and the reaction mixture was left to stir for 1 hour at 0° C. under inert atmosphere. The reaction was terminated by addition of hydrochloric acid (0.4M, 3.0 ml). The viscous solution was then dialyzed against deoxygenated distilled water (3×2000 ml) over 3 days using cellulose membrane dialysis tubing with a molecular weight cut-off of 12,400 (supplied by Sigma Chemical Company Ltd., Dorset, U.K.). The solvent was completely removed in vacuo at room temperature from the material remaining in the dialysis tubing. The residue was dissolved in dry methanol (20 ml). IR spectra of copolymers: FIG. 18.

EXAMPLE 8

Preparation of 1-methoxy-4-(2'-ethylhexyloxy)benzene

Sodium metal (6.50 g, 283 mmol) was dissolved in dry methanol (100 ml) under Ar to give a 2.5M solution of sodium methoxide. A solution of 4-methoxyphenol (29.3 g, 236 mmol) in dry methanol (150 ml) was added and this mixture was heated to reflux for 30 min. After cooling to room temperature, a solution of 1-bromo-2-ethylhexane (46.5 g, 259 mmol) in dry methanol (150 ml) was added dropwise. The mixture was then heated to reflux for 18 hours. The solvent was removed in vacuo, the residue dissolved in ether (200 ml), washed with dilute aqueous sodium hydroxide (500 ml) and water (500 ml), dried over MgSO$_4$ and concentrated in vacuo again. Distillation at 120° C./0.1 mm Hg afforded 24.2 g (43%) 1-methoxy-4-(2'-ethylhexyloxy)benzene.

EXAMPLE 9

Preparation of 1,4-bis(chloromethyl)-2-methoxy-5-(2'-ethylhexyloxy)-benzene

A mixture of hydrochloric acid (37%, 90 ml), formaldehyde (39%, 70 ml), 1-methoxy-4-(2'-ethylhexyloxy)benzene (24.2 g, 101 mmol) and dioxane (120 ml) was saturated with hydrogen chloride for 20 min at 0° C. and stirred for 3 hours at room temperature. Another 50 ml of formaldehyde was then added at 0° C. and hydrogen chloride was bubbled through the mixture for 10 min. After stirring for 3 days at room temperature, the mixture was heated to reflux for 3.5 hours. The solvents were then completely removed to give a pale yellow solid residue which was dissolved in a minimum of hot hexane (75 ml). This solution was poured into ice-cold methanol (300 ml). The precipitate was filtered under suction, washed with methanol (200 ml) and dried to afford 21.7 g (63%) of 1,4-bis (chloromethyl)-2-methoxy-5-(2'-ethylhexyloxy)benzene, m.p. 58°–60° C. From the mother liquor was obtained another 5.48 g (16%) of bis(chloromethyl)-2-methoxy-5-(2'-ethylhexyloxy)benzene, m.p. 53°–55° C. $^1$H NMR (250.1 MHz, CDCl$_3$): δ=0.85–0.96 (m, 6 H), 1.26–1.75 (m, 9 H), 3.74–3.86 (m, 1H). IR (KBr): 2924 (m), 1516 (s), 1466 (m), 1415 (s), 1263 (s), 1227 (s), 1182 (m), 1032 (s), 733 (m), 700 (s), 614 (m).

EXAMPLE 10

Preparation of α,α'-bis(tetrahydrothiophenium chloride)-2-methoxy-5-(2'-ethylhexyl)-p-xylene Tetrahydrothiophene (6.4 ml, 72 mmol) was added to a suspension of 2,5-bis(chloromethyl)-1-methoxy-4-(2'-ethylhexyloxy)benzene (4.80 g, 14.4 mmol) in dry methanol (75 ml). The mixture was then heated to 50° C. for 22 hours. The solvent was completely removed in vacuo, the residue treated with dry acetone, then filtered under suction and dried to give 4.36 g (59%) of α,α'-bis(tetrahydrothiophenium chloride)-2-methoxy-5-(2'-ethylhexyloxy)-p-xylene. $^1$HNMR (250.1 MHz, $CD_3OD$): δ=0.89-1.04 (M), 1.18 (t,J - 7.0 Hz, 3H), 1.29-1.65 (m, 8 H), 1.82 (m, 1 H), 2.32-2.55 (m, 8 H), 3.50-4.56, 4.57 (both s, 2 H, $CH_2Cl$), 7.38 and 7.39 (both s, 1 H, arom. H). IR (KBr): 2948 (broad, m), 1514 (s), 1460 (m), 1399 (s), 1312 (m), 1229 (s), 1033 (s), 703 $cm^{-1}$ (m).

EXAMPLE 11

Figure 22:
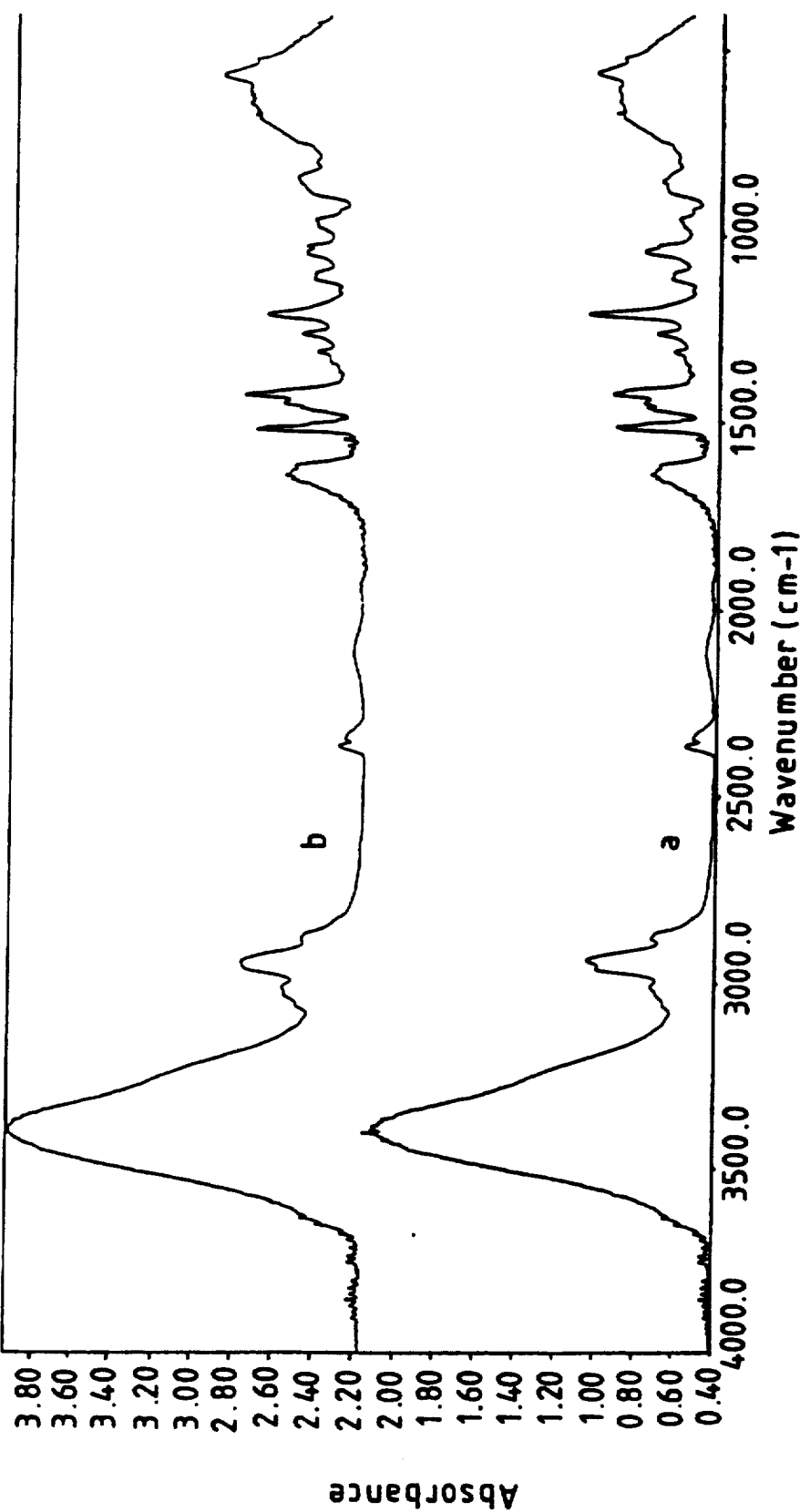
FIG. 22 are graphs showing the infrared spectra of precursors of random copolymers of PPV and MEH-PPV (2-methoxy-5-(2'-ethylhexyloxy)-PPV produced from 90:10 (a) and 95:5 (b) w/w ratios of PPV and MEH-PPV (2-methoxy-5-(2'-ethlyhexyloxy)-PPV) monomer units respectively.

A mixture of α,α'-bis(tetrahydrothiophenium chloride)-p-xylene (0.92 g, 2.6 mmol) and α,α'-bis(tetrahydrothiophenium chloride)-2-methoxy-5-(2'-ethylhexyloxy)-p-xylene (0.11 g, 0.22 mmol) in methanol (10 ml) was deoxygenated with argon and cooled with an ice-bath. An argon deoxygenated ice-cold aqueous sodium hydroxide solution (0.4M, 2.6 mmol, 6.5 ml) was added dropwise and the reaction mixture was left to stir for 2.5 hours at 0° C. under inert atmosphere. The reaction was terminated by addition of hydrochloric acid (0.4M, 0.8 ml). The viscous solution was then dialyzed against deoxygenated distilled water (3-2000 ml) over 3 days using cellulose membrane dialysis tubing with a molecular weight cut-off of 12,400 (supplied by Sigma Chemical Company Ltd, Dorset, U.K.). The solvent was completely removed in vacuo at room temperature from the material remaining in the dialysis tubing. The residue was dissolved in dry methanol (20 ml). IR spectra of copolymers: FIG. 22.

EXAMPLE 12

Figure 24:
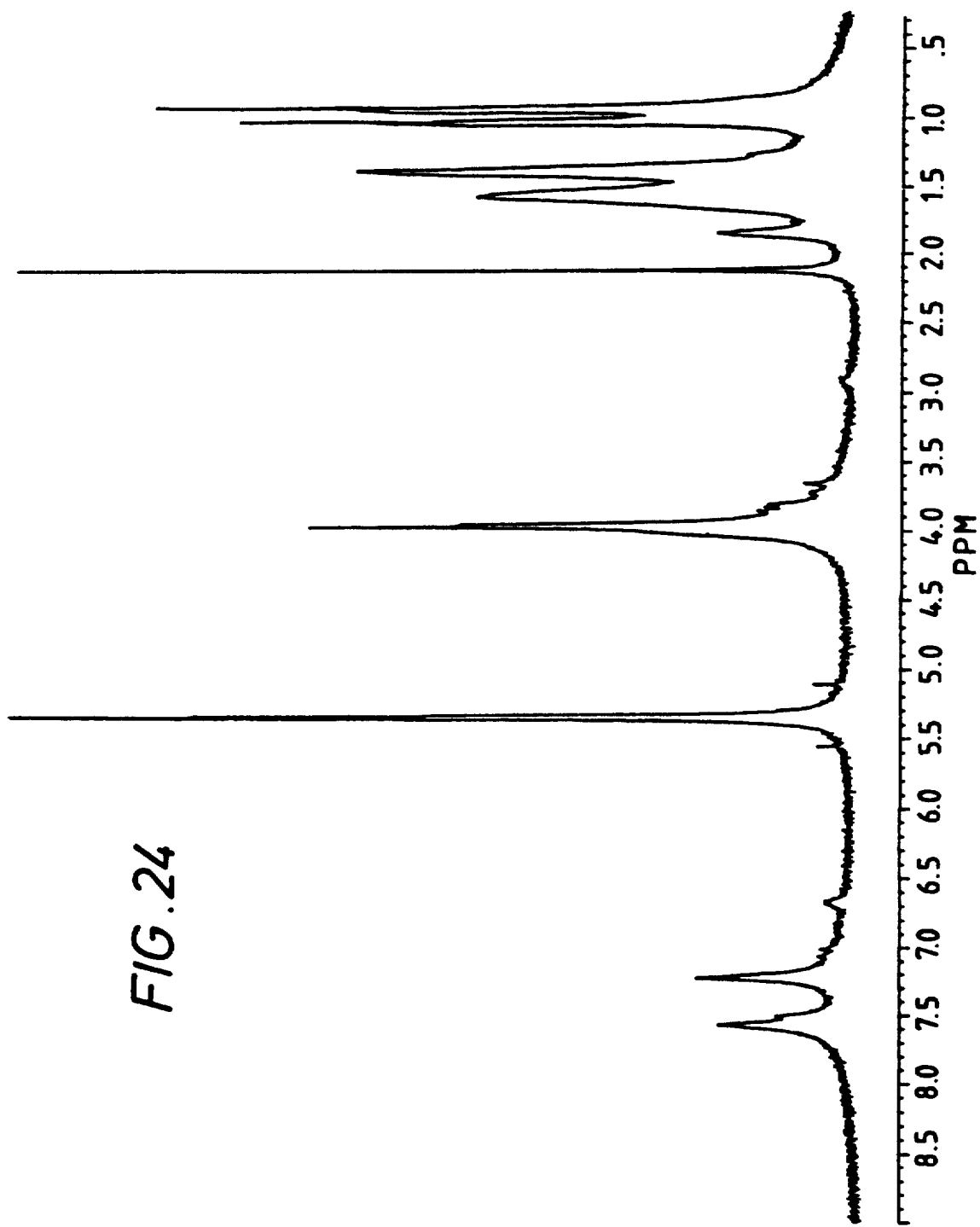
FIG. 24 is a $^1$H NMR spectrum of the copolymer described in example 11 produced from 5:95 w/w ratio of PPV and MEH-PPV monomer units.
Figure 25:
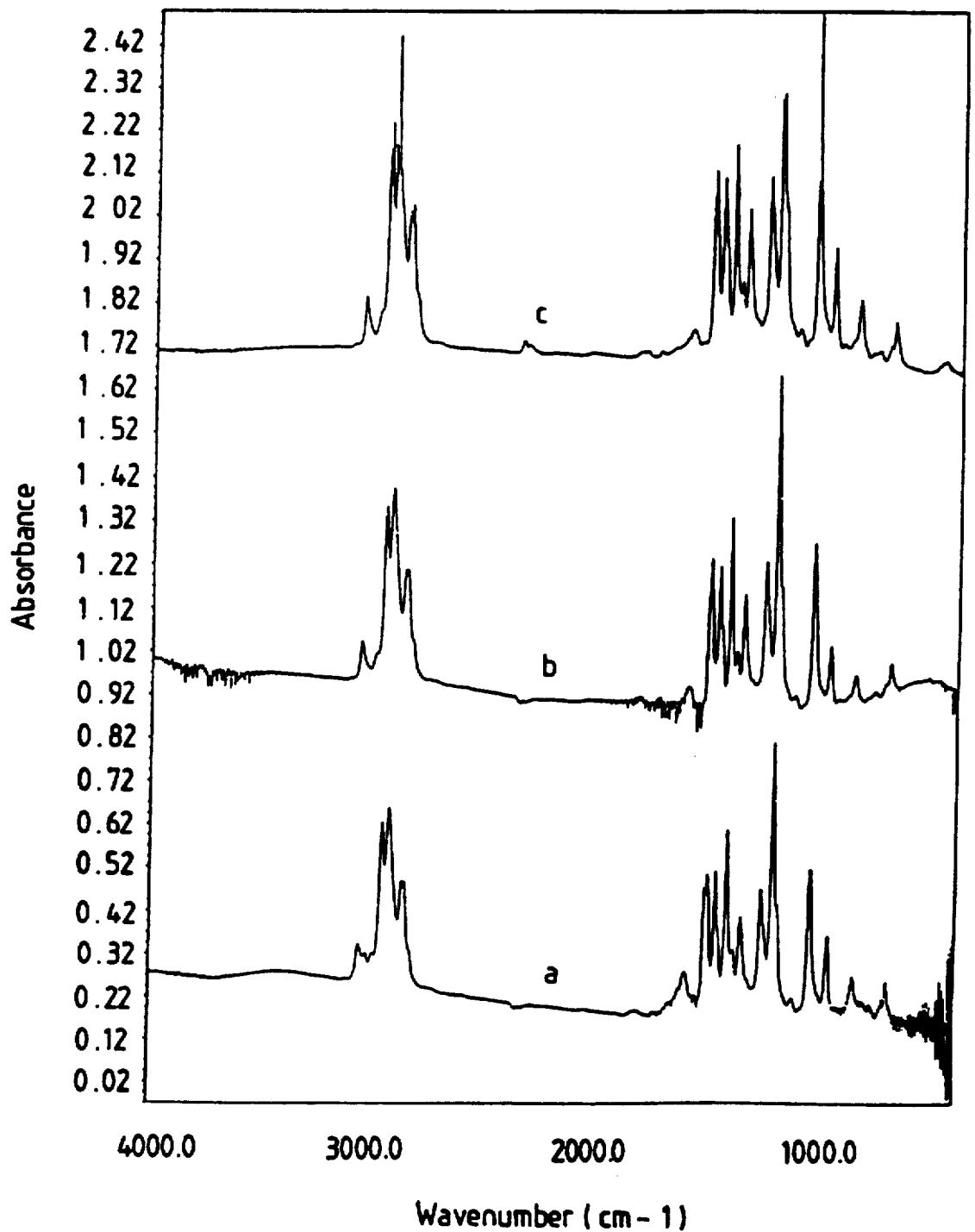
FIG. 25 are graphs showing the infrared spectra of (c) MEH-PPV and of random copolymers of PPV and MEH-PPV produced from (a) 20:80 and (b) 5:95 w/w ratios of PPV and MEH-PPV monomer units, respectively, by the method described in example 11.

A solution of 1,4-bis(chloromethyl)-2-methoxy-5-(2'-ethylhexyloxy) benzene (0.95 g, 2.9 mmol) and α,α'-dichloro-p-xylene (0.05 g, 0.29 mmol) in dry tetrahydrofuran (20 ml) was added to a solution of potassium tert-butoxide (95%, 2.5 g, 22 mmol) in dry tetrahydrofuran (120 ml) over 15 min. The mixture was then stirred at room temperature for 21.5 hours. The resulting orange mixture was reduced to 10% of its volume and poured into methanol (500 ml). The precipitate was filtered under suction and recrystallised from tetrahydrofuran/methanol to afford 101 mg of polymer. $^1$H NMR ($CD_2Cl_2$): FIG. 24. IR spectra of copolymers: FIG. 25.

Figure 26:
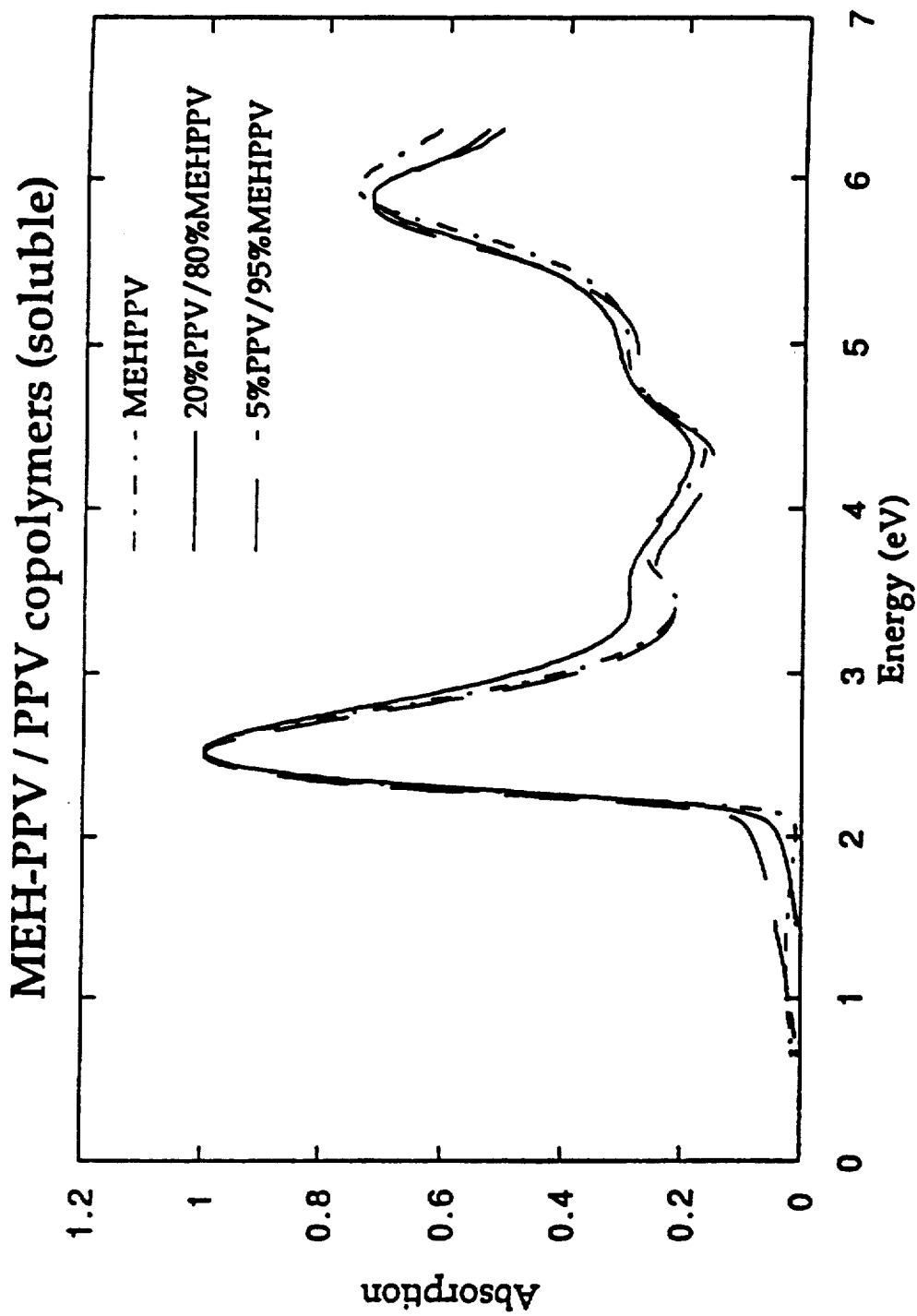
FIG. 26 is a graph showing the absorption spectra of spin-coated thin films of MEH-PPV and of random copolymers of PPV and MEH-PPV produced from 20:80 and 5:95 w/w ratios of PPV and MEH-PPV monomer units, respectively.
Figure 27A:
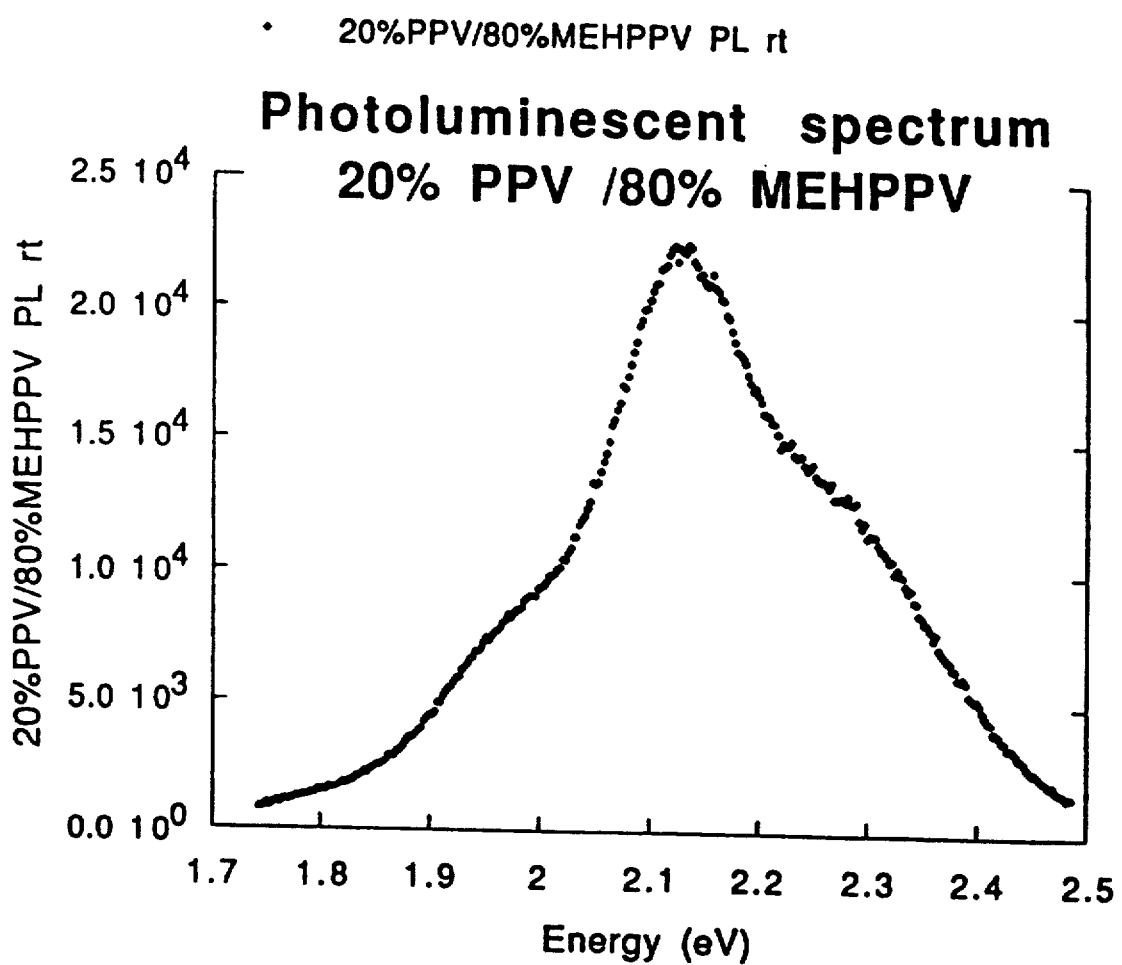
Figure 29A:
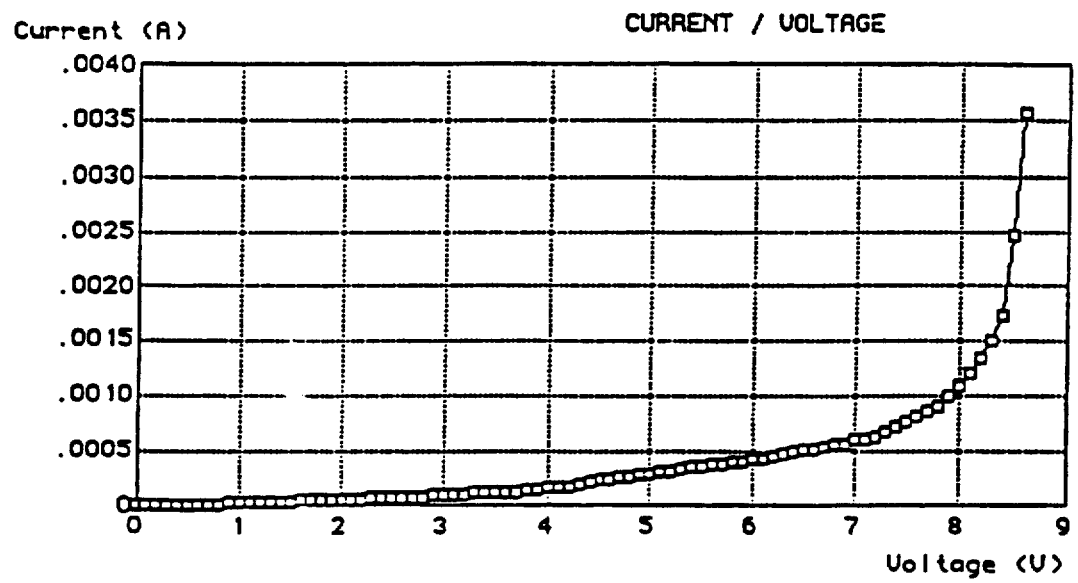
FIGS. 29a and 29b are graphs showing the current-/voltage characteristics and luminance/voltage relationship for a thin film of a random copolymer of PPV and MEH-PPV produced from 20:80 w/w ratio of PPV and MEH-PPV monomer units thin; films were spin-coated onto substates of ITO coated glass and aluminium cathodes were evaporated on top.
Figure 29B:
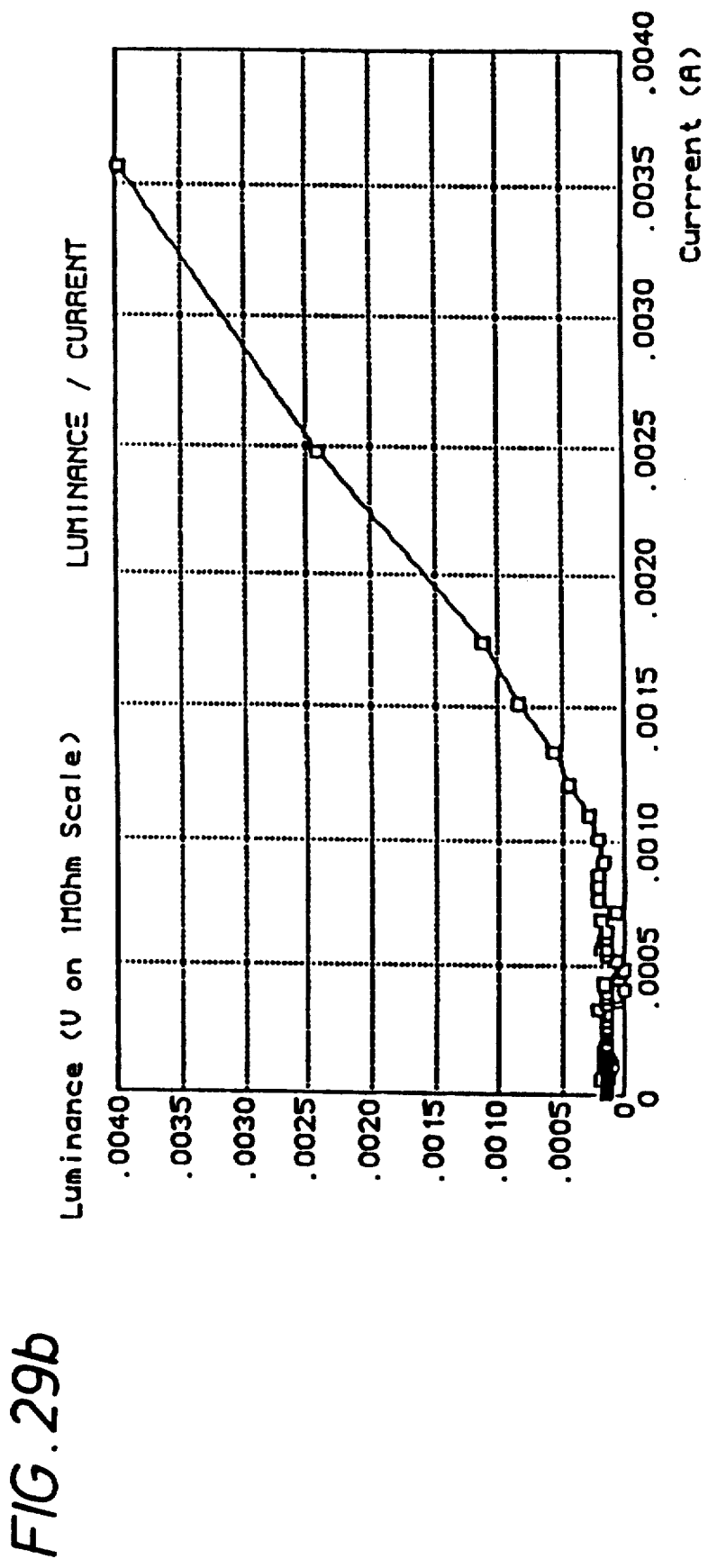
Figure 30A:
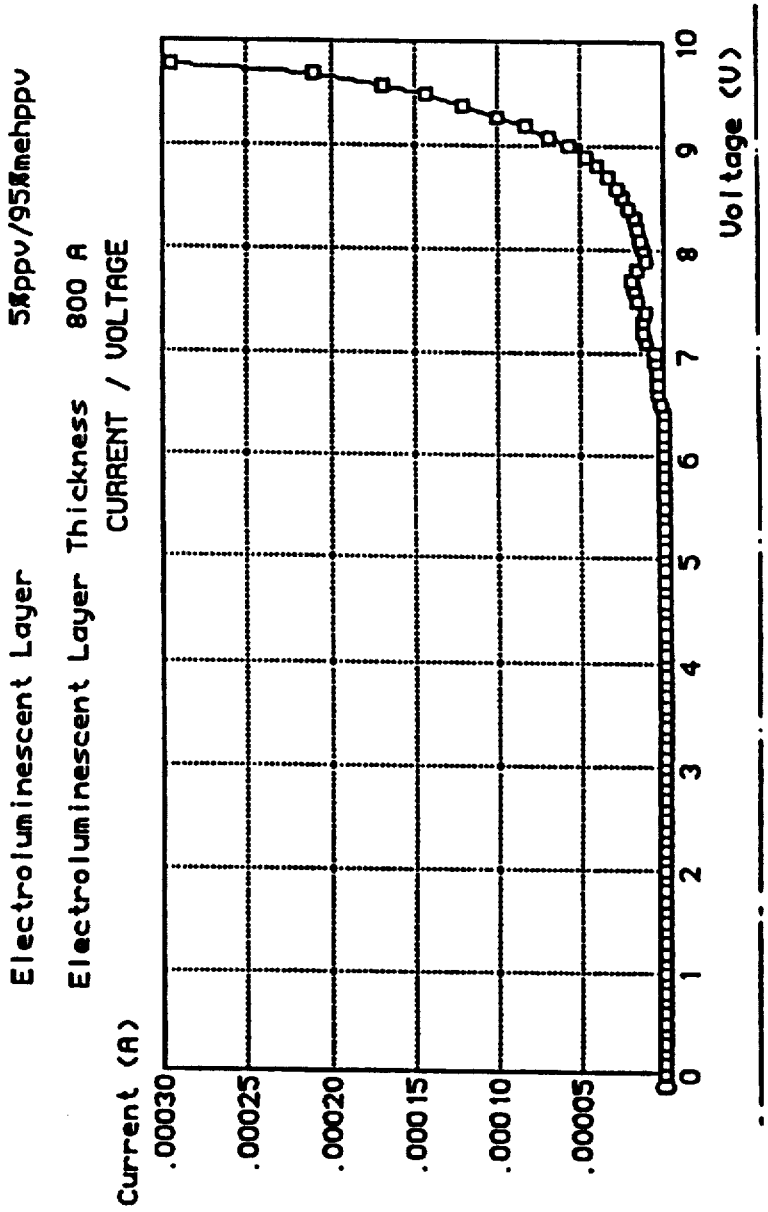
FIGS. 30a and 30b are graphs showing the current-/voltage characteristics and luminance/voltage relationship for a thin film of random copolymer of PPV and MEH-PPV produced from 5:95 w/w ratio of PPV and MEH-PPV monomer units: thin films were spin-coated onto substates of ITO coated glass and aluminium cathodes were evaporated on top.
Figure 30B:
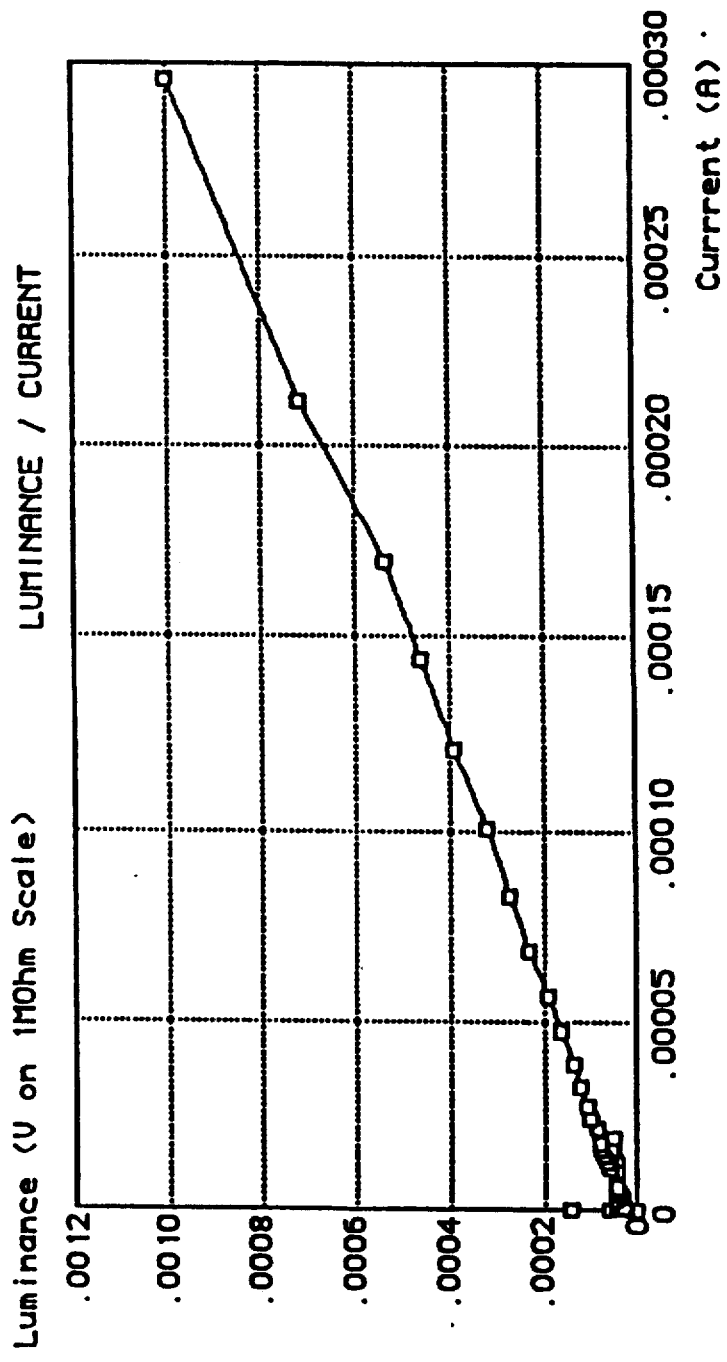
Figure 31:
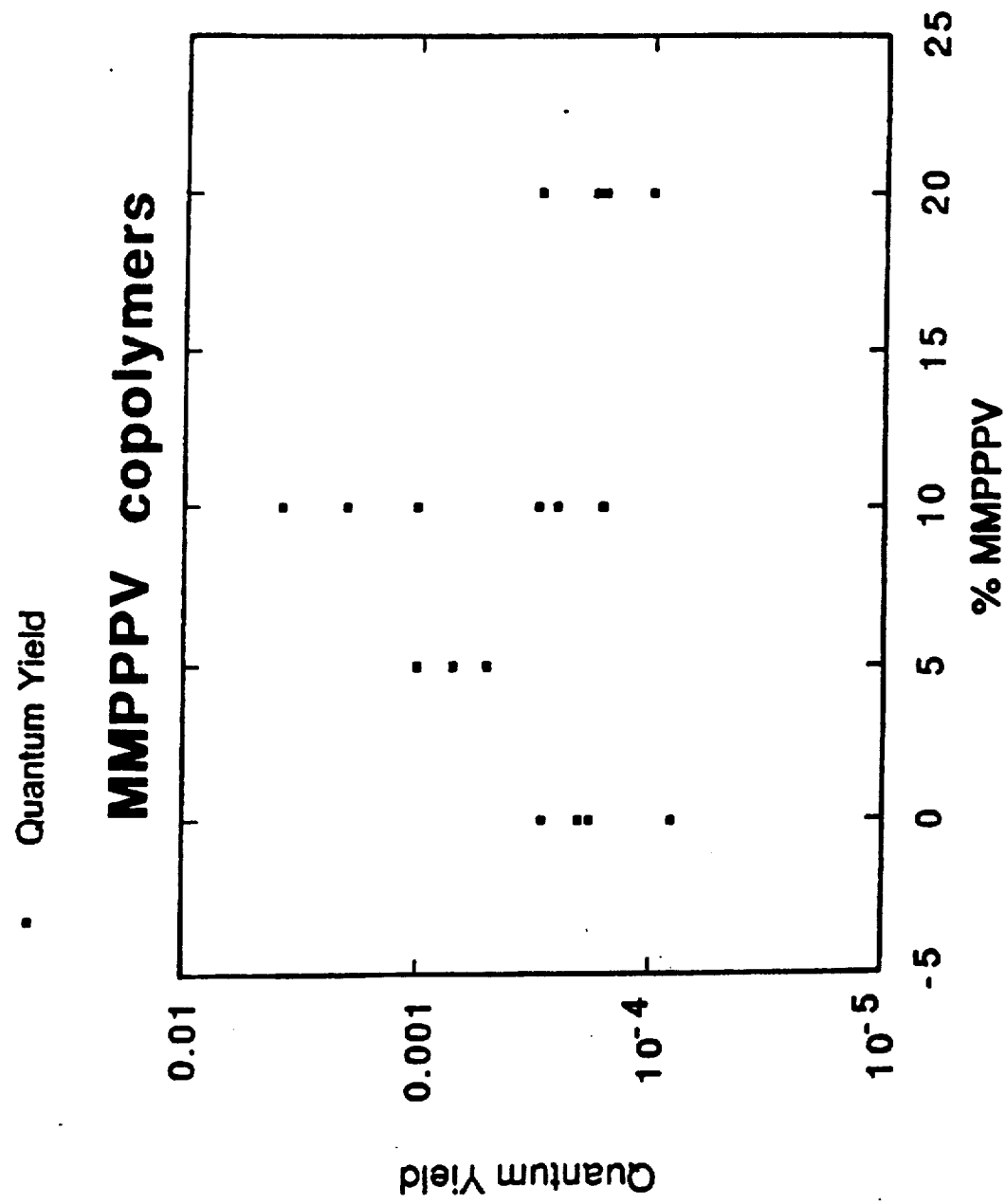
FIG. 31 is a scatter graph showing the quantum yield of random copolymers formed from PPV and MMP-PPV monomer units as measured in thin film structures with hole injecting electrodes of oxidised aluminium, a spin-coated film converted at 220° C. in vacuo for 12 hours, and with electron injecting electrodes of aluminium.
Figure 31A:
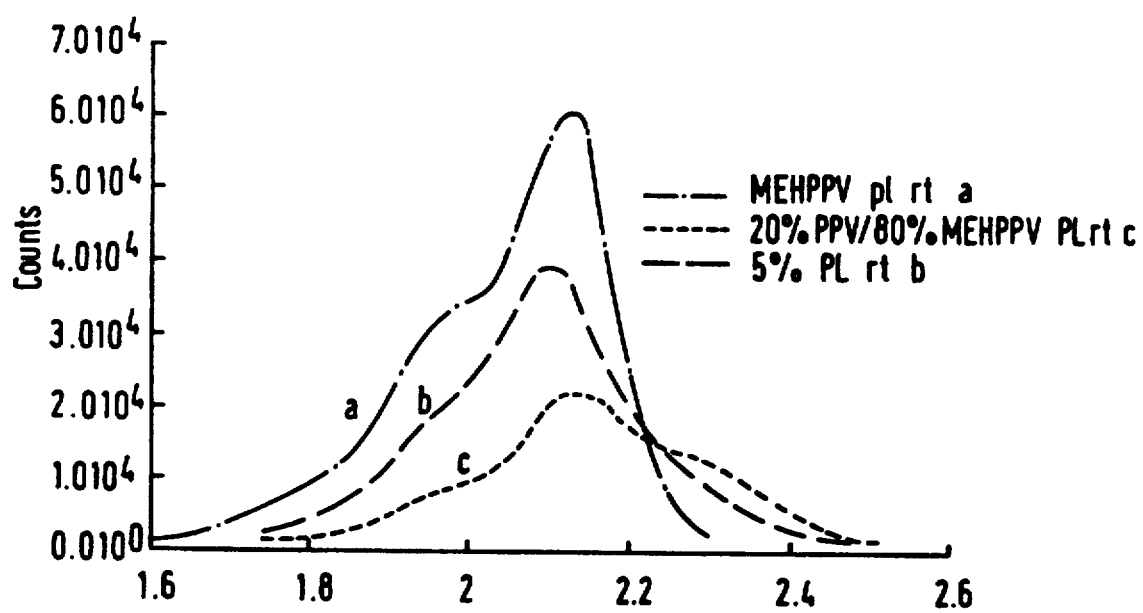
FIG. 31a is a graph showing the photoluminescence spectra of MEH-PPV and random copolymers of (a) MEH-PPV and PPV produced from (b) 95:5 and (c) 80:20 w/w ratios of MEH-PPV and PPV monomer units, respectively.

The absorption spectra of MEH-PPV, 5% PPV/95% MEH-PPV and 20% PPV/80% MEH-PPV are shown in FIG. 26. The photoluminescent spectra (FIGS. 27a, 26b, 31a) show that the luminescence is as expected of higher energy with increasing number of PPV units. EL devices were made in a standard configuration with ITO and aluminium contacts and the material showed electroluminescence (FIGS. 29a, 29b, 30a and 30b). The corresponding electroluminescence spectra are illustrated in FIGS. 28a and 28b. Both the 5% PPV/95% MEH-PPV and the 20% PPV/80% MEH-PPV had a turn-on voltage of about 8 V.

EXAMPLE 13

The previous PPV EL devices were constructed with PPV prepared via a Tetrahydrothiophenium (THT)-leaving precursor polymer (FIG. 32a) spun from methanolic solution. This precursor is unstable with respect to its conjugated product and is fully converted by heating at 220° C. for 2 hours (FIG. 32c).

Figure 33:
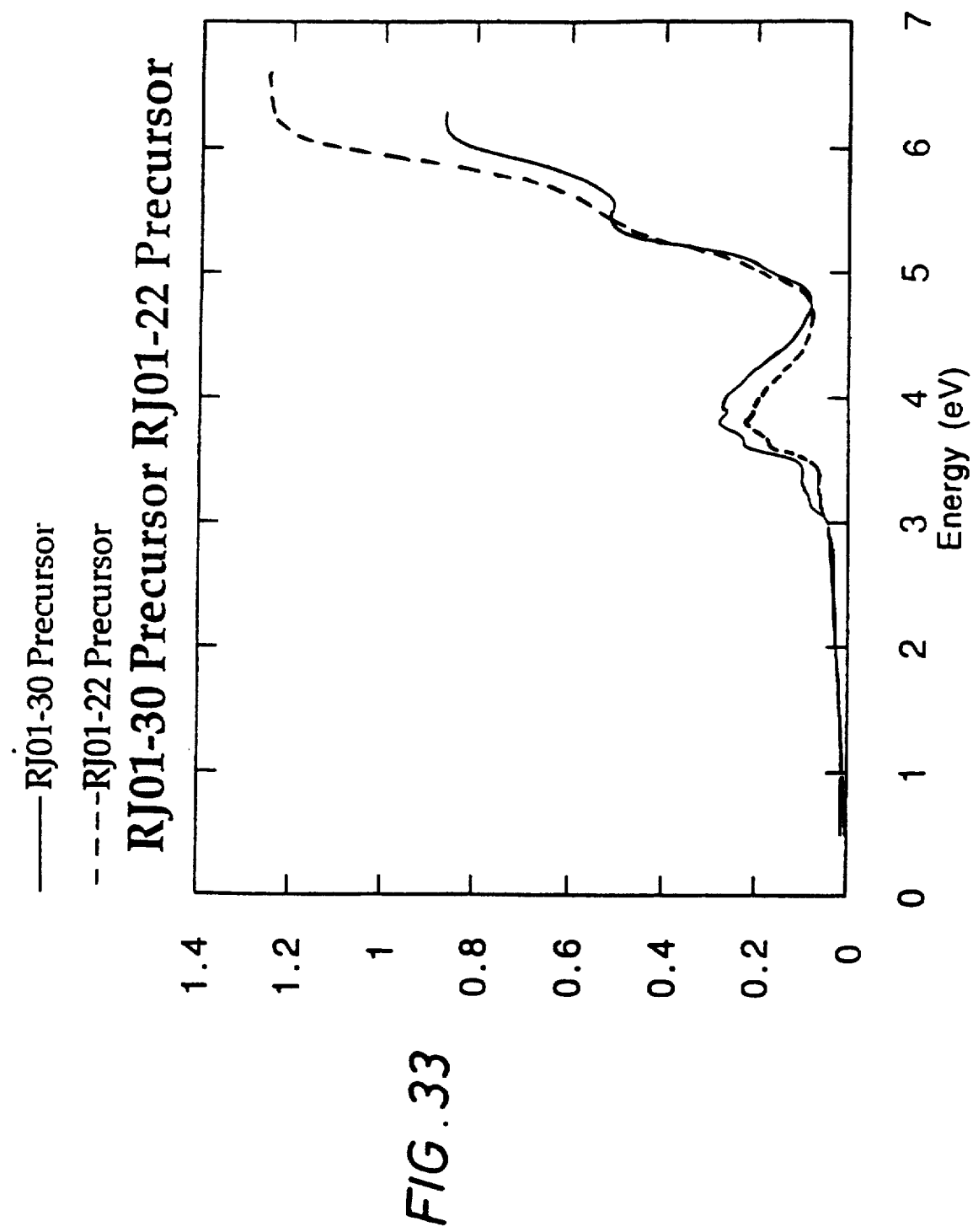
FIG. 33 is a graph showing the absorption spectra of precursors of THT-leaving PPV (broken) and MeO-leaving PPV (solid)
Figure 34:
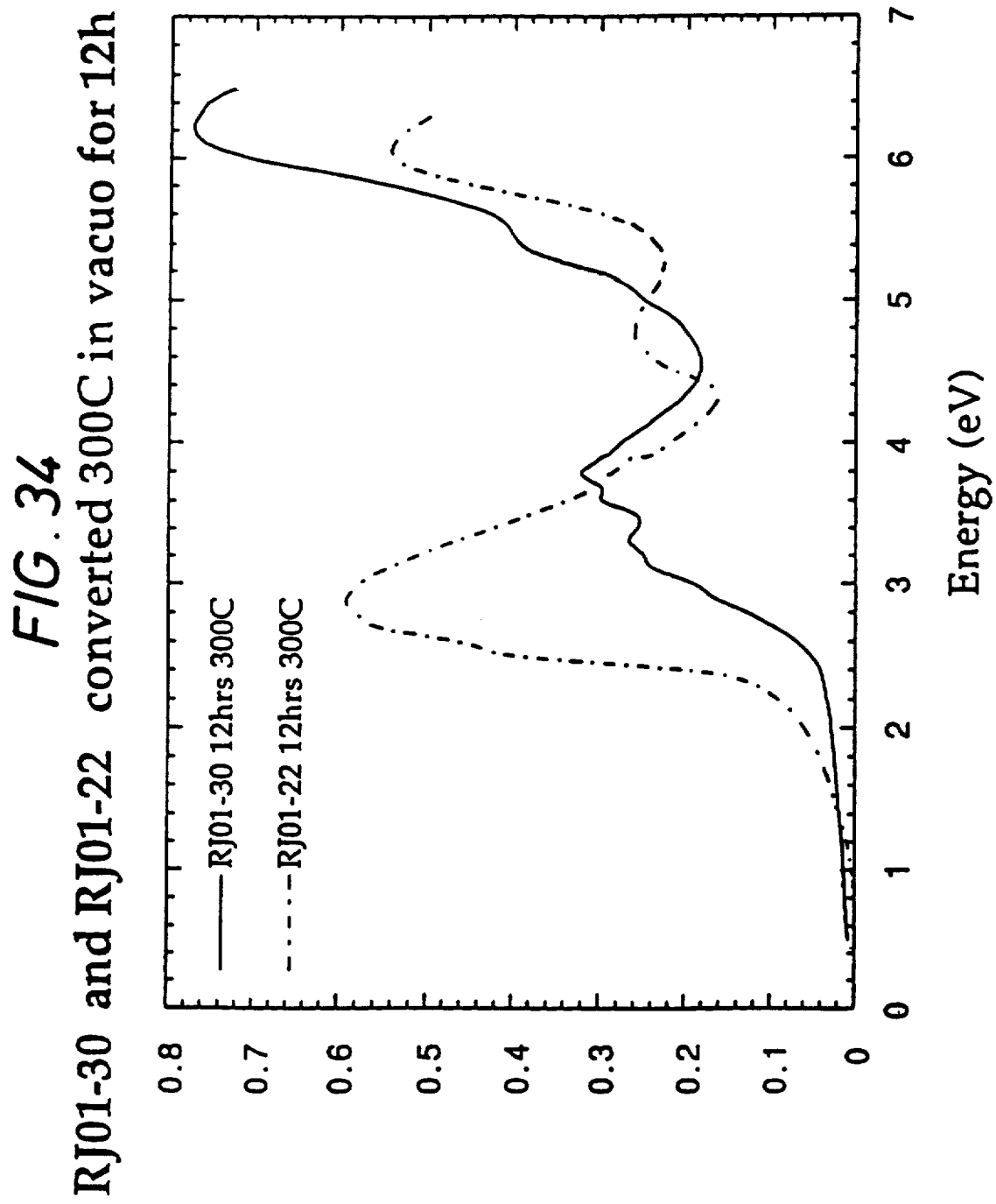
FIG. 34 is a graph showing the absorption spectra of THT-leaving PPV (broken) and MeO-leaving PPV (solid) after thermal conversion at 300° C. for 12 hours in vacuo.
Figure 35:
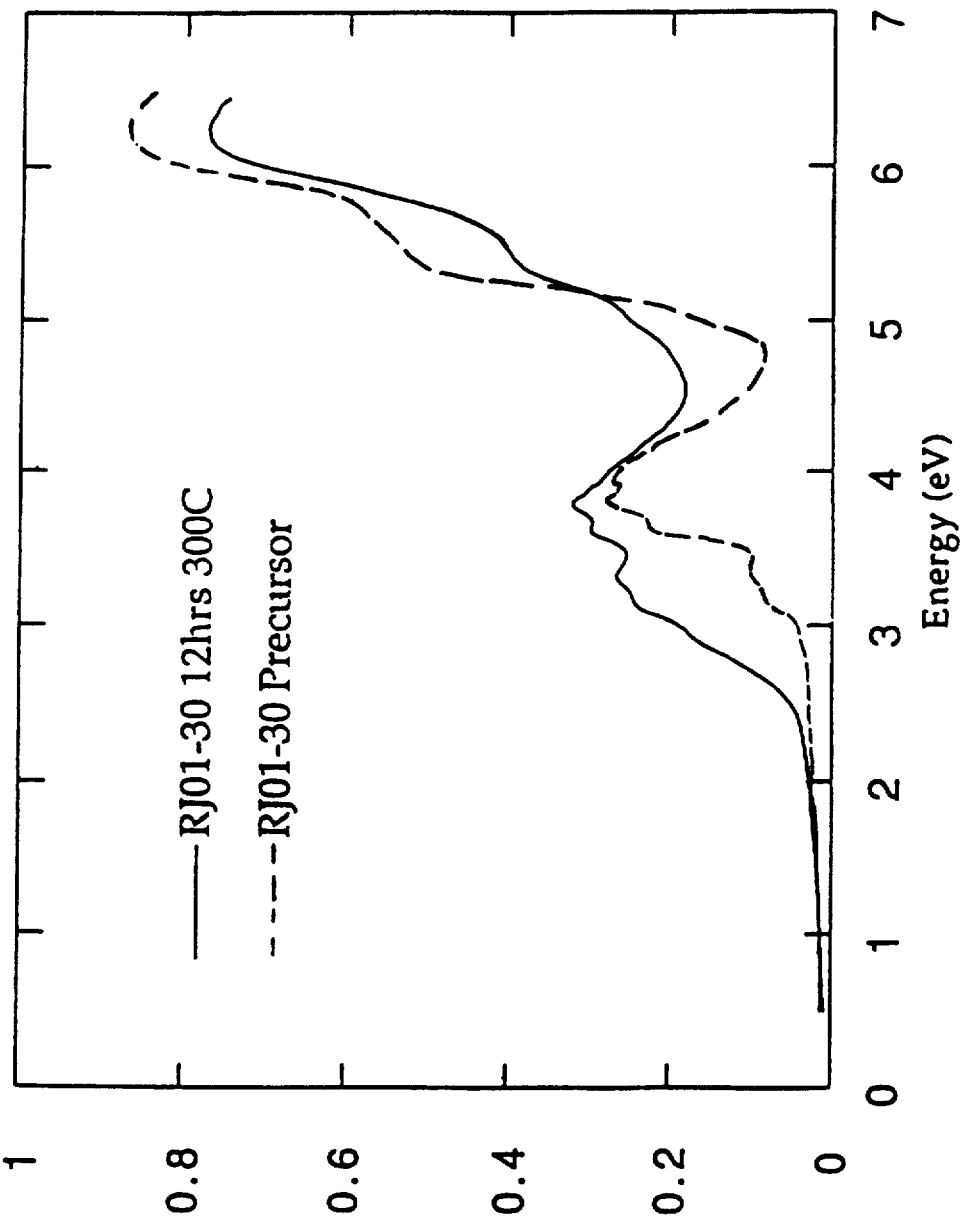
FIG. 35 is a graph showing the absorption spectra of thin spin-coated films of MeO-leaving PPV before (dotted) and after (solid) thermal conversion at 300° C. for 12 hours in vacuo.

By replacing the THT-leaving group with a methoxy (MeO)-leaving group a more stable precursor (FIG. 32b) is formed. This can be easily processed by spin coating from a solution in chloroform (as can the THT-precursor from methanolic solution). Thermal conversion of the MeO-leaving PPV precursor at 300° C. in vacuo for 12 hours gives very little thermal elimination leaving a copolymer of conjugated and unconjugated units (FIG. 32d). This is clearly seen from the absorption spectra of the THT-leaving PPV and the MeO-leaving PPV (FIG. 33). The absorption spectra of the precursors of both are very similar. A significant change occurs in the absorption spectrum of the THT-leaving PPV (FIG. 34); an insignificant change occurs in the absorption spectrum of the MeO-leaving PPV (FIG. 35). Clearly both products are subsequently very stable against subsequent changes at room temperatures and are very suitable as emitting materials in commercial EL devices.

A device was made with the MeO-leaving PPV. An ITO substrate was cleaned in an ultrasound bath, of first acetone and subsequently propan-2-ol. The precursor material was then spin-coated on the substrate. The device was then thermally converted at 300° C. in vacuo for 12 hours. A top contact of Aluminium was then deposited to define an active area by vacuum deposition at a pressure of less than $6.10^{-6}$ torr to a thickness of 2-500 Å.

Figure 36A:
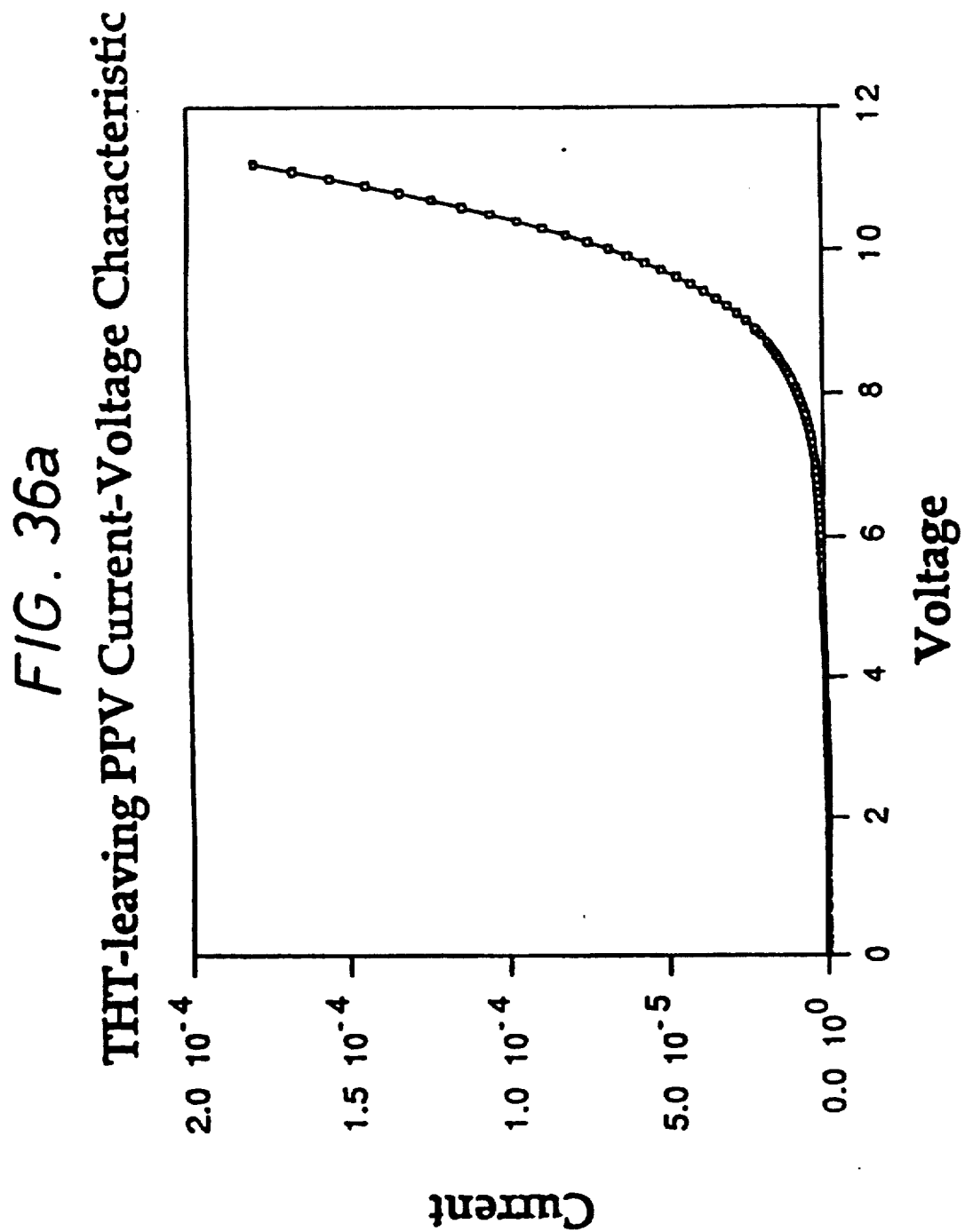
FIGS. 36 (a) and (b) are graphs showing respectively the current-voltage and luminance-current characteristics of THT-leaving PPV as converted in vacuo at 220° for 12 hours on a substrate of ITO-coated glass and with aluminium as a cathode.
Figure 36B:
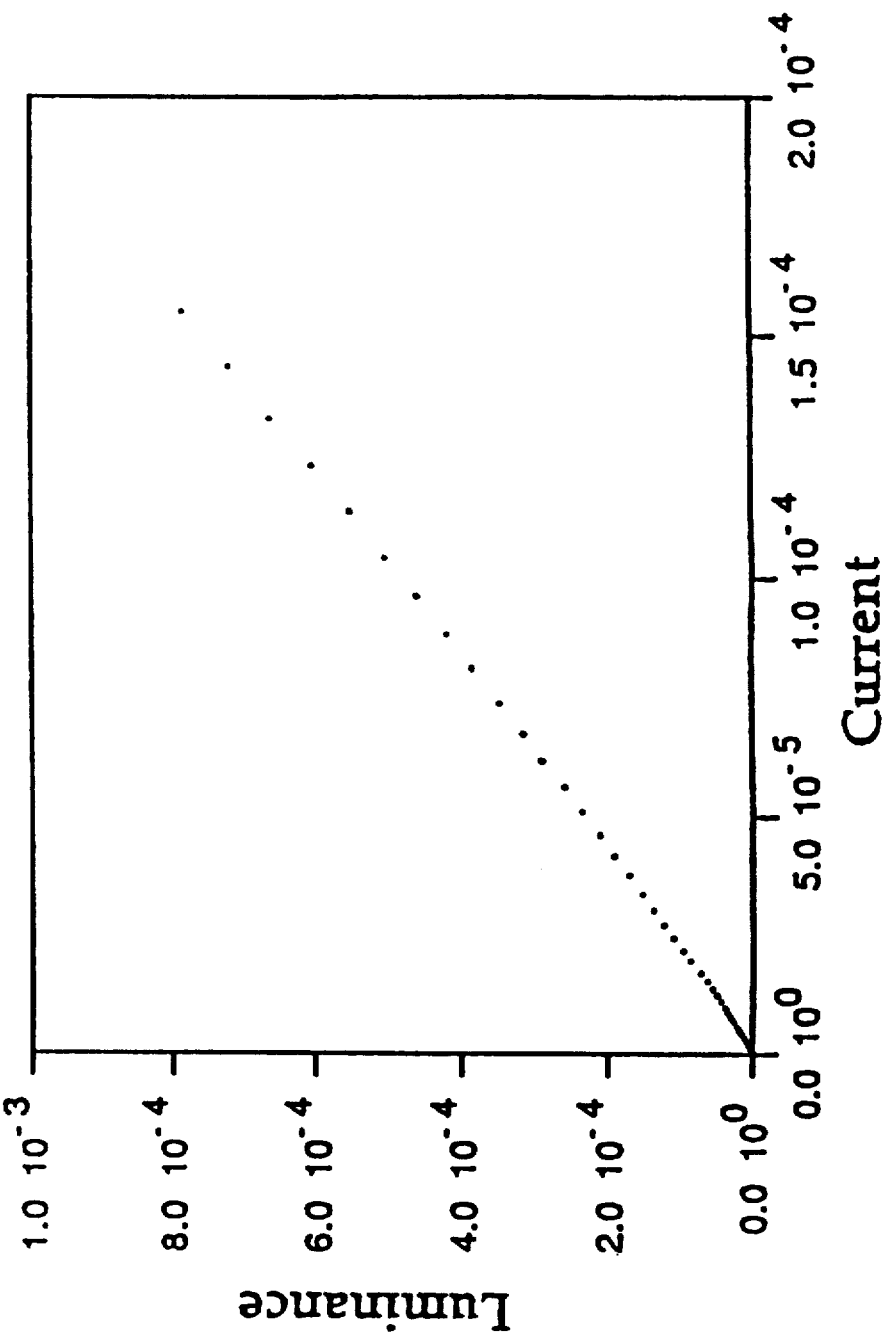
Figure 37A:
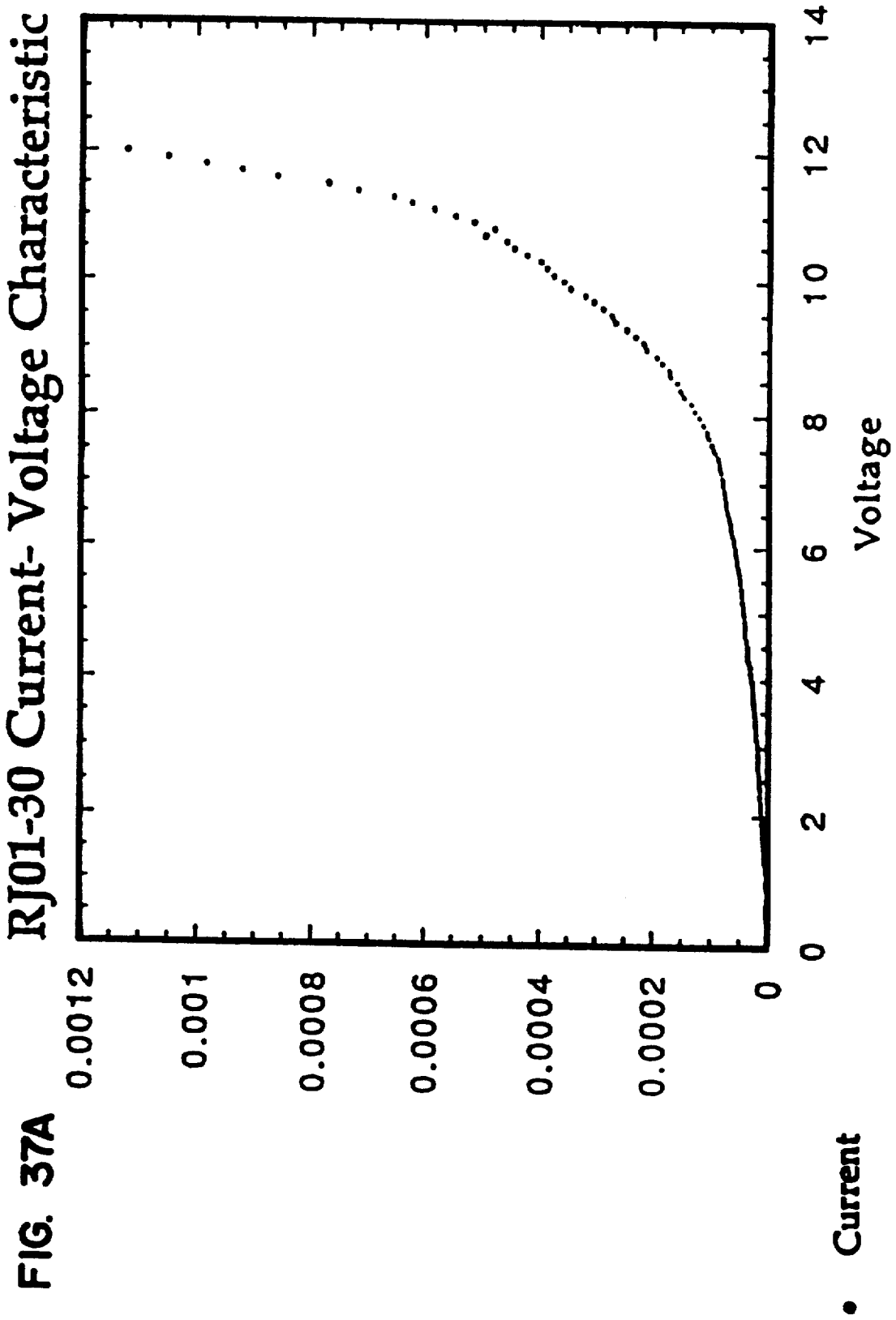
FIGS. 37 (a) and (b) are graphs showing respectively the current-voltage and luminance-current characteristics of MeO-leaving PPV as converted in vacuo at 300° for 12 hours on a substrate of ITO-coated glass and with aluminium as a cathode.

The performance of the device shows no deterioration over those made with PPV prepared via a THT leaving group precursor polymer with a turn on voltage below 10V, a diodic current-voltage characteristic and a largely linear current-luminance response and a slightly improved quantum efficiency by at least a factor of 2 (FIGS. 36 and 37).

The emission spectrum of the MeO-leaving PPV is markedly different with a peak emission at 2.5 eV compared with 2.25 eV in THT-leaving PPV. The emission is a bluey-green as opposed to a greeny-yellow in the case of the THT-leaving PPV. This is again consistent with the MeO-leaving PPV as converted being a copolymer of conjugated and unconjugated sequences: emission coming from the small conjugated sequences but at a higher energy than in fully conjugated PPV, (FIG. 37).

Thus by careful conversion conditions it is possible using copolymers of PPV to obtain electroluminescent emission of different colours and with improved efficiencies.

EXAMPLE 14

The random copolymers of PPV and DMeOPPV give a means to controlling the bandgap of a conjugated polymer and the potential for the construction of multicolour EL devices and channel waveguides.

The copolymers are prepared initially in a precursor form which is soluble in Methanol and consists of at least 3 distinct monomer units—a PPV precursor monomer unit with a THT-leaving group, a DMeOPPV monomer unit with a THT-leaving group and certainly a DMeOPPV monomer unit with a MeO-leaving group (formed by the methanolic solution substitutionally attacking the DMeOPPV THT-leaving units) as seen by the strong 1094 cm$^{-1}$ adsorption in the infrared absorption spectra of both the MeO-leaving homopolymer precursor of DMeOPPV and all the copolymer precursor polymers. There is possible a small amount of a fourth monomeric unit- a PPV monomer unit with a MeO-leaving group (formed by the methanolic solution substitutionally attacking the PPV THT-leaving units) (FIG. 39(a)).

Figure 40:
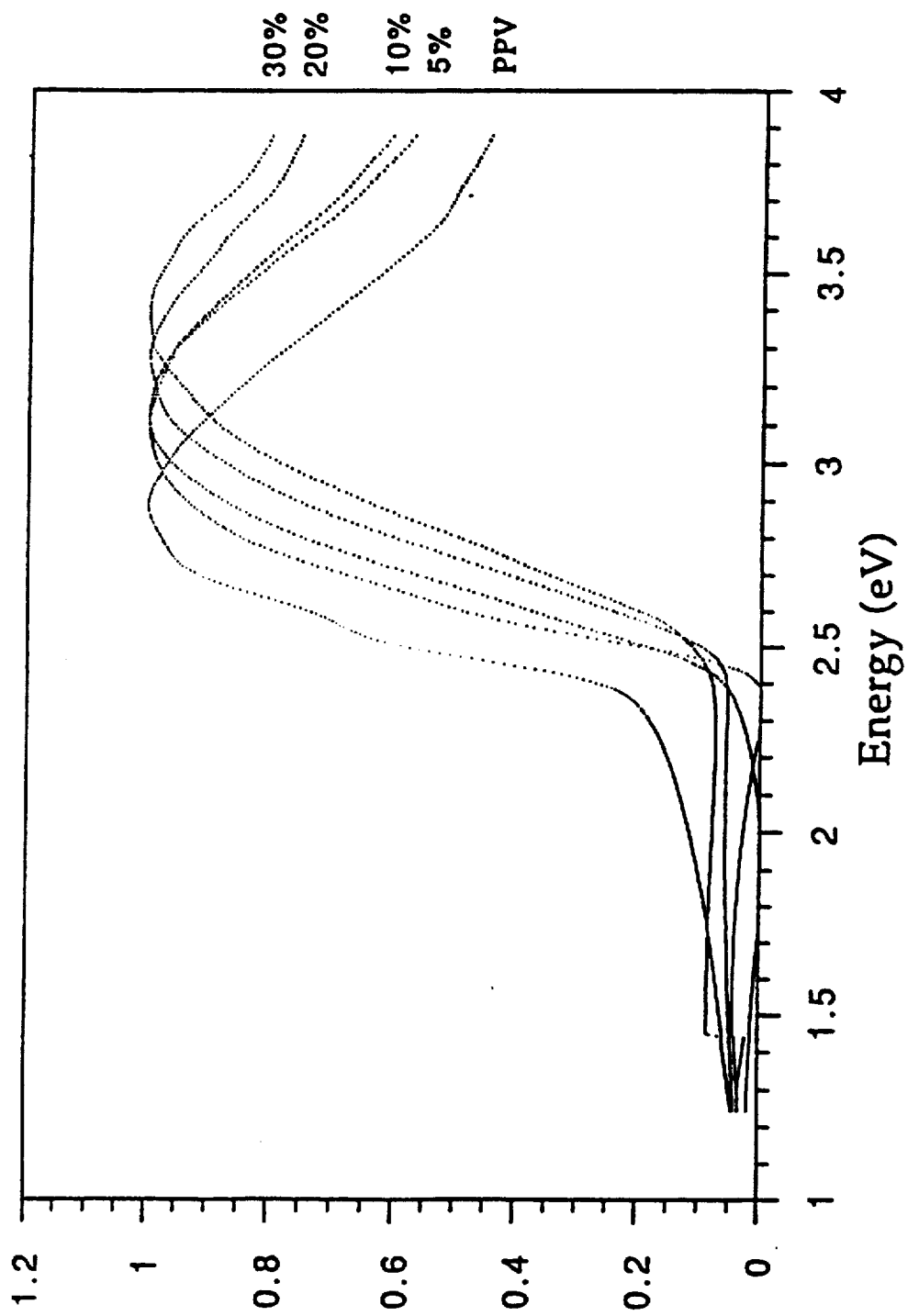
FIG. 40 is a graph showing the absorption spectra of spin-coated thin films of random copolymers of PPV and DMeOPPV after thermal conversion as converted in vacuo at 220° C. for 12 hours. The percentages on the figure represent the percentage of DMeOPPV monomer units w/w from which the precursor was formed.
Figure 41:
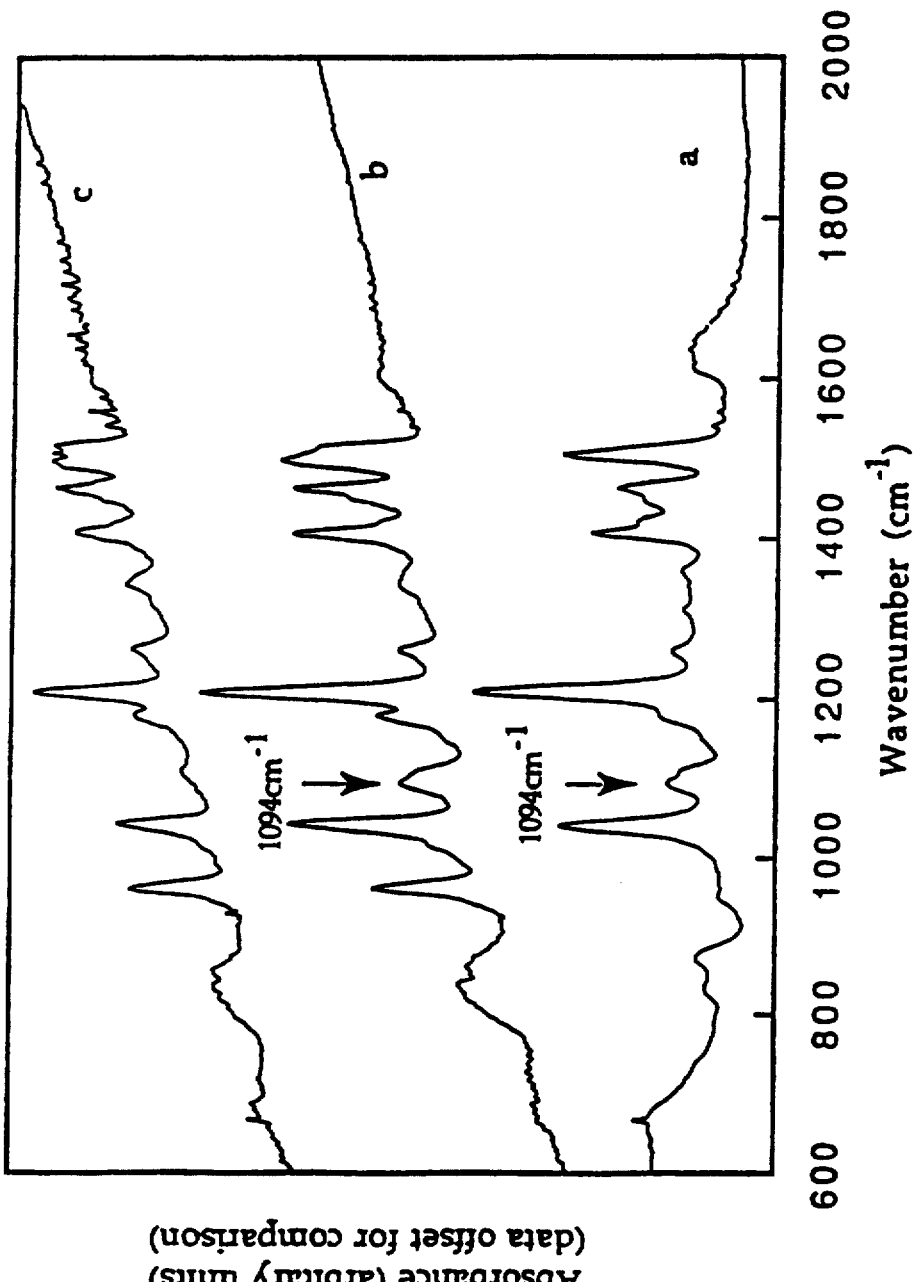

Thin films (of the order of 1000 Å as used in EL devices) of the copolymers can be obtained by spin-coating the precursor solutions. Thermal conversion of the said films gives mechanically and thermally robust films. It is found that by linearly varying the copolymer monomer unit ratio that the absorption edge of the converted copolymers may be accurately controlled (FIG. 40). Typically films are converted at 220° C. for 2 hours. More fully conjugated material has a lower bandgap. The controlled increase in bandgap with additional DMeOPPV to PPV units indicates an associated decrease in conjugation. FTIR data shows that the copolymers are only partially conjugated as converted (FIG. 41). There is still a significant absorption at 1094 cm$^{-1}$ indicating monomeric units of DMeOPPV with the methoxy leaving group have not been converted to the conjugated form leaving a copolymer of conjugated sequences and unconjugated sequences. The degree of conjugation will thus vary with the number of DMeOPPV Units present (FIG. 42).

To convert fully the homopolymer of DMeOPPV with the methoxy leaving group it is necessary to heat the precursor in the presence of acid to catalyse the loss of the methoxy group. As the THT-leaving group leaves, acid is also generated. Thus in the copolymers of PPV and DMeOPPV it is possible further to convert the monomeric units of DMeOPPV with the methoxy leaving group to the conjugated form, so lowering the bandgap further and giving more control of the bandgap, by methods of internally trapping the self produced acid where excess acid may damage electrodes or simply by heating the precursor films in the presence of acid.

By converting a spun-coated film of a copolymer at 220° C. in an argon flow which has been passed through concentrated HCl for 2 hrs it is clearly seen that the absorption bandgap of the polymer is shifted to lower energy over a similar film converted at 220° C. in vacuo indicating that the "acid" converted film is more fully conjugated. FTIR absorption measurements support this with the disappearance of the 1094 cm$^{-1}$ absorption only when the copolymer is "acid" converted. Again it is noted that 2 hours conversion by either technique gives stable material against further change (FIGS. 43 and 41).

By converting a spun-coated copolymer film on a glass substrate initially with a low temperature bake in vacuo at about 100° C. the diffusion rate of the acid ions out of the film is reduced giving an enhanced probability of causing conversion of methoxy-leaving units. A subsequent bake at 220° C. in vacuo yields fully stable material at room temperature again. A considerable reduction in bandgap is so obtained over material heated directly to 220° C. in vacuo. Thus there is a further method for controlling the bandgap of these materials (FIG. 44).

It should be emphasised that any method of controlling the bandgap in these conjugated polymers equally controls the colour of emitted light in an electroluminescent device (or the colour of photoluminescence under optical excitation) as the wavelength of the emitted light largely follows the bandgap of the material (an increase in the bandgap of the material causes a similar decrease in the wavelength of the emitted light). The spatial limit for this spatial control of bandgap across the polymer film is of the order of the thickness of the polymer film i.e. 1000 Å.

Another film of copolymer (30% Copolymer) was spun-coated onto a glass substrate and before thermal conversion 500A of Aluminium were vacuum deposited at a pressure of less than 6.10$^{-6}$ torr via a shadow mask. The sample was then baked in vacuo for 20 hours at 220° C. to facilitate full conversion. The sample was then etched in weak sodium hydroxide solution to remove the aluminium. The polymer film was unaffected by the etching process. However, the polymer is left patterned. Where the aluminium was, the polymer to the eye is a deeper orange colour indicating a greater degree of conjugation due to enhanced trapping of the acid ions in the polymer film by the aluminium. This is born out by the shift to lower energy of the absorption edge (FIG. 45) and the photoluminescence emission (FIG. 46) of the dark region originally covered by the aluminium. Thus the bandgap of the copolymers may again be controlled and moreover in different regions of the same film giving rise to the possibility of multicolour emission from a single EL device.

Such patterning also has an application in the manufacture of channel waveguides. Another such patterned device as above was made (from 10% copolymer) and there were the same associated lowering of bandgap and absorption edge where the aluminium had been etched from (FIG. 47) and lowering in energy of the photoluminescence emission from the same area (FIG. 48). The refractive indices of the two regions at 633 nm were measured by coupling light into the first TE modes from a He-Ne laser. The refractive index of the less conjugated material was measured to be 1.564 (0.002) and that of the more conjugated material (as converted under the encapsulation of aluminium) was measured to be 1.620 (0.002). This result is in keeping with simple dispersion theory for propagation of light in a dielectric medium such that the refractive index varies inversely with bandgap. Thus the patterning of the polymer allows also the spatial control of refractive index across a polymer film to a length scale of the order of 1000 Å. For typical waveguiding structures (such as a channel waveguide) it is necessary to define channels of material to a precision of the order but no smaller than the wavelength of the light to be guided (i.e. for the 633 nm emission from a He-Ne laser to a precision of the order of 6000 Å) with a higher refractive index than of the surrounding material. Clearly this method of patterning the copolymers of PPV and DMeOPPV is amenable to making waveguide structures as high refractive index regions can be defined to a size smaller than the wavelength of light which is to be confined in the high index region and guided.

Figure 3A:
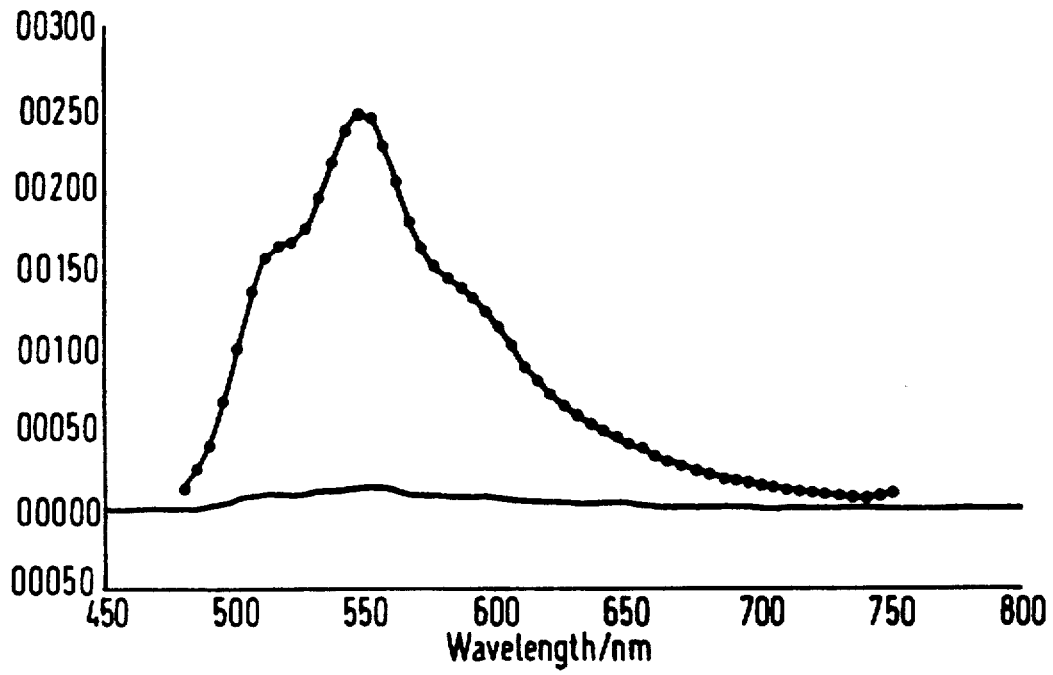
FIGS. 3a and 3b are graphs showing respectively the emission spectra for thin spin coated and thick solution cast films of a copolymer produced from a 1:9 molar ratio of dimethoxy-PPV and PPV monomer units respectively, converted at 220° C. in vacuo for two hours.
Figure 3B:
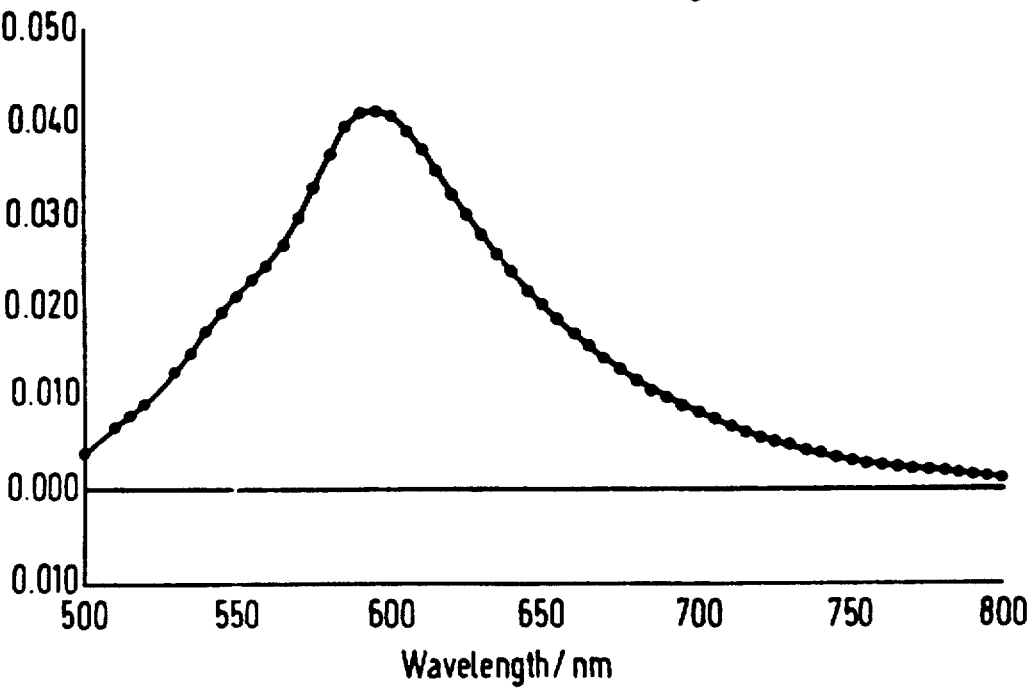
Figure 4A:
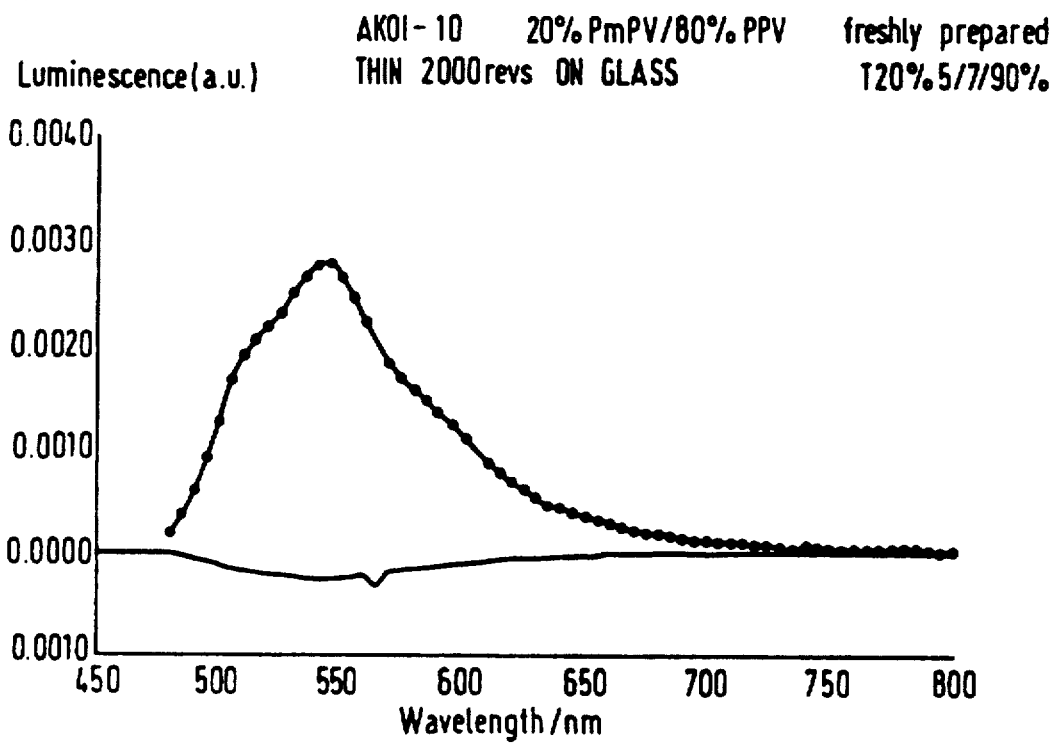
FIGS. 4a and 4b are graphs showing respectively the emission spectra for thin spin coated and thick solution cast films of a copolymer produced from a 1:4 molar ratio of dimethoxy PPV and PPV monomer units respectively, converted at 220° C. in vacuo for two hours.
Figure 4B:
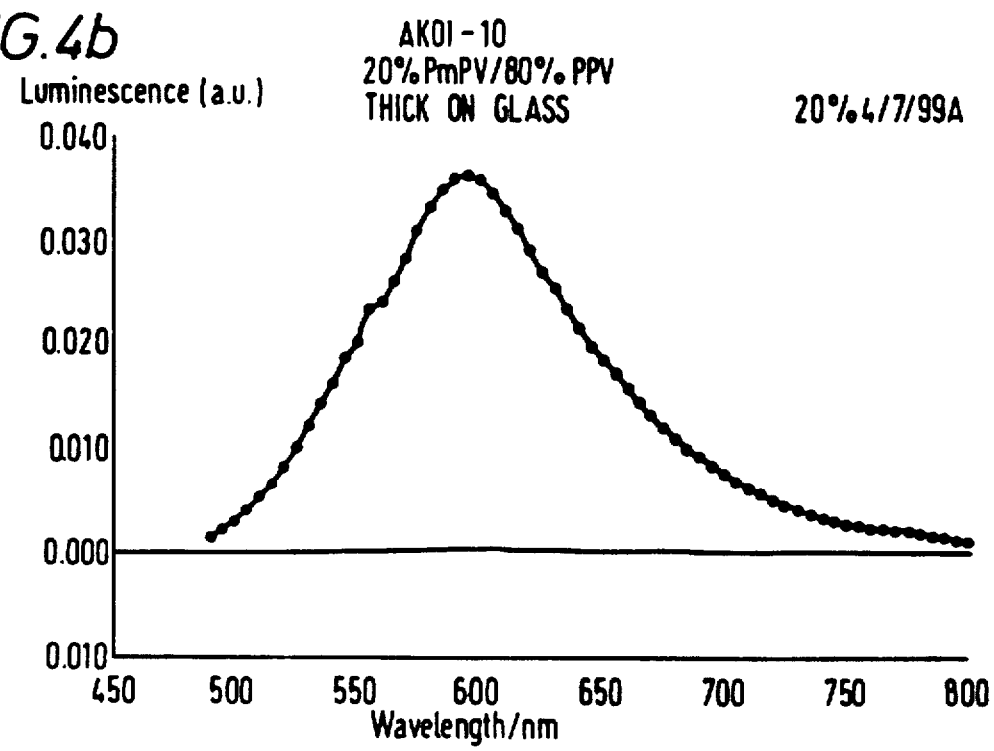
Figures 5A, 5B:
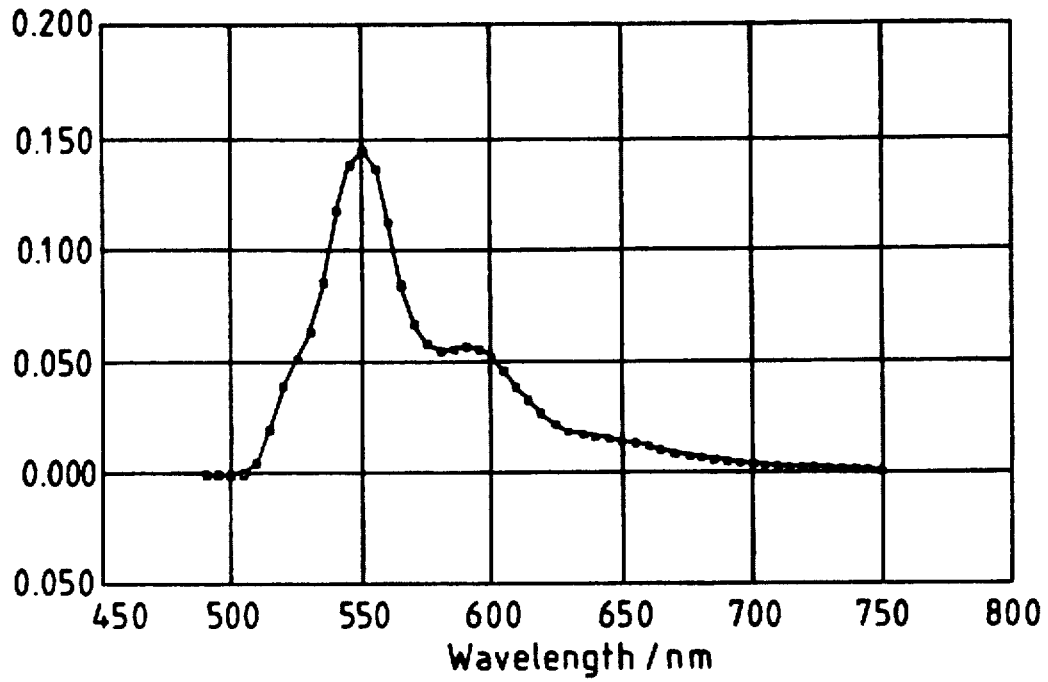
FIGS. 5a and 5b are graphs showing respectively the photoluminescence spectra for homopolymers of PPV and dimethoxy PPV.
Figure 19:
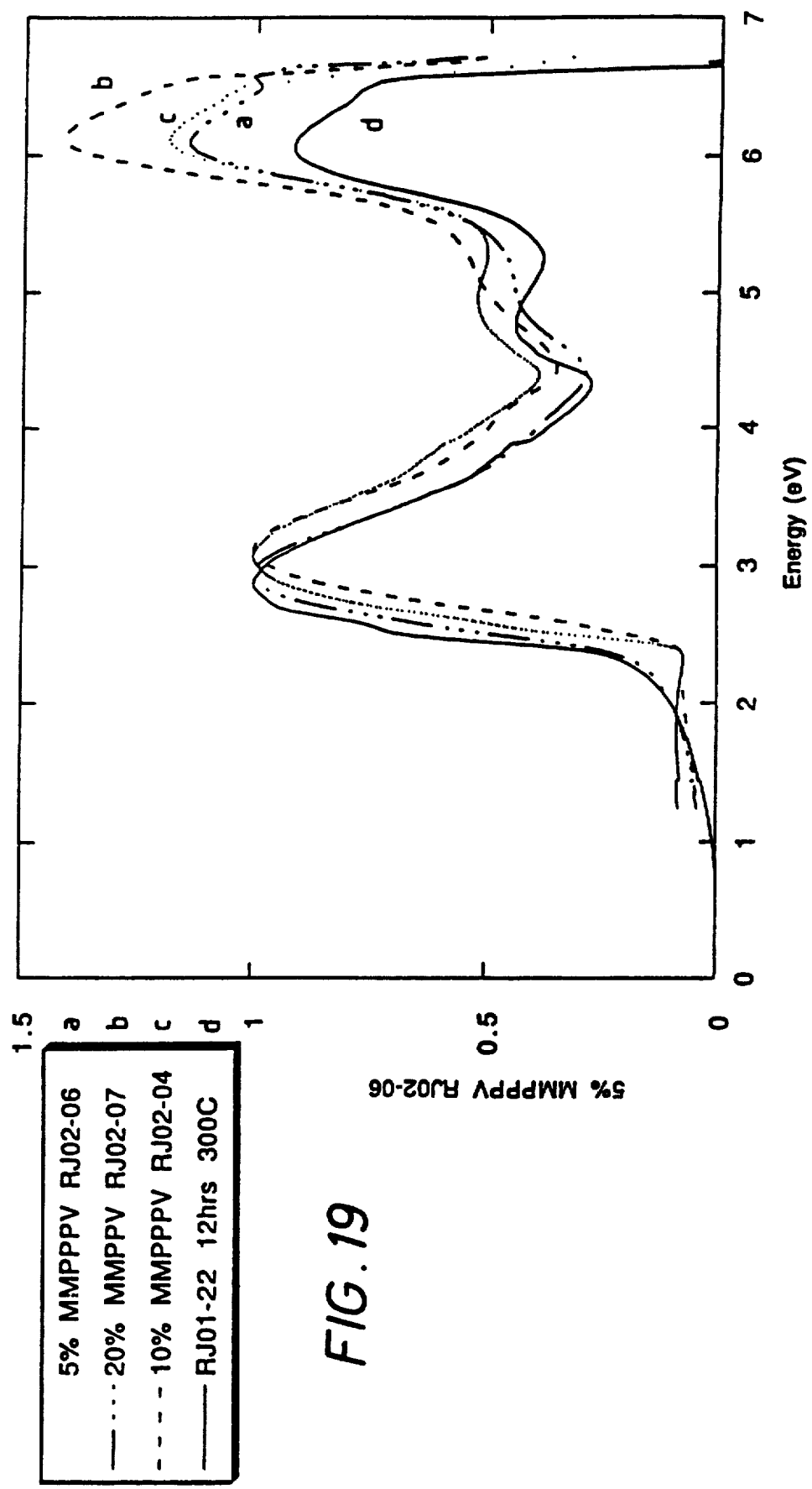
FIG. 19 are graphs showing the absorption spectra of spin-coated thin films of random copolymers of PPV and MMP-PPV produced from 80:20 (a), 90:10 (b), and 95:5 (c) and 100:0 (d) w/w ratios of PPV and MMP-PPV monomer units, respectively as converted at 220° C. in vacuo for 12 hours.
Figure 20:
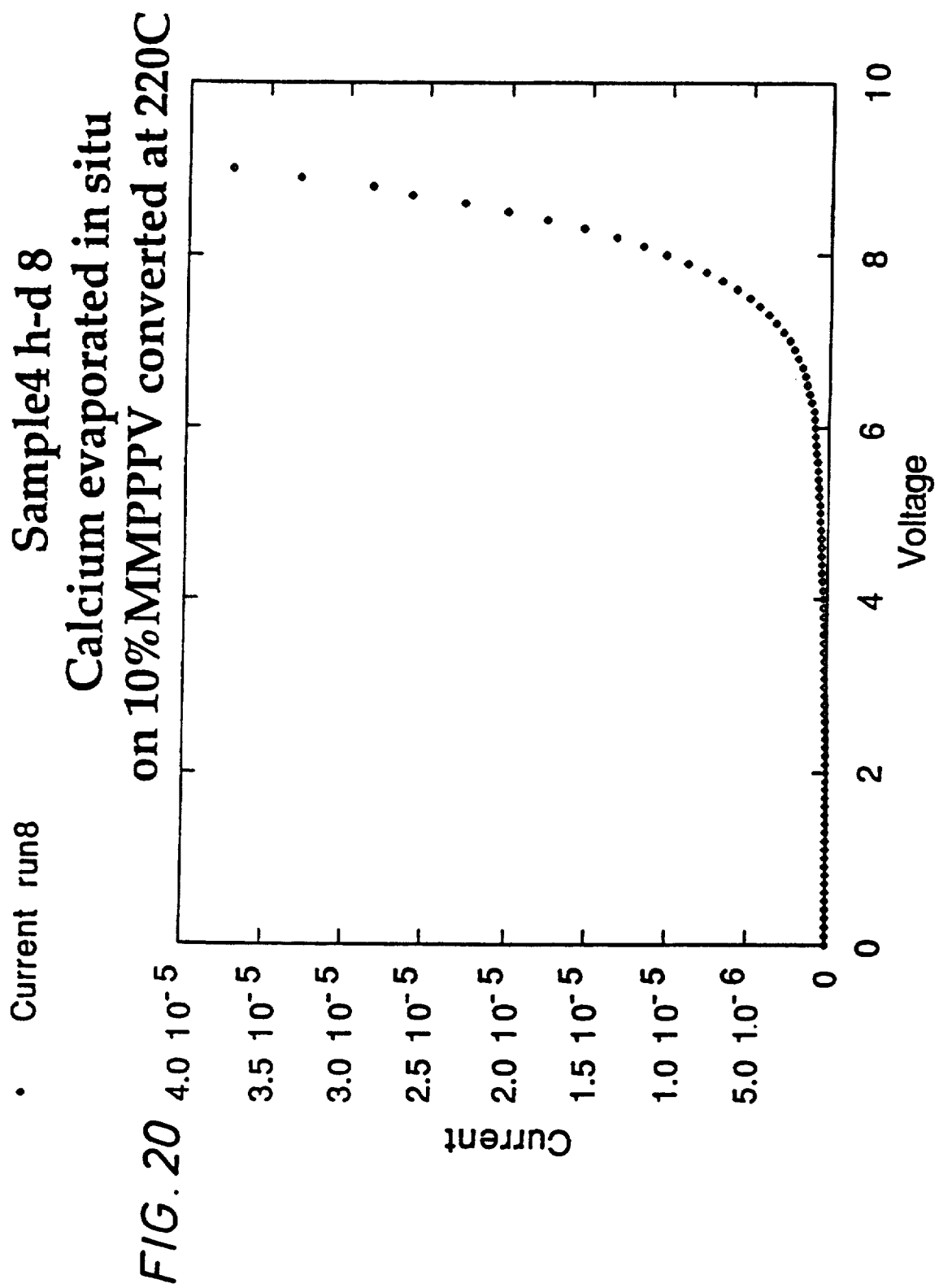
FIG. 20 is a graph showing the current/voltage characteristics of a thin film of a random copolymer of PPV and MMP-PPV produced from 90:10 w/w ratio of PPV and MMP-PPV monomer units as converted in vacuo at 220° C. for 12 hours on a substrate of ITO-coated glass and with calcium as a cathode.
Figure 21:
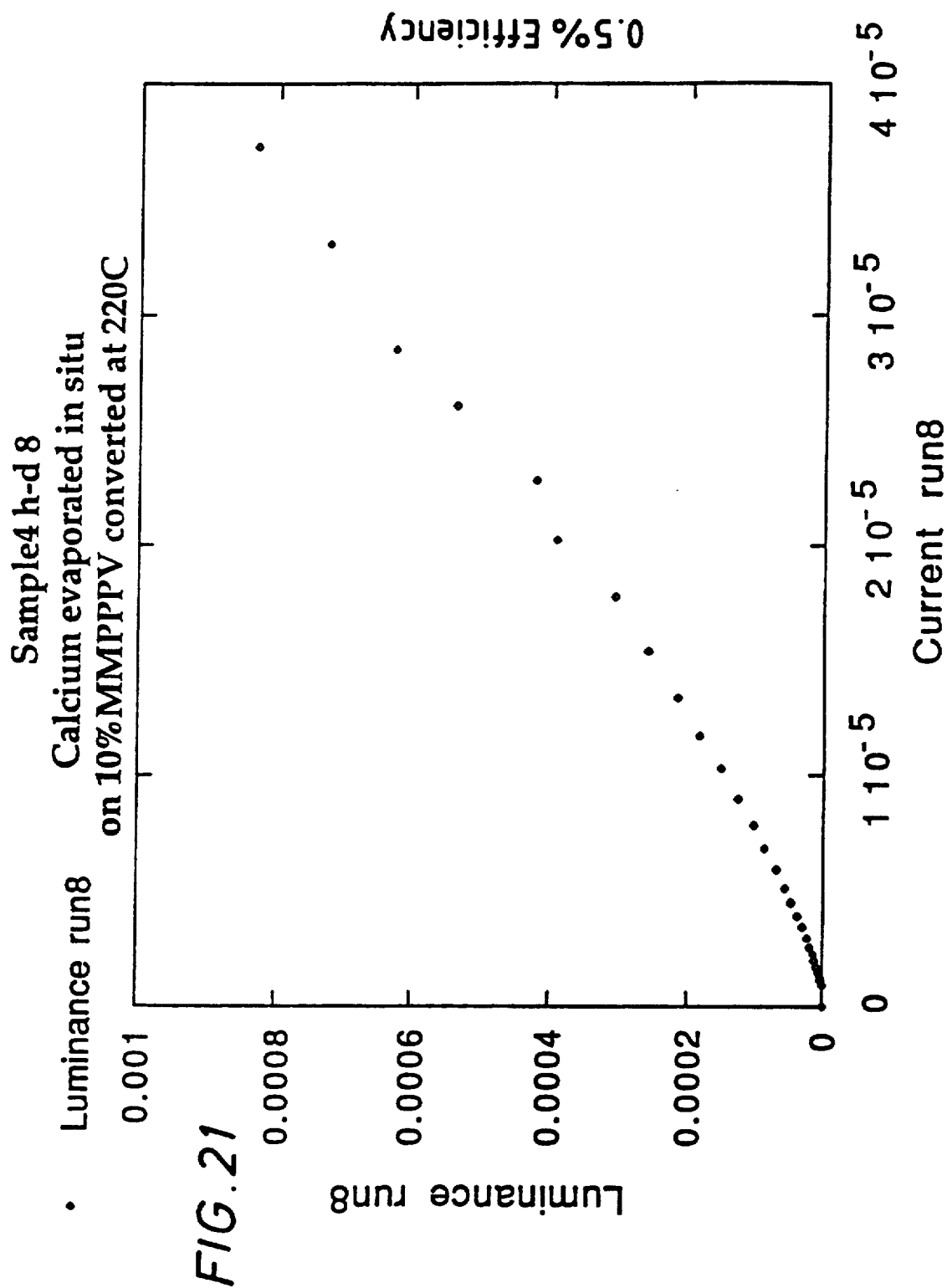
FIG. 21 is a graph showing the luminance/current characteristics of a thin film of a random copolymer of PPV and MMP-PPV produced from 90:10 w/w ratio of PPV and MMP-PPV monomer units as converted in vacuo at 220° C. for 12 hours on a substrate of ITO-coated glass and with calcium as a cathode.
Figure 23:
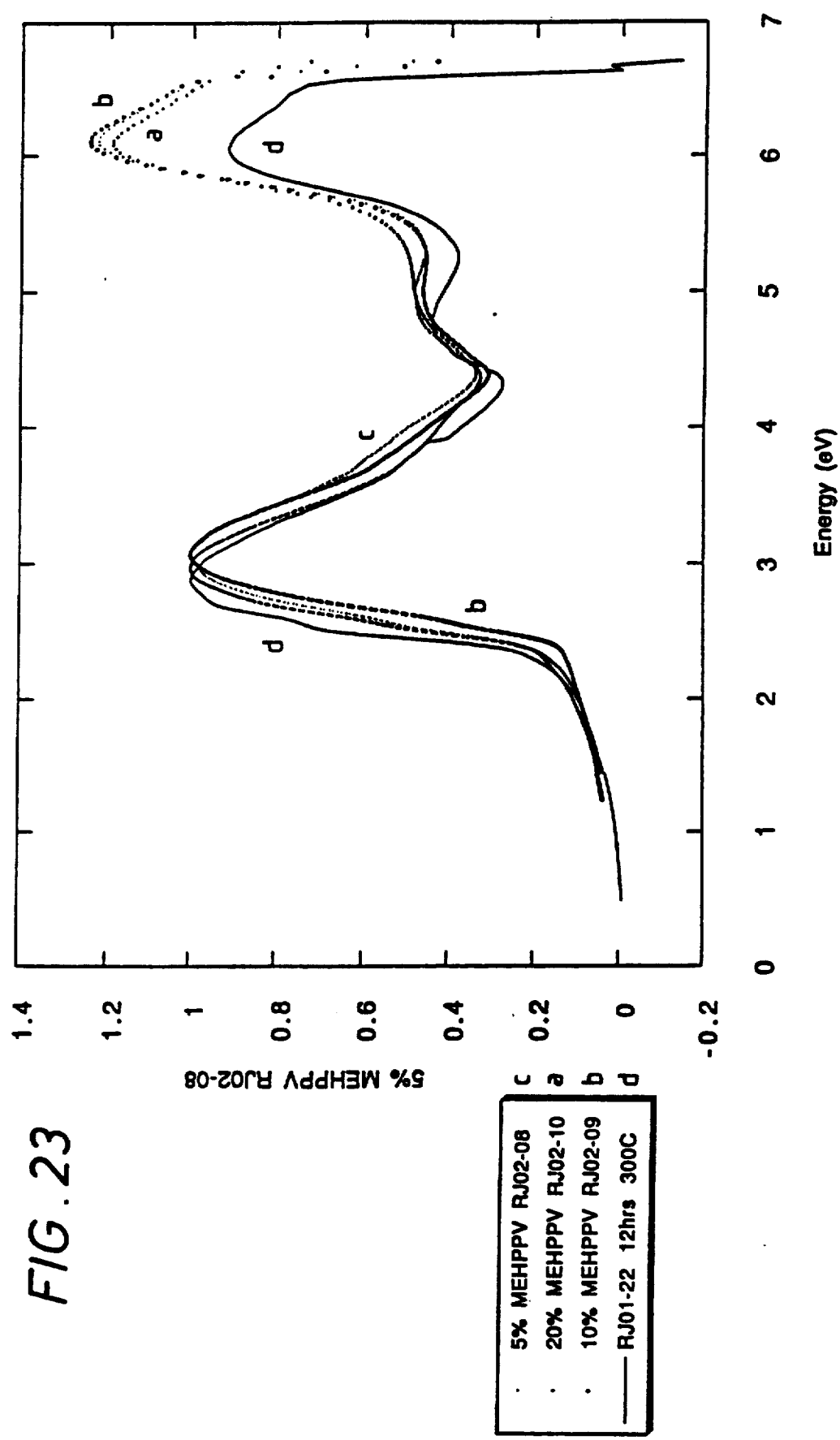
FIG. 23 are graphs showing the absorption spectra of spin-coated thin films of random copolymers of PPV and MEH-PPV produced from 80:20 (a), 90:10 (b), 95:5 (c) and 100:0 (d) w/w ratios of PPV and MEH-PPV monomer units, respectively as converted at 220° C. in vacuo for 12 hours.

In order to characterise more fully the nature of the resulting copolymers the absorption spectra were obtained from samples which had been spun onto glass under the same conditions as discussed below for the construction of devices (step (c)) and subsequently thermally converted side by side with the corresponding devices (step (d)). The results thus provide a direct insight into the effect upon the polymer electronic structure of the copolymer composition. FIG. 2a shows a set of spectra for the compositions of the copolymers (of general structure II with R=OCH$_3$) of para-phenylene vinylene, 2,5-dimethoxy-para-phenylene vinylene and unconverted precursor units that have been investigated in device structures and whose performance is exemplified below. The spectra have all been scaled to the same peak absorption to allow a ready comparison of the onsets for their $\pi$ to $\pi^*$ optical transitions and the energies of their absorption peaks. Also shown for comparison is the absorption spectrum of the PDMOPV homopolymer obtained as previously shown in "Polyarylene vinylene films prepared from precursor polymers soluble in organic solvents", S. Tokito et al, Polymer 31, 1137 (1990). There is a clear trend in these spectra that the energy of the absorption peak shifts to higher energy as the relative content, in the precursor copolymer (structure I with R=OCH$_3$ and R$^1$,R$^2$=—(CH$_2$)$_4$—), of units of the precursor to 2,5-dimethoxy-para-phenylene vinylene is increased. This behaviour is contrary to expectation for a fully conjugated copolymer since as discussed above and shown in FIGS. 2a and 2b, PDMOPV has a lower energy gap than PPV. In FIG. 2a, curve (a) is 100% PPV, (b) is 95% PPV/5% PDMOPV, (c) is 90% PPV/10% PDMOPV, (d) is 85% PPV/15% PDMOPV, (e) is 80% PPV/20% PDMOPV and (f) is 70% PPV/30% PDMOPV. Similarly this has been observed with 95% PPV/5% MMP-PPV, 90% PPV/10% MMP-PPV and 80% PPV/20% MMP-PPV (FIG. 19) and with 95% PPV/5% MEH-PPV, 90% PPV/10% MEH-PPV and 80% PPV/20% MEH-PPV (FIG. 23). The data is however consistent with incomplete conversion of the precursor units during the thermal treatment, resulting in remnant non-conjugated sequences that interrupt the electron delocalisation (structure II with R=OCH$_3$), limiting the effective conjugation length and thus increasing the $\pi$ to $\pi^*$ transition energy. These remnant sequences are mostly associated with the precursor to 2,5-dimethoxy-para-phenylene vinylene however, there can also be methoxy leaving groups associated with the precursor to PPV, i.e. the methoxy leaving group precursor polymer to PPV, which will not be fully eliminated by thermal treatment (structure II with R=OMe). The lack of conversion of the methoxy precursors to 2,5-dimethoxy-para-phenylene vinylene and to para-phenylene vinylene under the thermal conversion procedure utilised here is ascribable to the difficulty of elimination of the methoxy leaving group, previously shown in "Polyarylenevinylene films prepared from precursor polymers soluble in organic solvents" S. Tokito, T. Momii, H. Murata, T. Tsutsui and S. Saito, Polymer 31, 1137 (1990) to require acid catalysis for its full removal. It should be emphasised that while the conversion of the precursors to PPV does in fact liberate acid as one of its by-products, in thin film copolymer samples converted by heating in vacuo the acid is too rapidly removed to be effective in driving the conversion of the precursor to 2,5-dimethoxy-para-phenylene vinylene to completion. In thick film samples prepared by static solution casting, however, the extent of conversion of the methoxy precursors is significantly enhanced. This is clearly evidenced in their colour (they are unfortunately too thick for optical absorption measurements) which, unlike the uniformly yellow thin film samples, becomes increasingly red as the content of the precursor to 2,5-dimethoxy-para-phenylene vinylene in the copolymers increases. It is also evidenced by the decrease of the strength, during conversion, of the characteristic C—O stretch vibration in the infrared spectra that is associated with the methoxy modifier group on the benzylic carbon of the methoxy precursors to 2,5-dimethoxy-para-phenylene vinylene and para-phenylene vinylene. This behaviour can be understood as being due to the lower rate of loss of acid from the bulk of thick films, allowing greater interaction with the units of the methoxy precursors and consequently a greater extent of their conversion. Further evidence supporting these differences between the thin, spin-coated films and thicker solution cast films comes from their photoluminescence spectra. Discussion here is limited to the representative cases of the copolymers obtained following thermal conversion of thin spin-coated and thick solution cast films of the copolymer precursors prepared from (1) 10% of units of the precursor to 2,5-dimethoxy-para-phenylene vinylene/90% of units of the precursor to para-phenylene vinylene and (2) 20% of units of the precursor to 2,5-dimethoxy-para-phenylene vinylene/80% of units of the precursor to para-phenylene vinylene. In FIGS. 3(a) and (b) are shown respectively the emission spectra for thin spin-coated and thick solution cast films for case (1). In FIGS. 4(a) and (b) are shown the corresponding spectra for case (2). For comparison FIGS. 5(a) and (b) show the photoluminescence spectra for the PPV and PDMOPV homopolymers; the latter prepared via acid catalysed thermal conversion under HCl containing nitrogen gas flow so as to ensure substantial, if not wholly complete, conversion of the precursor units. It is immediately clear from the spectra in FIGS. 3 and 4 that in vacuo thermally converted spin-coated thin films have significantly different emission spectra to the thicker films obtained under identical conversion conditions and from the same precursor solutions but following static solution casting. Furthermore, whilst the spectra of the thin spin-coated samples have spectra which lie at higher energy than in PPV (FIG. 5(a)), the thicker static solution cast samples show spectra that are red shifted relative to PPV and hence that are shifting towards the emission spectrum seen in PDMOPV (FIG. 5(b)).

It is thus clear that the electronic structures of the copolymers that are incorporated into device structures may be controlled by the selection of the constituent components present in the copolymer precursor and by the conversion conditions used in device fabrication. Changing some of the units of the precursor to para-phenylene vinylene to units of the precursor to 2,5-dimethoxy-para-phenylene vinylene can have two different effects depending on whether conversion is purely thermal or also involves acid catalysis. For purely thermal conversion there is an incomplete elimination such that the resultant conjugated segments are separated by remnant non-conjugated precursor units, causing the energy gap to increase relative to that of homopolymer PPV and the photoluminescence emission to be blue shifted, occuring at higher energy than in PPV. For acid catalysed thermal conversion the elimination is substantially complete with the result that the energy gap decreases and photoluminescence emission shifts to the red.

Figure 6:
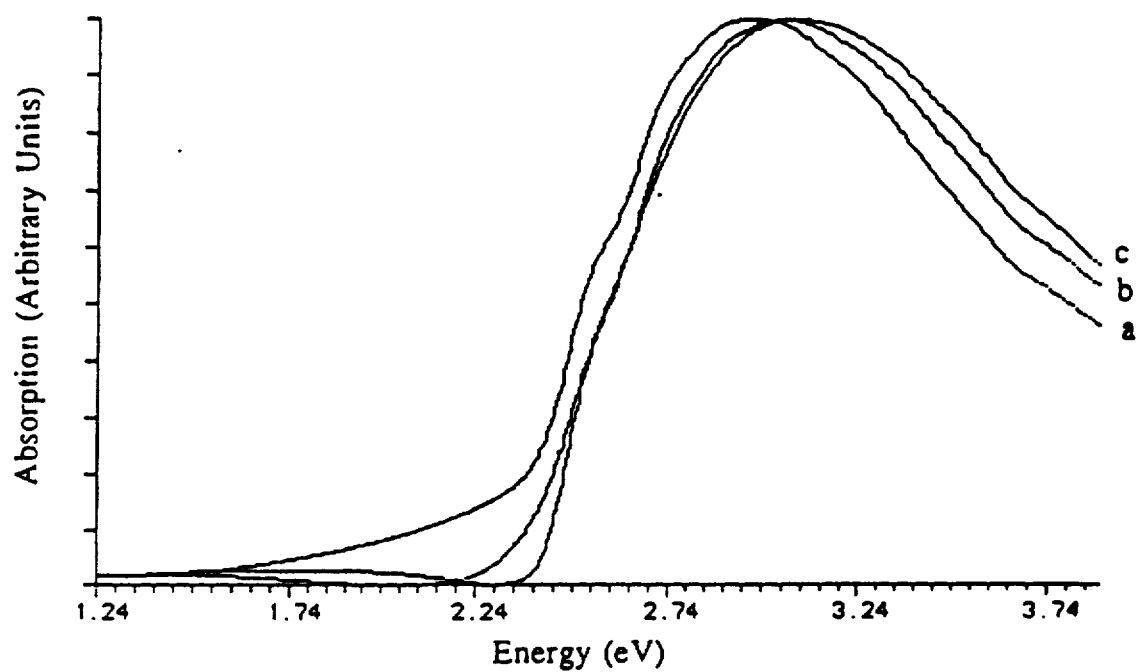
FIG. 6 are graphs showing respectively the absorption spectra of a homopolymer of PPV (a), and random copolymers of PPV and PTV produced respectively from 19;1 (b) and 9:1 (c) molar ratios of PPV and PTV monomer units, converted at 220° C. in vacuo for two hours.
Figure 7A:
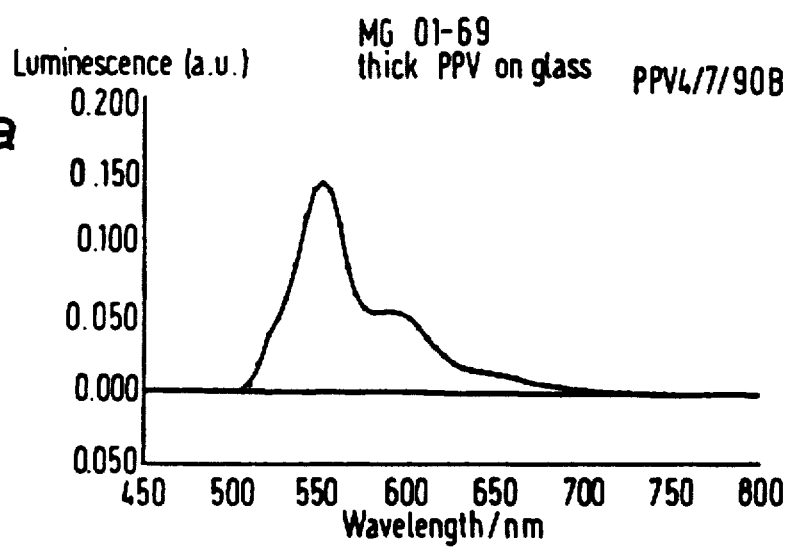
FIGS. 7a, b and c are graphs showing respectively the photoluminescence emission spectra for thick free cast films of a homopolymer of PPV; a copolymer produced from a 19:1 molar ratio of PPV and PTV monomer units respectively; and a copolymer produced from a 9:1 molar ratio of PPV and PTV monomer units respectively.
Figure 7B:
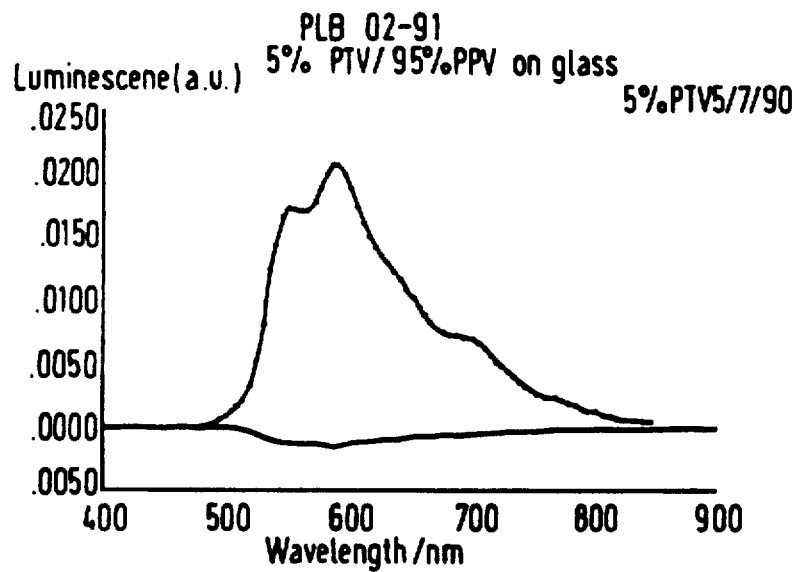
Figure 7C:
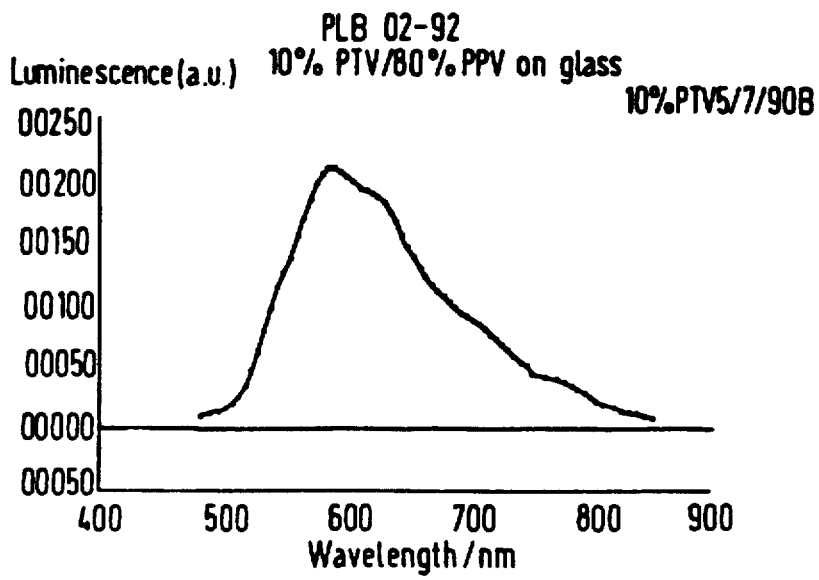

A similar situation arises in the case of the copolymers of the precursor to para-phenylene vinylene and the precursor to 2,5-thienylene vinylene (structure II with R=H and R'—CH₃) with the absorption spectra of thin spin-coated films of in vacuo thermally converted copolymers showing a shift in the position of the absorption peak to higher energy than seen in PPV (see FIG. 6) whilst the photoluminescence emission spectra for thick solution cast films converted under identical conditions show a red shift relative to that in PPV (see FIGS. 7 (a), (b) and (c)). In FIG. 6, curve (a) is 100% PPV, (b) is 95% PPV/5% PTV and (c) is 90% PPV/10% PTV. Thus, the conversion of methoxy modifier group precursor units of 2,5-thienylene vinylene is enhanced in thick films by acid catalysed elimination driven by the acid by-product of the para-phenylene vinylene sulphonium-salt-precursor conversion. It was previously reported in "Optical Excitations in Poly(2,5-thienylene vinylene)", A. J. Brassett, N. F. Colaneri, D. D. C. Bradley, R. A. Lawrence, R. H. Friend, H. Murata, S. Tokito, T. Tsutsui and S. Saito, Phys. Rev. B 41, 10586 (1990) that the photoluminescence emission from the PTV homopolymer obtained by acid catalysed thermal conversion of the methoxy leaving group precursor polymer is extremely weak (with quantum yield less than or of order $10^{-5}$) and, when it can be observed, appears at energies above the onset for $\pi$ to $\pi^*$ optical transitions.

Figure 8:
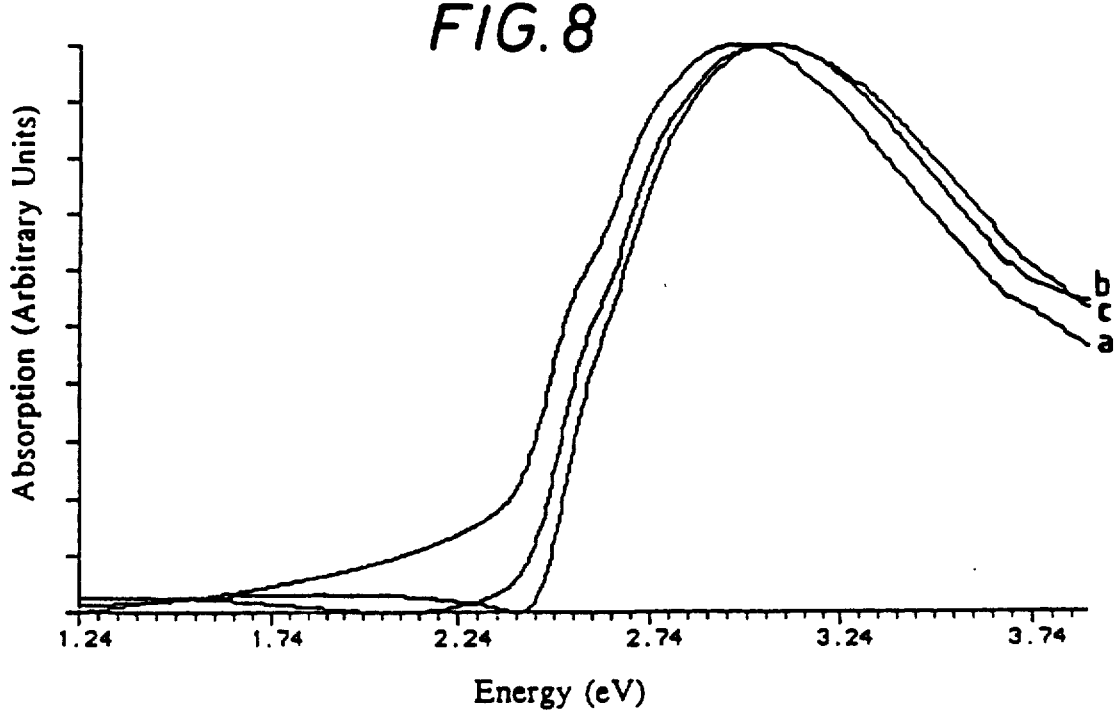
FIG. 8 are graphs showing the absorption spectra of spin-coated thin films of a homopolymer of PPV (a), and random copolymers of PPV and dimethyl PPV produced respectively from 19;1 (b) and 9:1 (c) molar ratios of PPV and PTV dimethyl monomer units as converted at 220° C. in vacuo for two hours.
Figure 9A:
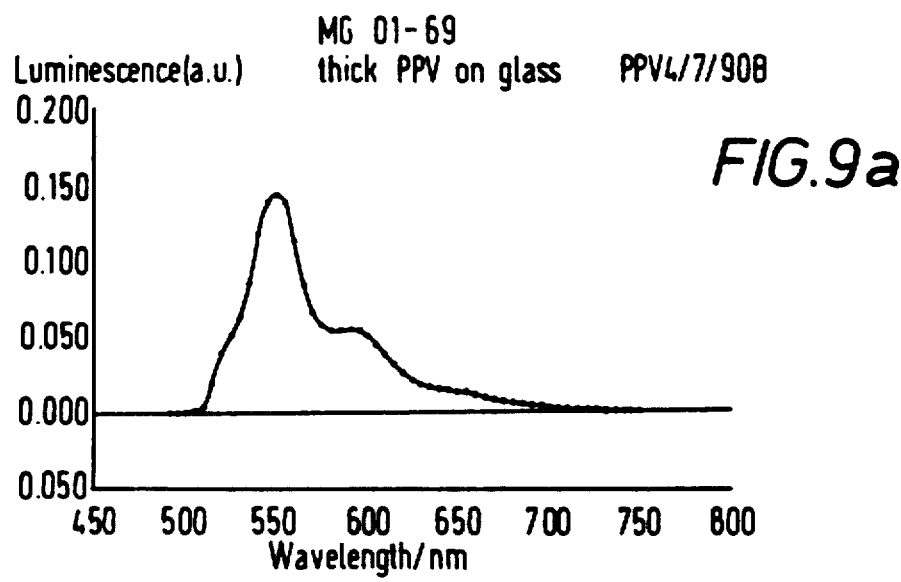
FIGS. 9a, b and c are graphs showing respectively the photoluminescence emission spectra of thick free cast films for the homopolymer of PPV; a copolymer produced from a 19:1 molar ratio of PPV and dimethyl PPV monomer units respectively; and a copolymer produced from a 9:1 molar ratio of PPV and dimethyl-PPV monomer units respectively.
Figure 9B:
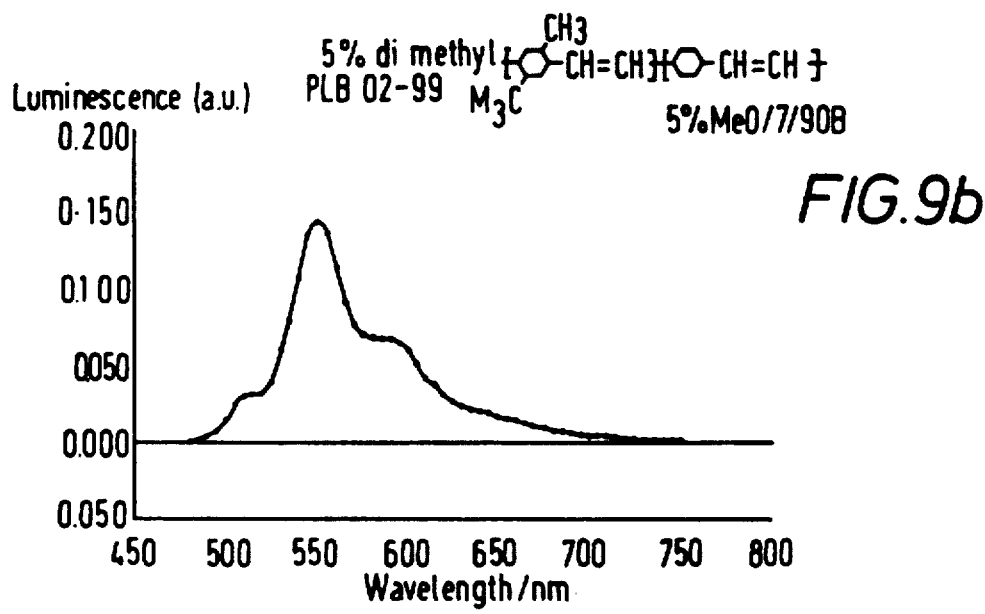
Figure 9C:
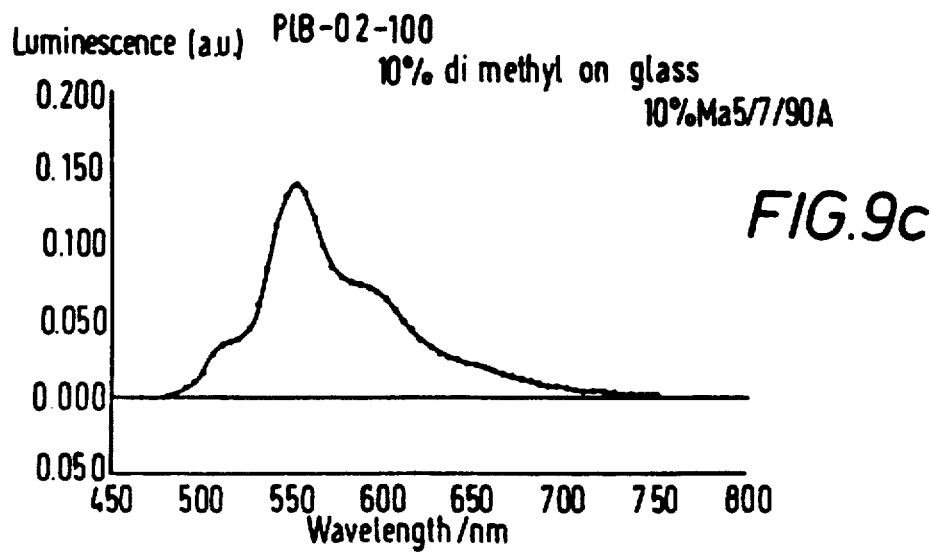

In the copolymers of the precursors to para-phenylene vinylene and 2,5-dimethyl-para-phenylene vinylene (structure (I) with $R=OCH_3$ and $R^1,R^2=-(CH_2)_4-$) the absorption spectra of in vacuo thermally converted thin spin-coated samples show a shift in the position of the absorption peak to higher energy than seen in PPV (see FIG. 8) whilst the photoluminescence emission spectra for thick solution cast films converted under identical conditions show little shift relative to that in PPV (see FIGS. 9(a), (b) and (c)). In FIG. 8, curve (a) is 100% PPV, (b) is 95% PPV/5% DMPPV and (c) is 90% PPV/10% DMPPV. The explanation of the higher bandgap energy obsrved in the absorption spectra of the thin spin-coated samples is that the as-formed copolymer contains disruption in the conjugation due either to steric interactions of the methyl group with the vinylic proton twisting the sp²-$\pi$-orbitals of the dimethyl-para-phenylene and the adjacent vinylene units out of planarity or that in the absence of acid catalysed conversion, the elimination of methoxy leaving groups from the methoxy precursors to 2,5-dimethyl-para-phenylene vinylene and para-phenylene vinylene is incomplete, thus resulting in a copolymer structure containing conjugated segments separated from each other by unconverted non-conjugated precursor units or a combination of both.

The inventors have trapped some of the acid released from a thin film during thermal conversion by capping a section of a film of the 10% dimethoxy-PPV/90% PPV precursor polymer which had been spin coated onto a glass slide (about 2.5 cm square) with a strip of evaporated aluminium (about 4 mm wide) before heat treatment. The precursor was then heated as described above to leave a film of thickness 100 nm and the aluminium was removed using dilute aqueous sodium hydroxide. There was a clear difference in colour between the area previously coated with aluminium (orange) and that where there had been no aluminium (yellow). The optical absorption spectra for the two areas are shown in FIG. 16 from which it can be seen that there is a shift in band gap towards the red of about 0.2 eV for the area previously coated with aluminium. The photoluminescent spectra for the two regions are shown in FIG. 17.

This shows that we can control the extent of conjugation in different regions of the same polymer film so as to produce different emission colours from these different regions.

Fabrication of Electroluminescent (EL) structures

Structures for an EL device require two electrodes to either side of the emissive region. For the examples shown here, devices have been fabricated by deposition of a series of layers onto a transparent substrate (glass), but other structures can also be made, with the active (i.e. emissive) area being defined by patterning within the plane of the polymer film.

The choice of electrode materials is determined by the need to achieve efficient injection of charge carriers into the polymer film, and it is desirable to choose materials which preferably inject electrons and holes as the negative and positive electrodes respectively. In International Patent Application No. PCT/GB90/00584 (Publication No. PCT/WO9013148) is described the use of PPV as the emissive layer, and a choice of aluminium, amorphous silicon, silver/magnesium alloy as the negative electrode, and aluminium with a thin oxide coating, gold and indium oxide as the positive electrode. Many of these combinations were found to be satisfactory. In the present disclosure, where many different compositions of copolymers have been investigated, the choice of contact layers has been generally for convenience that of aluminium for the negative electrode and aluminium with an oxide coating as the positive electrode. Calcium has also been used as the negative electrode with indium/tin oxide as the positive electrode. It is to be expected that results obtained with this combination give a good indication of the behaviour to be expected with other choices for electrode materials:

The procedure used for all devices used in this work is as follows:

(a) Clean glass substrates (microscope slides) in propan-2-ol reflux.

(b) Deposit bottom contact of aluminium by evaporation of aluminium in a standard vacuum evaporator (base pressure $2 \times 10^{-6}$ mbar). Four strips 1 mm wide were usually deposited, and the aluminium film thickness was chosen to give a conducting but semi-transparent film (9–12 nm). The aluminium was then exposed to air at room temperature, to allow formation of a surface oxide coating.

(c) Deposition of the precursor polymer from solution in methanol by spin-coating, using a Dyna-Pert PRS14E spin-coater. This was performed inside a laminar-flow cabinet, with a spin speed of 2000 rev/min, and produced films of polymer in the thickness range 50–150 nm.

(d) Thermal treatment of the precursor, to convert to the conjugated polymer. This was carried out in an evacuated oven (base pressure $10^{-5}$ mbar) inside an argon-atmosphere glove box. The heat treatment used was 30 min to heat to 220° C. between 2 and 5 hours at 220° C., and 3 hours to cool to room temperature.

(e) Evaporation of aluminium top contact, carried out as in (b) above, but with the 1 mm wide strips rotated by 90°, to give a total of 16 independently addressable devices, each 1 mm². The aluminium thickness here was typically 50 nm, to ensure a good coverage, and to provide some encapsulation to keep oxygen away from the active parts of the device.

Measurements of Devices

Positive bias was applied to the bottom contact (aluminium with surface oxide coating) using a programmable voltage source (Keithley model 230). The current through the device was measured with a Keithley model 195 DVM connected between the top contact and ground. The light output was measured with a large area silicon photovoltaic cell (1 cm² active area, Radio Spares catalogue number RS 303-674).

Figure 10A:
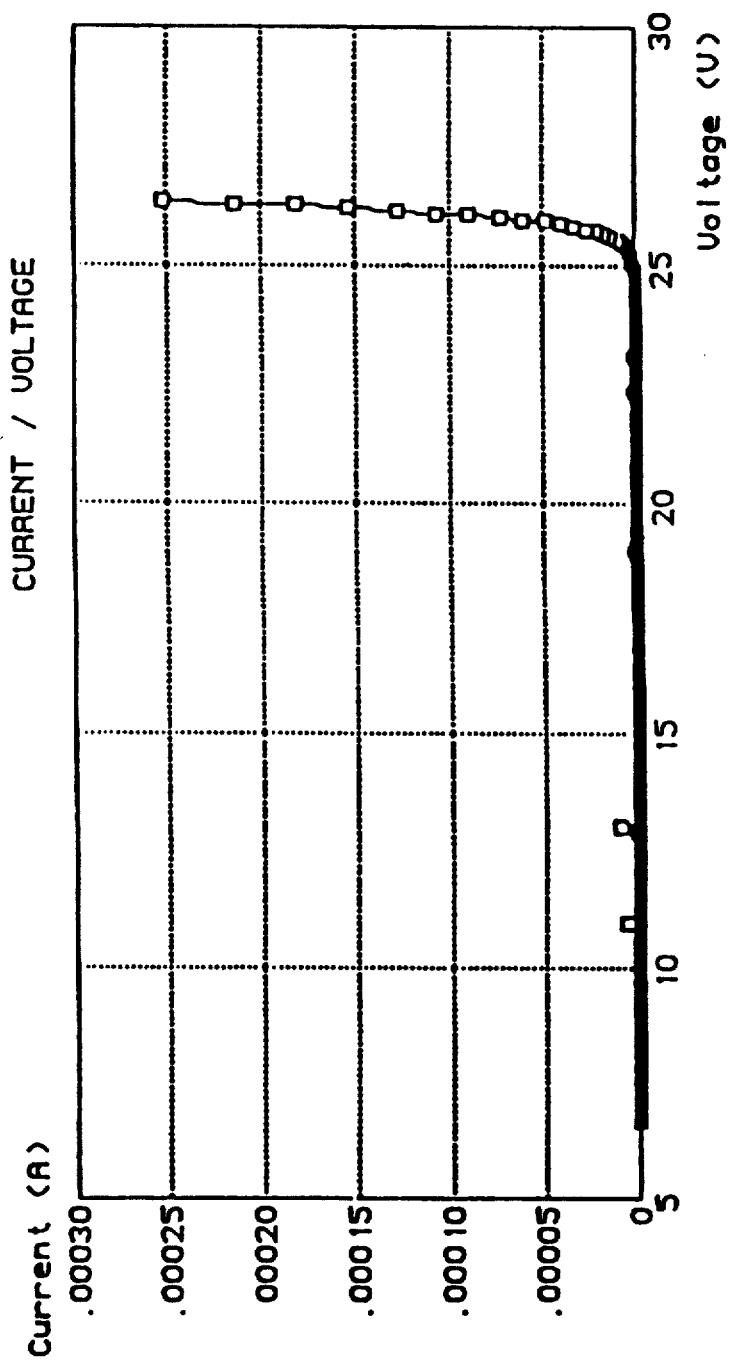
FIGS. 10a, 11a and 12a are graphs showing the current/voltage characteristics of a thin film of respectively PPV; a copolymer produced from a 9:1 molar ratio of PPV and dimethoxy PPV monomer units respectively; and a copolymer produced from a 9:1 molar ratio of PPV and thienylene vinylene monomer units respectively, the polymer films being spin-coated and converted at 220% for two hours in vacuo with hole injecting electrodes of oxidised aluminium, and with electron injecting electrodes of aluminium.
Figure 11A:
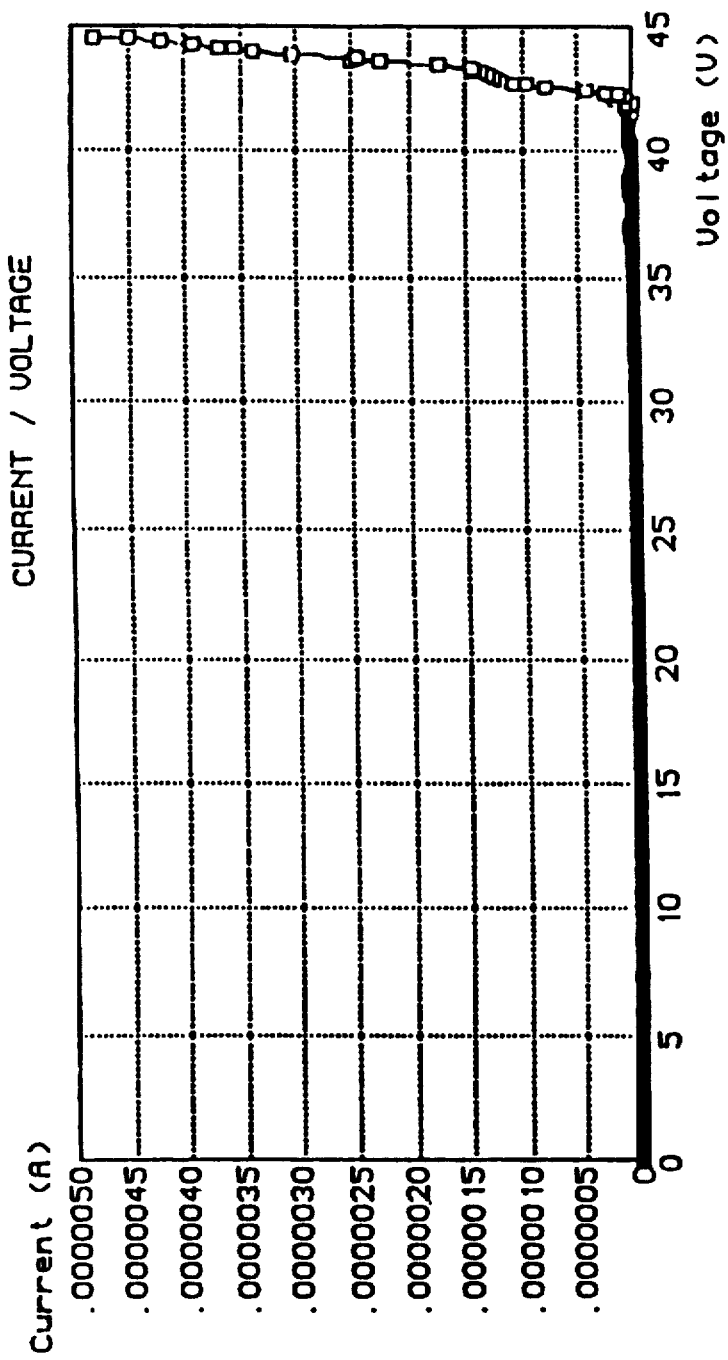
Figure 12A:
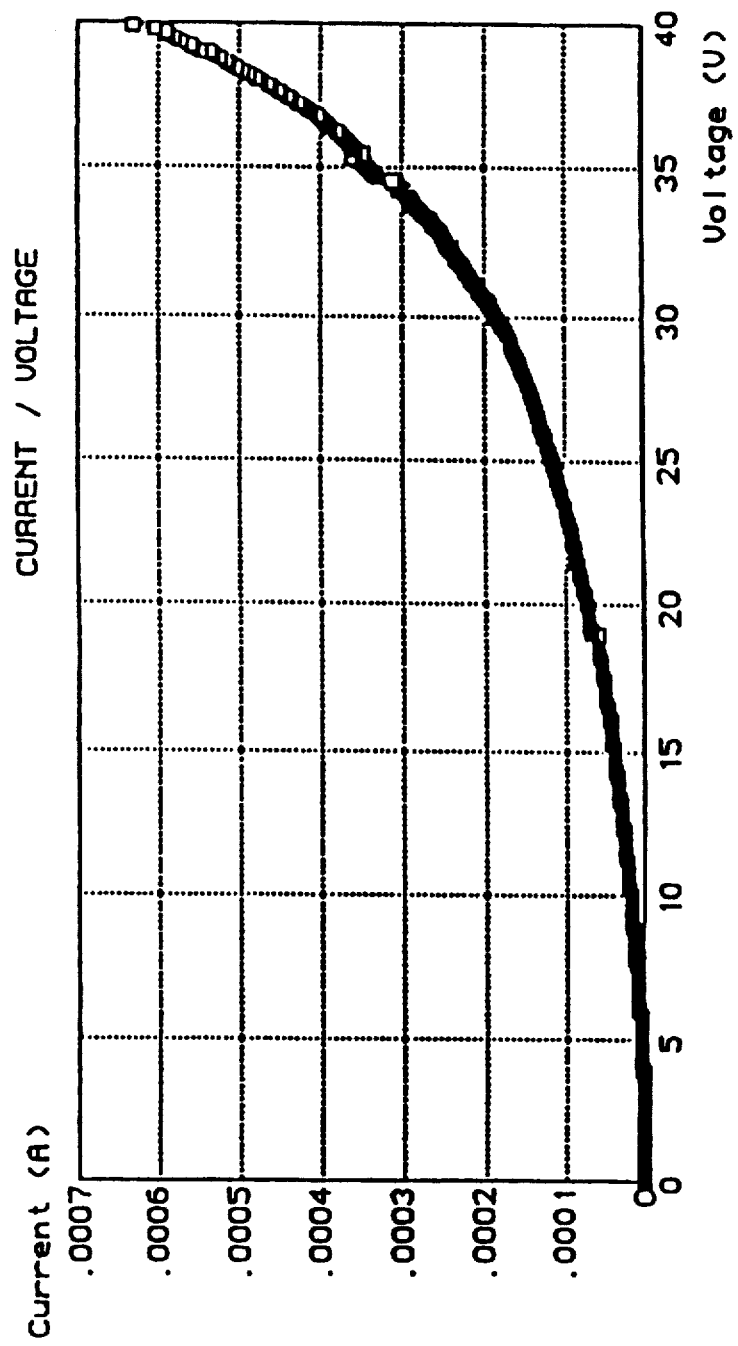
Figure 12B:
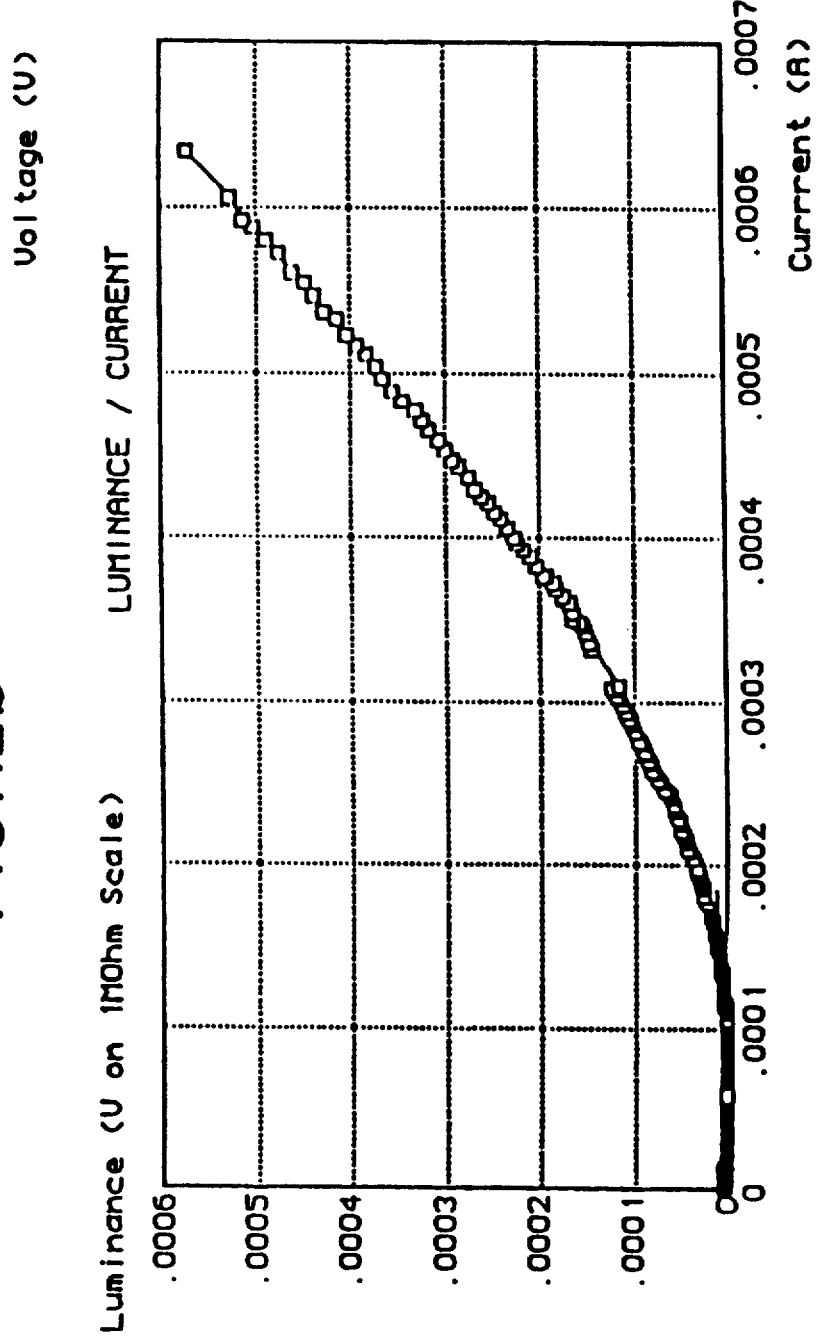
Figure 13:
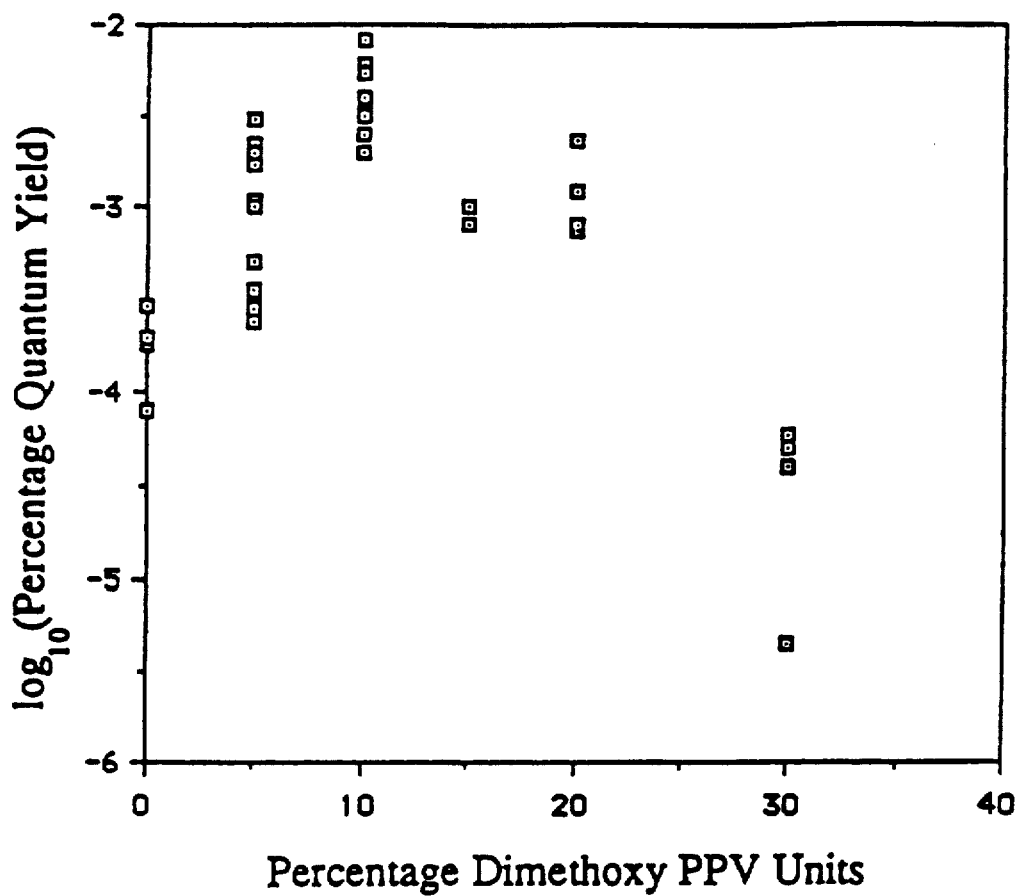
FIG. 13 illustrates the electroluminescent quantum yield of random copolymers formed from PPV and dimethoxy-PPV monomer units as measured in thin film structures with hole injecting electrodes of oxidised aluminium, a spin-coated film converted at 220° C. in vacuo for two hours, and with electron injecting electrodes of aluminium.
Figure 14:
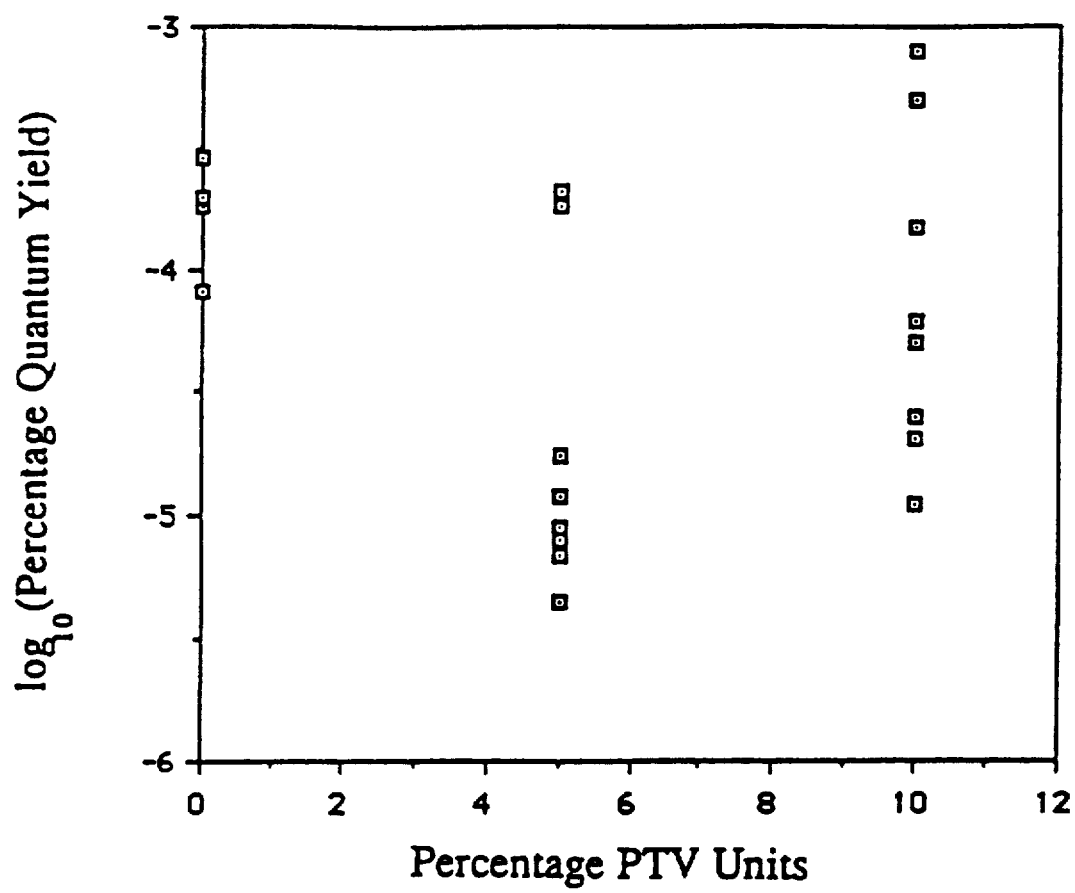
FIG. 14 illustrates the electroluminescent quantum yield of random copolymers formed from PPV and PTV monomer units as measured in thin film structures with hole injecting electrodes of oxidised aluminium, a spin-coated film converted at 220° C. in vacuo for two hours, and with electron injecting electrodes of aluminium.
Figure 15:
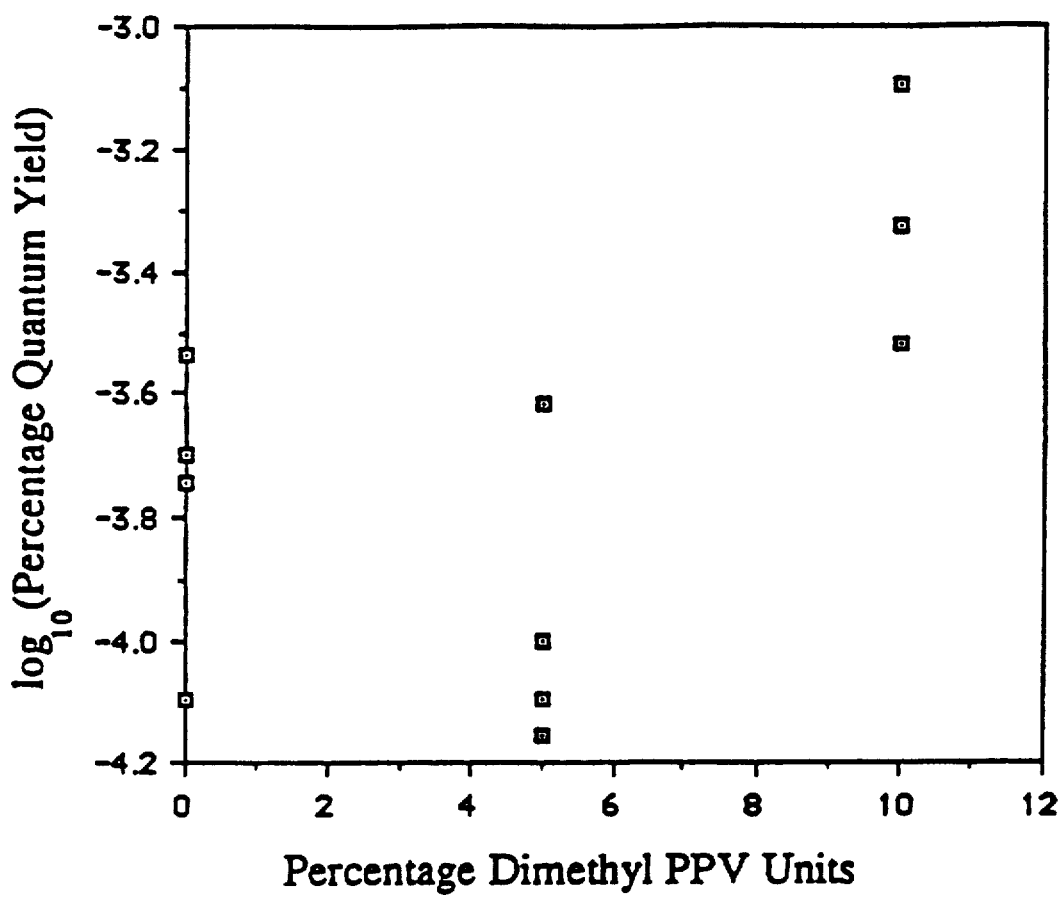
FIG. 15 illustrates the electroluminescent quantum yield of random copolymers formed from PPV and dimethyl-PPV monomer units as measured in thin film structures with hole injecting electrodes of oxidised aluminium, a spin-coated film converted at 220° C. in vacuo for two hours, and with electron injecting electrodes of aluminium.

Typical results of the PPV homopolymer, a copolymer obtained by in vacuo thermal conversion of spincoating thin films of spin coated films of a precursor copolymer synthesised from 90% para-phenylene vinylene/10% 2,5-dimethoxy-para-phenylene vinylene precursor units, a copolymer obtained by in vacuo thermal conversion of spin-coated thin films of a precursor copolymer synthesised from 90% para-phenylene vinylene/10% 2,5-thienylene vinylene precursor units and a copolymer obtained by in vacuo thermal conversion of spin-coated thin films of a precursor copolymer synthesised from 90% para-phenylene vinylene/10% 2-methoxy-5-(2'-methylpentyloxy) -para-phenylene vinylene precursor units are shown in FIGS. 10, 11, 12, 20 and 21 which present the current versus voltage and light output versus current characteristics. In FIG. 10 the bottom contact thickness is 110 Å, the top contact thickness is 1300 521 and the thickness of the electroluminescent layer is 900 Å. In FIG. 11 the corresponding thickness values are 120 Å, 1000 Å and 1450 Å and in FIG. 13 they are 90 Å, 1370 Å and 1070 Å. Similar current versus voltage characteristics were found for all devices, with a threshold voltage for current injection of around 25 to 40V. There was also found a broadly linear relation between current and light output (which allows the efficiency of the device to be characterised simply, by the gradient of this plot).

It is found that the light output varies strongly with the choice of copolymer, and that some of the copolymers show very strongly enhanced efficiencies as measured against the efficiency of the PPV homopolymer. The variation of the quantum efficiency is shown as actually measured (current in photodetector/current through EL device) in FIGS. 13, 14, 15 and 31 for the copolymers obtained from the in vacuo thermal conversion of spin-coated thin films of precursor copolymers formed between the precursors to PPV and PDMOPV, the precursors to PPV and PTV, the precursors to PPV and PDMPV, and the precursors to PPV and MMP-PPV respectively. The plots show some data for a large number of devices, and there is some scatter evident between devices of the same nominal composition. This may be due to inhomogeneities in the devices, such as non-uniform thickness, entrapped dust particles etc. and it is considered that the better values of efficiency at each composition give a true indication of the intrinsic behaviour of the EL structure. The PPV/PDMOPV copolymers show a very big improvement in efficiency for PDMOPV in the range 5-15%, with best results at 10%, for which the improvement over that obtained for PPV is by a factor of about 50. The PPV/PTV copolymers do not show such behaviour. This may be compared with the very low quantum yield for photoluminescence (less than or of order $10^{-5}$) that is found in the homopolymer, as in "Optical Excitations in Poly(2,5-thienylene vinylene)", A. J. Brassett, N. F. Colaneri, D. D. C. Bradley, R. A. Lawrence, R. H. Friend, H. Murata, S. Tokito, T. Tsutsui and S. Saito, Phys. Rev. B 41, 10586 (1990). For the PPV/PDMPV copolymers an improvement over the PPV homopolymer is seen at 10% PDMPV, but the changes are less marked than with the PPV/PDMOPV copolymers.

The maximum measured efficiencies for the devices shown here, obtained for the 90/10% PPV/PDMOPV copolymer, approach $10^{-2}$%. To obtain the real efficiency of the EL layer in the device it is necessary to correct for the efficiency of the photodetector (50%), the collection efficiency for the EL (24%) and the optical transmittance of the Al semitransparent layer (30%). With these factors included, it is estimated that the real efficiency of the EL layer in such a device is as high as 0.3%. This value compares very favourably with the performance of EL devices fabricated with other materials.

As PL and EL are due to the same excited state in the polymer, as evidenced by the similarity in emission recorded for a single polymer film, a correspondence between efficiency for EL and for PL is broadly to be expected. However, there are some differences as discussed below.

The efficiency for luminescence is in part an intrinsic property of the material (that is to say that it has the same value for all samples), and possibly also dependent on the actual form of the sample and the nature of the interfaces to it. Thus, it might be expected for the thin films used for the EL structures that migration of the excited states to the interface between the polymer film and the electrode material might result in non-radiative decay of the excited state, and thus allow the efficiency for luminescence to fall below its "intrinsic" value. The effect, then of restricting the motion of the excited states in the copolymers may be to improve quantum yield both by improving the intrinsic properties of the polymer, and also by reducing the motion of excited states to the interface region. Thus, the improvements in quantum yield that have been measured in EL for some of the copolymers are by a very large factor ($\times 50$), considerably larger than the factor by which the yield for PL is improved.

There has been described a design technique and a method of manufacture for achieving especially efficient emission in conjugated copolymer electroluminescent structures through the use of the local modulation of semiconductor energy gap, between the highest occupied and lowest unoccupied energy levels, achieved in copolymers of two or more different monomer units. The modulation of energy gap is achieved by the use, in the copolymer structure, of chemically-different monomer units which in their individual homopolymer forms have different energy gaps. The effect of the energy gap modulation is to produce local regions that are potential energy minima and that act to confine the exciton states created by injection of electrons and holes from the contact layers. This confinement is beneficial for efficient radiative recombination of excitons through its reduction of the opportunities for migration of the excitons to non-radiative recombination sites subsequent to their initial generation and thus leads to a higher electroluminescent yield.

The copolymers described herein are intractable, insoluble in common solvents and infusible at temperatures below the decomposition temperature, or they are soluble in a few organic solvents.

We claim:

1. A method of forming in a semiconductive conjugated polymer at least a first region and a second region having different optical properties from one another, said method comprising:
- (a) forming a layer of a precursor polymer, wherein the precursor polymer comprises a poly(arylene-1,2-ethanediyl) polymer having a proportion of the ethane groups including a modifier group whose susceptibility to elimination is increased in the presence of an acid;
- (b) generating in the layer of precursor polymer the first region having a first optical property and the second region having a second optical property, said step of generating the first region includes the step of contacting the first region of the precursor polymer with an amount of acid and heating sufficiently to generate a first region of a semiconductive conjugated polymer having a first optical property, wherein the step of contacting the first region with acid comprises:
  - (i) providing the acid to the layer of precursor polymer wherein the acid is provided to the precursor polymer by release from the precursor polymer in the presence of heat; and
  - (ii) applying a protective coating in a pattern to the surface of the layer of precursor polymer to form a coated portion and an uncoated portion of the precursor polymer wherein the coated portion traps the acid.

2. A method of forming in a semiconductive conjugated polymer at least a first region and a second region having different optical properties from one another, said method comprising:
- (a) forming a layer of a precursor polymer, wherein the precursor polymer comprises a poly(arylene-1,2-ethanediyl) polymer, wherein a proportion of the ethane groups are substituted with a modifier group whose susceptibility to elimination is increased in the presence of a acid;
- (b) generating in the layer of a precursor polymer the first region having a first optical property and the second region having a second optical property, wherein said step of generating the first region comprises:
  - (i) applying a protective coating in a pattern to the surface of the precursor polymer to form a precursor polymer with a coated and uncoated region; and
  - (ii) applying an acid to the uncoated region; and
  - (iii) heating the precursor polymer sufficiently to generate the first region.

3. A method according to claim 2, wherein said step of generating the second region comprises contacting the layer of a precursor polymer in the second region with the same acid as used in the step of contacting the first region, but in a lower concentration.

4. A method of forming in a semiconductive conjugated polymer at least a first region and a second region having different optical properties from one another, said method comprising:
- (a) forming a layer of a precursor polymer wherein the precursor polymer comprises a poly(para-phenylene-1,2-ethanediyl) polymer having a proportion of ethane groups including a modifier group whose susceptibility to elimination is increased in the presence of an acid;
- (b) generating in the layer of precursor polymer a first region having a first optical property and a second region having a second optical property, wherein said step of generating the first region includes the steps of contacting the layer of precursor polymer with an amount of an acid and heating sufficiently to form the first region so as to enhance the efficiency of photoluminescence or electroluminescence of the polymer.

5. A method of forming in a semiconductive conjugated polymer at least a first region and a second region having different optical properties from one another, said method comprising:
- (a) forming a layer of a precursor polymer wherein the precursor polymer comprises a poly(arylene-1,2-ethanediyl) polymer having a proportion of ethane groups including a modifier group whose susceptibility to elimination is increased in the presence of an acid;
- (b) generating in the layer of precursor polymer the first region having a first optical property and the second region having a second optical property, wherein said step of generating the first region includes the steps of contacting the layer of precursor polymer with an amount of an acid and heating sufficiently to form the first region so that a different wavelength of radiation is emitted during luminescence than in the second region.

6. A method according to claim 5, wherein the composition of the copolymer in at least one of the regions has been chosen so as to enhance the efficiency of photoluminescence or electroluminescence of the polymer.

7. A method according to claim 5, wherein the optical properties of the polymer are controlled so as to select the refractive index of the polymer.

8. A method according to claim 5, wherein the step of generating the second region comprises contacting the layer of precursor polymer in the second region with the same acid as used in the step of contacting the first region, but in lower concentration.

9. A method as claimed in claim 5, wherein, in the step of generating the first region, heating is conducted at a temperature of about 100° to 300° C. until the first region is generated.

10. A method as claimed in claim 9, wherein, in the step of generating the first region, the heating is conducted for about 1-24 hours.

11. A method according to claim 5, wherein, in the step of generating the first region, heating is controlled so as to control the extent of elimination of the modifier group.

12. A method according to claim 5, wherein the modifier group is substantially stable to heat in the absence of acid.

13. A method according to claim 12, wherein the modifier group comprises an alkoxy group.

14. A method according to claim 13, wherein the alkoxy group is a methoxy group.

15. A method according to claim 5, wherein the conjugated polymer is a copolymer comprising at least two different monomer units which, in their individual homopolymer forms have different optical properties, the proportion of the monomer units in the copolymer having been selected to control the optical properties of the copolymer.

16. A method as claimed in claim 15, wherein the monomer units form arylene moieties in the copolymer chain having as a first component para-phenylene and a second component selected from the group consisting of 2,5-dimethoxy-para-phenylene; 2,5-thienylene; 2,5-dimethyl-para-phenylene; 2-methoxy-5-(2'-methylpentyloxy)-para-phenylene; and 2-methoxy-5-(2'-ethylhexyloxy)-para-phenylene.

17. A method according to claim 16, wherein para-phenylene comprises at least 70% of the total amount of arylene moieties present.

18. A method according to claim 16, wherein para-phenylene constitutes an amount in the range of 70–95% of the total amount of arylene moieties present and wherein the second component is 2,5-dimethoxy-para-phenylene.

19. A method according to claim 15, wherein at least one of the monomer units of the copolymer of at least one of the regions is not fully conjugated in the chains of the polymer.

20. A method according to claim 5, wherein the conjugated polymer retains some of the modifier groups so as to saturate a proportion of the vinylic groups of the polymer to control the extent of conjugation of the polymer thereby controlling the optical properties of the polymer.

21. A method according to claim 5, wherein the precursor polymer comprises a homopolymer.

22. A method according to claim 21, wherein the homopolymer is selected from the group consisting of a poly(2,5-dimethoxy-para-phenylene-1,2-ethanediyl) polymer, a modified poly(thienylene-1,2-ethanediyl) polymer, a poly(2-methoxy-5-(2'-methylpentyloxy)-para-phenylene-1,2-ethanediyl) polymer, and a poly(2-methoxy-5-(2'-ethylhexyloxy)-para-phenylene-1,2-ethanediyl) polymer.

23. A method according to claim 5, wherein the chain of the semiconductive conjugated polymer in at least one of the regions is fully conjugated.

24. A method of forming in a semiconductive conjugated polymer at least a first region and a second region having different optical properties from one another, said method comprising:
(a) forming a layer of a precursor polymer wherein the precursor polymer comprises a poly(arylene-1,2-ethanediyl) polymer having a proportion of ethane groups including a modifier group whose susceptibility to elimination is increased in the presence of an acid;
(b) generating in the layer of precursor polymer the first region having a first optical property and the second region having a second optical property, said step of generating the first region including the step of contacting the first region of the precursor polymer with an amount of acid and heating sufficiently to generate a first region of a semiconductive conjugated polymer having a first optical property, wherein the step of contacting the first region with acid comprises:
(i) providing the acid to the layer of precursor polymer wherein the acid is provided to the precursor polymer by release from the precursor polymer in the presence of heat;
(ii) applying a protective coating in a pattern to the surface of the layer of precursor polymer to form a coated portion and an uncoated portion of the precursor polymer wherein the coated portion traps the acid and wherein the step of applying a coating in a pattern comprises:
(A) applying a coating to the surface of the precursor polymer to form a coated precursor polymer;
(B) applying a layer of photoresist to the coated precursor polymer;
(C) activating the layer of photoresist in a pattern to form a photoresist protected and unprotected coating;
(D) removing the unprotected coating; and
(E) removing the remaining photoresist.

25. A method of forming in a semiconductive conjugated polymer at least a first region and a second region having different optical properties from one another, said method comprising:
(a) forming a layer of a precursor polymer, wherein the precursor polymer comprises a poly(arylene-1,2-ethanediyl) polymer, wherein a proportion of the ethane groups are substituted with a modifier group whose susceptibility to eliminating is increased in the presence of acid;
(b) generating in the layer of a precursor polymer the first region having a first optical property and the second region having a second optical property, wherein said step of generating the first region comprises:
(i) applying a protective coating in a pattern to a portion of the surface of the layer of the precursor polymer to form a precursor polymer with a coated and uncoated region, wherein the step of applying a protective coating further comprises:
(A) applying a layer of photoresist to the coated region;
(B) activating the layer of photoresist to form a photoresist protect and unprotected coating;
(C) removing the unprotected coating; and
(D) removing the remaining photoresist;
(ii) applying acid to the uncoated region; and
(iii) heating the precursor polymer sufficiently to generate the first region
wherein the step of generating the second region comprises:
(iv) contacting the layer of precursor polymer in the second region with the same acid as was used in the step of contacting the first region, but in lower concentration.

* * * * *

UNITED STATES PATENT AND TRADEMARK OFFICE
CERTIFICATE OF CORRECTION

PATENT NO. : 5,328,809
DATED : July 12, 1994
INVENTOR(S) : Holmes et al.

It is certified that error appears in the above-indentified patent and that said Letters Patent is hereby corrected as shown below:

On title page, item [75] should read as follows:

--Andrew B. Holmes; Donal D. Bradley; Richard H. Friend; Arno Kraft; Paul L. Burn; Adam R. Brown--.

Column 5, line 10, "et al" should read --et al.,--.

Column 5, line 55 "moieties" should read --moieties'--.

Column 6, line 6, "-$CH_2^{L1}$" should read -- -$CH_2L^1$--.

Column 6, line 43, "$CH_2^{L1}$" should read --$CH_2L^1$--.

Column 6, line 43, "$CH_2^{L2}$" should read --$CH_2L^2$--.

Column 6, line 45, "$CH_2^{L4}$" should read --$CH_2L^4$--.

Column 9, line 45, "present" should read --presence--.

Column 9, line 59, "are graphs" should read --is a graph--.

Column 10, line 32, "are graphs" should read --is a graph--.

UNITED STATES PATENT AND TRADEMARK OFFICE
CERTIFICATE OF CORRECTION

PATENT NO. : 5,328,809
DATED : July 12, 1994
INVENTOR(S) : Holmes et al.

It is certified that error appears in the above-indentified patent and that said Letters Patent is hereby corrected as shown below:

Column 11, lines 27, 33, 51, 57, and 66, "are graphs" should read --is a graph--.

Column 12, line 21, "thin;films" should read --;thin films--.

Column 13, line 4, "focal" should read --formal--.

Column 13, line 22, "are graphs" should read --is a graph--.

Column 13, line 43, "emision" should read --emission--.

Column 17, line 34, "(s,H)." should read --(s,3H), 4.62 (s,2H), 4.64 (s,2H), 6.89 (s,1H), 6.92 (s,1H).--.

Column 17, line 42, "C5902" should read --C59.02--.

Column 15, lines 60 and 61, "$\alpha,\alpha$" should read --$\alpha,\alpha'$--.

Column 16, lines 12 and 13, "$\alpha,\alpha$" should read --$\alpha,\alpha'$--.

Column 16, lines 32 and 33, "$\alpha,\alpha$" should read --$\alpha,\alpha'$--.

UNITED STATES PATENT AND TRADEMARK OFFICE
CERTIFICATE OF CORRECTION

PATENT NO. : 5,328,809  
DATED : July 12, 1994  
INVENTOR(S) : Holmes et al.

It is certified that error appears in the above-indentified patent and that said Letters Patent is hereby corrected as shown below:

Column 17, lines 46 and 56, "α,α" should read --α,α'--.

Column 18, lines 2 and 3, "α,α" should read --α,α'--.

Column 18, line 66, after "(m,2H)", insert --3.83 (s,3H), 4.06 (s,4H), 6.89 (s,1H), 6.90 (s,1H).--

Column 18, line 68, "614(m)" should read --614cm$^{-1}$(m).--.

Column 22, line 14, "500A" should read --500Å--.

Column 23, line 38, "electron" should read -- -

Column 27, line 28, "1300 521" should read --1300 Å--.

UNITED STATES PATENT AND TRADEMARK OFFICE
CERTIFICATE OF CORRECTION

PATENT NO. : 5,328,809
DATED : July 12, 1994
INVENTOR(S) : Holmes et al.

It is certified that error appears in the above-indentified patent and that said Letters Patent is hereby corrected as shown below:

Col. 32, claim 25, line 27, "eliminating" should read —elimination—.

Signed and Sealed this

Sixteenth Day of May, 1995

Attest:

BRUCE LEHMAN

Attesting Officer

Commissioner of Patents and Trademarks